(12) United States Patent     (10) Patent No.: US 12,263,056 B2
McGann et al.     (45) Date of Patent: Apr. 1, 2025

(54) GENERATING THREE-DIMENSIONAL ORTHODONTIC SIMULATIONS

(71) Applicant: Progressive Aligners, Inc., Aliso Viejo, CA (US)

(72) Inventors: Benson Donald McGann, Henderson, NV (US); Miles McGann, Ladera Ranch, CA (US)

(73) Assignee: Progressive Aligners, Inc., Aliso Viejo, CA (US)

( * ) Notice: Subject to any disclaimer, the term of this patent is extended or adjusted under 35 U.S.C. 154(b) by 0 days.

(21) Appl. No.: 18/432,798

(22) Filed: Feb. 5, 2024

(65) Prior Publication Data

US 2024/0261063 A1    Aug. 8, 2024

Related U.S. Application Data

(60) Provisional application No. 63/483,219, filed on Feb. 3, 2023.

(51) Int. Cl.
*A61C 7/00*     (2006.01)
*A61B 34/10*     (2016.01)
*A61C 9/00*     (2006.01)

(52) U.S. Cl.
CPC .............. *A61C 7/002* (2013.01); *A61B 34/10* (2016.02); *A61C 9/0053* (2013.01); *A61B 2034/105* (2016.02); *A61B 2034/107* (2016.02); *A61C 2007/004* (2013.01)

(58) Field of Classification Search
CPC ......... A61C 7/00; A61C 7/002; A61C 9/0053; A61C 2007/004; A61B 34/10; A61B 2034/105; A61B 2034/107
See application file for complete search history.

(56) References Cited

U.S. PATENT DOCUMENTS 8,587,582 B2   11/2013   Matov et al.
10,179,035 B2   1/2019   Shivapuja et al.
10,507,079 B2   12/2019   Miller
(Continued)

FOREIGN PATENT DOCUMENTS

WO    WO/2022/189906 A1    9/2022

OTHER PUBLICATIONS

International Search Report issued in International Application No. PCT/US2024/014418 dated Jul. 3, 2024.
(Continued)

*Primary Examiner* — Yogesh P Patel
(74) *Attorney, Agent, or Firm* — Vos-IP, LLC

(57) ABSTRACT

Methods for providing results of orthodontic realignment simulations comprising: obtaining three-dimensional virtual models of dental arches, the models compiled from intraoral scans of a mouth; based on the shapes of the modeled dental arches, selecting matching predefined archforms; obtaining at least one of: a first set of rules that define anterior and posterior molar movement, a second set of rules that determine a path of tooth movement to the matching predefined archforms, or a third set of rules that define simulation mechanics for moving at least one tooth to a final position based on known endpoint data and the matching predefined archforms; and based on results from implementing at least one set of rules, determining final positions of the teeth in relation to the matching predefined archforms.

11 Claims, 19 Drawing Sheets

(56) References Cited

U.S. PATENT DOCUMENTS

| | | | |
|---|---|---|---|
| 11,266,484 B2 | 3/2022 | Mason et al. | |
| 11,478,333 B2 | 10/2022 | Kitching et al. | |
| 11,484,390 B2 | 11/2022 | Shivapuja | |
| 11,678,954 B2 * | 6/2023 | Wu | A61C 7/002 |
| | | | 703/11 |
| 11,806,602 B2 | 11/2023 | Kuo | |
| 2004/0029068 A1 | 2/2004 | Sachdeva et al. | |
| 2020/0237481 A1 | 7/2020 | Kuo et al. | |
| 2021/0106403 A1 | 4/2021 | Aptekarev et al. | |
| 2022/0000592 A1 * | 1/2022 | Ramirez | G06T 19/20 |
| 2023/0153476 A1 | 5/2023 | Fabbri et al. | |

OTHER PUBLICATIONS

"Cephalogram", Wikipedia, Nov. 25, 2022, https://en.wikipedia.org/w/index.php?title=Cephalogram&oldid=1123675022.

"Orthodontic Indices", Wikipedia, Aug. 16, 2022, https://en.wikipedia.org/w/index.php?title=Orthodontic_indices&oldid=1104711186.

Tartaglia, et al., "Direct 3D Printing of Clear Orthodontic Aligners: Current State and Future Possibilities", Materials, vol. 14, No. 7, art. 1799, Apr. 5, 2021, 1-11.

* cited by examiner

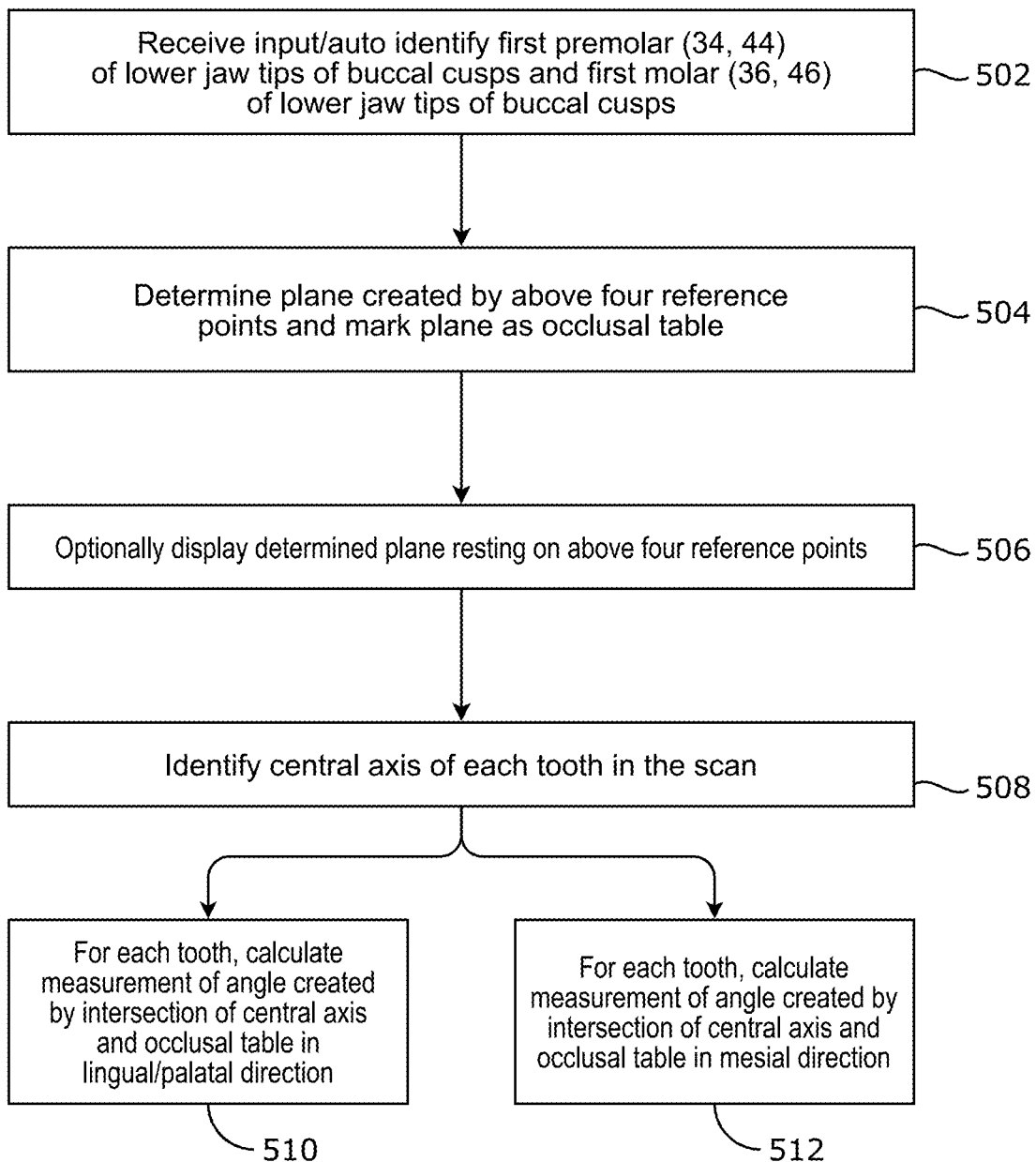

FIGURE 8

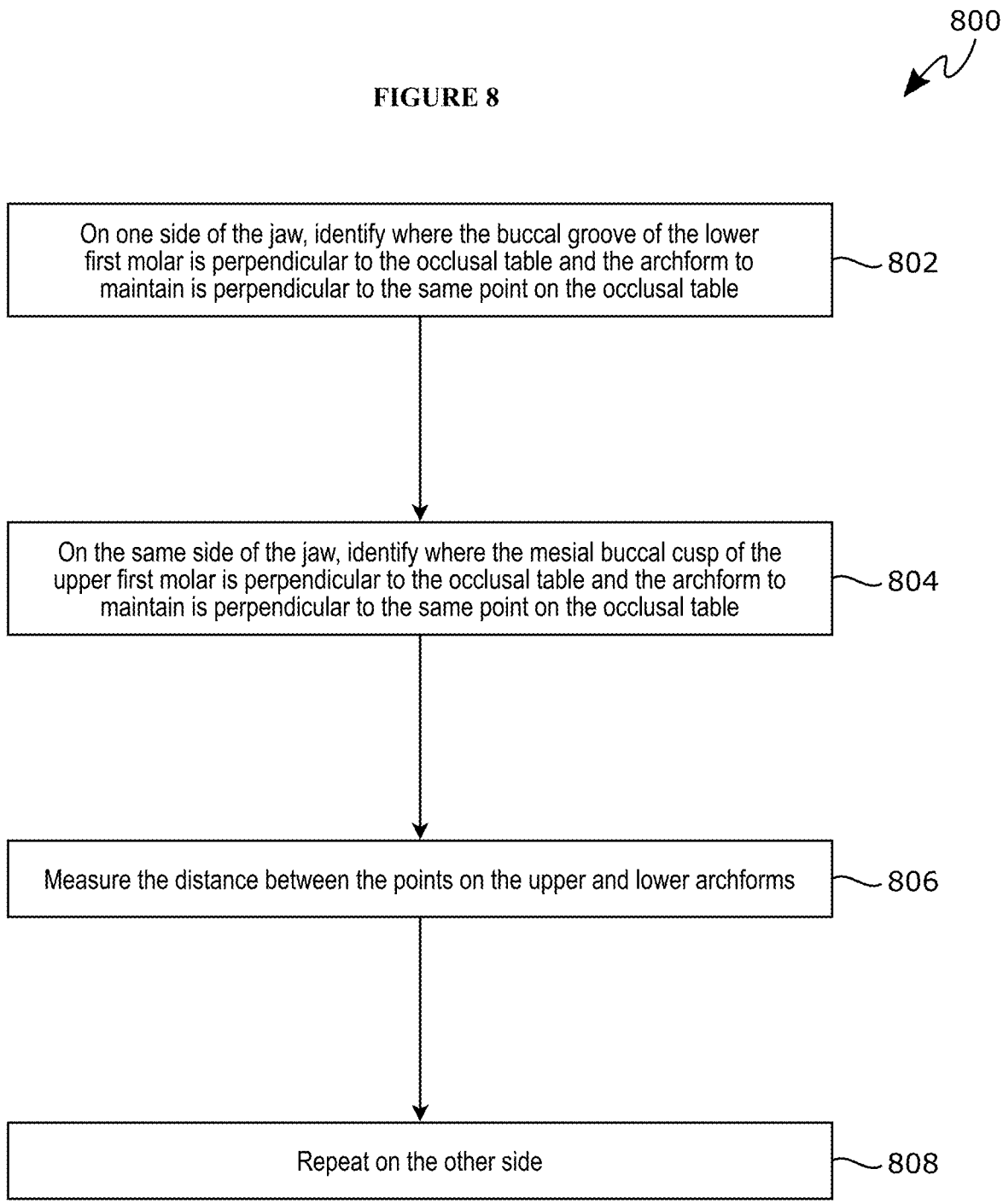

```
┌─────────────────────────────────────────────────────────────┐
│ On one side of the jaw, identify where the buccal groove    │
│ of the lower first molar is perpendicular to the occlusal   │— 802
│ table and the archform to maintain is perpendicular to      │
│ the same point on the occlusal table                        │
└─────────────────────────────────────────────────────────────┘
                              │
                              ▼
┌─────────────────────────────────────────────────────────────┐
│ On the same side of the jaw, identify where the mesial      │
│ buccal cusp of the upper first molar is perpendicular to    │— 804
│ the occlusal table and the archform to maintain is          │
│ perpendicular to the same point on the occlusal table       │
└─────────────────────────────────────────────────────────────┘
                              │
                              ▼
┌─────────────────────────────────────────────────────────────┐
│ Measure the distance between the points on the upper        │— 806
│ and lower archforms                                         │
└─────────────────────────────────────────────────────────────┘
                              │
                              ▼
┌─────────────────────────────────────────────────────────────┐
│                   Repeat on the other side                  │— 808
└─────────────────────────────────────────────────────────────┘
```

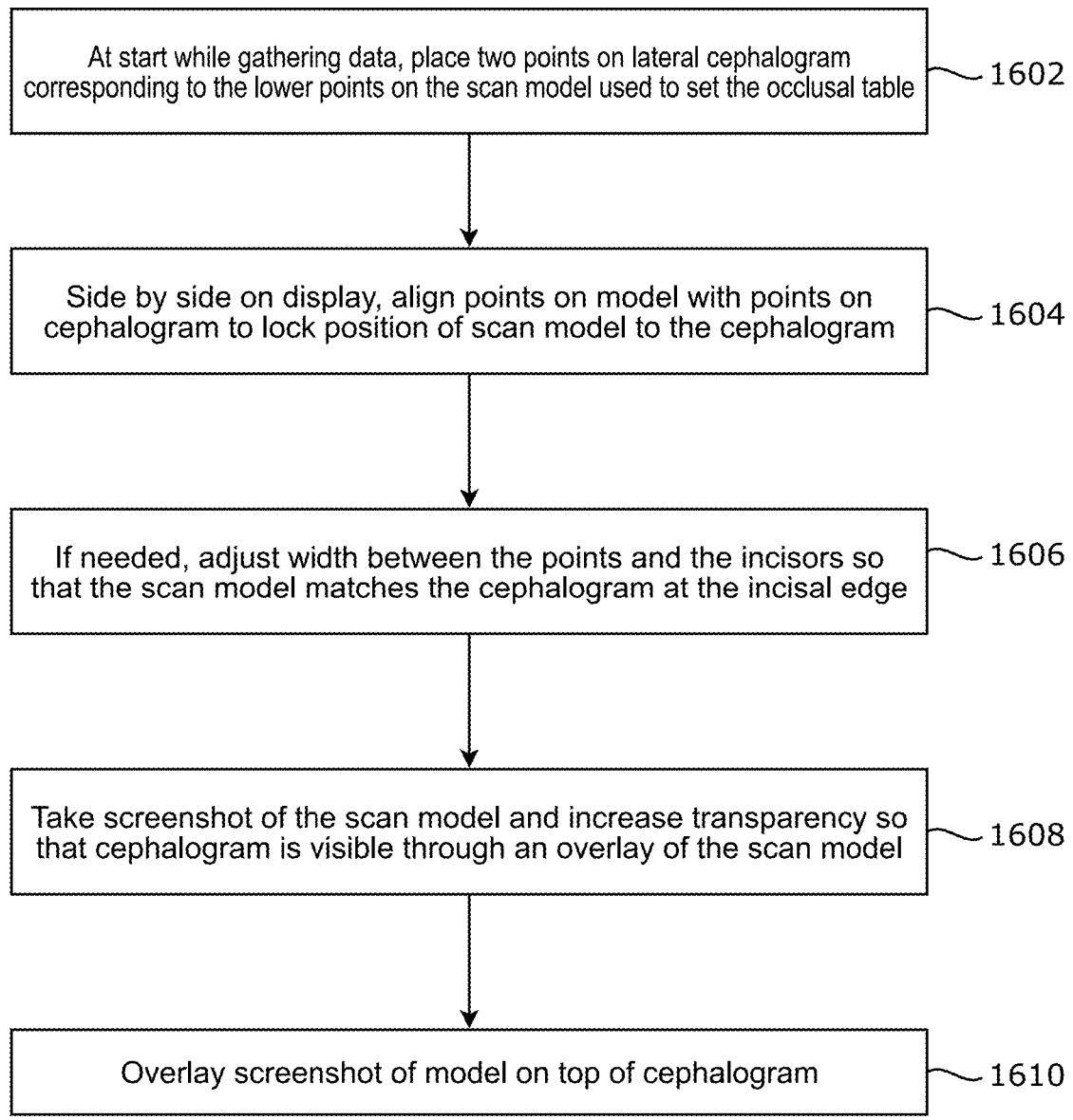

«GENERATING THREE-DIMENSIONAL ORTHODONTIC SIMULATIONS»

GENERATING THREE-DIMENSIONAL ORTHODONTIC SIMULATIONS

CROSS-REFERENCE TO RELATED APPLICATIONS

This application claims the benefit of U.S. Provisional Patent Application No. 63/483,219 filed on Feb. 3, 2023, with the United States Patent and Trademark Office, the contents of which are incorporated herein by reference in their entirety.

FIELD OF THE INVENTION

This disclosure relates generally to orthodontics and more specifically to simulations of potential treatment plans based on tooth positioning and skeletal dimensions of an individual, which may yield printable files to make orthodontic aligner apparatuses.

BACKGROUND OF THE INVENTION

Orthodontic care has evolved over the past 150 years. As early as the 1850s, the earliest gum elastics were utilized with certain metallic supports to straighten teeth. By the early 1900s development of the first classification system for malocclusions was created by the American Association of Orthodontists, and braces were made of precious metals. After World War II, the use of stainless steel emerged for orthodontic care, which continued to use metal, wrapped around the teeth, to provide support. It was not until the 1970s when brackets were directly adhered to the teeth.

In 1997, clear aligner options were first made available, which utilized clear plastic or polymer trays instead of brackets on teeth. However, these aligners are made based on a singular ideal end model, a one size fits all approach, which is time consuming to formulate and yields incomplete treatment plans. In particular, the trays are formulated to a singular simulation model, regardless of the starting point of the patient. This may cause problems in proper tooth movement and end results. Furthermore, this approach assumes that each patient can conform to the singular ideal tooth position, without consideration of the entirety of the patient. For example, if a patient needs widening of the oral bridge to conform to the ideal, a manipulation of bite can modify facial structure, sometimes dramatically. Furthermore, in certain cases, some teeth are so out of position that use of aligners alone would be ill advised.

Recent developments of intraoral scanning devices provide new options for generating a scan of hard and soft tissues of the mouth, enabling the digital/virtual creation of a complete image of the mouth and a three-dimensional replication of exact tooth position and surface anatomy. As disclosed herein, the precision of such digitization has enabled us to elucidate orthodontic treatments plans that take skeletal and current tooth positions information into consideration for generating one or more simulations of orthodontic treatment for that particular patient. Because each patient has individual oral challenges, our simulations allow the patient to select a treatment plan (and end result) that is satisfactory to the patient. Our patients are not forced to accept results that are not attuned to their particular orthodontic needs; from the start, they can observe several different treatments plans and observe end results that are possible from each simulated scenario.

SUMMARY OF THE INVENTION

The embodiments of the invention herein relate to orthodontic simulations, and to systems for creating orthodontic apparatuses, such as aligners to enact the orthodontic simulation. The orthodontic simulations are generated by obtaining tooth data from one or more of an intraoral scan, a cephalometric X-ray, an X-ray, manual input, and other pictures and/or data that is used to generate a three-dimensional view of the mouth, bony structures, and teeth of a patient. Using enumerated rules regarding a proposed endpoint position for each tooth along an archform, and occlusal table, the system, using rules and logic generates the orthodontic simulation and provides for an output that may include a bracket plan to enact the orthodontic simulation, a data file corresponding to one or more aligners (trays), or combinations thereof, to reach the desired final tooth position. Uniquely, the system can reproducibly generate an orthodontic simulation plan from a given starting point, and can generate a printable file, including printing of an aligner apparatus in about an hour of time, which heretofore could not be performed with such reproducibility and/or speed as any prior art system.

In a preferred embodiment, a method for providing a result of an orthodontic realignment simulation comprising: (a) obtaining a three-dimensional virtual model of an upper dental arch, lower dental arch, or both, the three-dimensional virtual model compiled from an intraoral scan of a mouth; (b) based on a shape of a modeled upper dental arch, a modeled lower dental arch, or both, selecting a predefined archform; (c) obtaining at least one of: (i) a first set of rules that define anterior and posterior molar movement; and/or (ii) a second set of rules that determine a path of tooth movement to the predefined archform; and/or (iii) a third set of rules that define a simulation mechanics for moving at least one tooth to a final position based on known endpoint data and the predefined archform; and (d) based on a result from implementing at least one of the first set of rules and/or the second set of rules and/or third set of rules, determining a final position of at least one tooth within the upper dental arch or the lower dental arch in relation to the predefined archform, yielding the orthodontic realignment simulation.

In a further embodiment, the method comprising determining an occlusal table.

In a further embodiment, the method comprising wherein the occlusal table is identified from four points on a lower dental arch to define the occlusal table.

In a further embodiment, the method wherein the occlusal table is defined by identifying four points on the lower dental arch includes identifying cusp tips of a first and a second premolar and distal cusp tips of a first molar and a second molar.

In a further embodiment, the method further comprising determining a molar movement by selecting a molar bite class.

In a further embodiment, the method further comprising: identifying a buccal cusp of an upper first molar in the model; identifying a buccal groove of a lower first molar in a lower the model; determining a molar bite class by identifying on the occlusal table where a line from the buccal cusp perpendicularly intersects the occlusal table at a first intersection and where a line from the buccal groove perpendicularly intersect the occlusal table at a second intersection; from the first intersection, identifying a point on an upper archform that is perpendicular thereto and from the second intersection, identifying a point on a lower archform that is perpendicular thereto; and measuring a difference between the point on the upper archform and the point on the lower archform to classify a bite difference.

In a further embodiment, the method further comprising wherein obtaining the second set of rules comprises obtaining a second set of rules that does not allow collisions between teeth that prevent subsequent movement.

In a further embodiment, the method further comprising wherein obtaining the third set of rules comprises defined simulation mechanics selected from the group consisting of: nonextraction mechanics, extraction mechanics, distalization mechanics, mechanics that maintain the predefined archform, mechanics that replace the predefined archform, mechanics that correct for posterior crossbite, mechanics that include interproximal reduction (IPR), mechanics that accommodate growth, postsurgery mechanics, and combinations thereof.

In a further embodiment, the method further comprising calculating a starting angulation and a starting inclination of a tooth in the three-dimensional virtual model based on an angle created by the occlusal table and a central axis of the tooth.

In a further embodiment, the method further comprising calculating a starting rotation of the tooth based on a comparison of a distance from a mesial side of the tooth to the predefined archform to a distance from a distal side of the tooth to the predefined archform.

In a further embodiment, the method wherein the starting inclination, angulation, and rotation measurements are compared to the inclination, angulation, and rotation measurements of the third set of rules to determine a differences in starting and ending inclination, angulation, and rotation.

In a further embodiment, the method wherein movement of the tooth from starting positions to end positions is determined in increments of less than 0.2 mm for distance changes and 3° for angle changes.

In a further embodiment, the method wherein the orthodontic realignment simulation further comprises printable instructions including an option to print a new orthodontic aligner suitable to implement the orthodontic realignment simulation.

In a further embodiment, the method further comprising measuring an actual ending inclination and angulation using the occlusal table and measuring an ending rotation using the predefined archform.

In a preferred embodiment, use of an orthodontic aligner to implement the method wherein the orthodontic aligner is provided to impart a force to the at least one tooth in order to effect the orthodontic realignment simulation.

In a preferred embodiment, a method for providing a result of an orthodontic realignment simulation comprising: (a) obtaining a three-dimensional virtual model of an upper dental arch, lower dental arch, or both, the three-dimensional virtual model compiled from an intraoral scan of a mouth; (b) based on a shape of a modeled upper dental arch, a modeled lower dental arch, or both, selecting a matching predefined archform; (c) obtaining a first set of rules that define anterior and posterior molar movement; (d) obtaining a second set of rules that determine a path of tooth movement to the matching predefined archform; (e) obtaining a third set of rules that define a simulation mechanics for moving at least one tooth to a final position based on known endpoint data and the matching predefined archform; and (f) based on a result from implementing each of the first set of rules, second set of rules, and third set of rules, determining a final position of the at least one tooth in relation to the matching predefined archform.

In a further embodiment, a method wherein obtaining a first set of rules comprises obtaining a first set of rules that are specific to the simulation mechanics.

In a further embodiment, a method wherein obtaining the second set of rules comprises obtaining a second set of rules that does not allow collisions between teeth that prevent subsequent movement.

In a further embodiment, a method wherein obtaining the third set of rules comprises defined simulation mechanics selected from the group consisting of: nonextraction mechanics, extraction mechanics, distalization mechanics, mechanics that maintain the matching predefined archform, mechanics that replace the matching predefined archform, mechanics that correct for posterior crossbite, mechanics that include interproximal reduction (IPR), mechanics that accommodate growth, postsurgery mechanics, and combinations thereof.

In a further embodiment, a method wherein obtaining the third set of rules comprises looking up an endpoint table corresponding to the third set of rules and to a skeletal class, the endpoint table defining known endpoint data.

In a preferred embodiment, a method for determining a molar bite classification using a virtual three-dimensional model of an intraoral scan comprising: (a) identifying an occlusal table; (b) identifying a predefined archform that emulates an arch of a model that is virtual and three-dimensional; (c) identifying a buccal cusp of an upper first molar in the model; (d) identifying a buccal groove of a lower first molar in a lower the model; (e) identifying on the occlusal table where a line from the buccal cusp perpendicularly intersects the occlusal table at a first intersection and where a line from the buccal groove perpendicularly intersects the occlusal table at a second intersection; (f) from the first intersection, identifying a point on an upper archform that is perpendicular thereto and from the second intersection, identifying a point on a lower archform that is perpendicular thereto; and (g) measuring a difference between the point on the upper archform and the point on the lower archform to classify a bite difference.

In a further embodiment, the method wherein identifying the occlusal table comprises identifying four points on a lower dental arch to define the occlusal table.

In a further embodiment, the method wherein identifying four points on the lower dental arch includes identifying cusp tips of a first and a second premolar and distal cusp tips of a first molar and a second molar.

In a preferred embodiment, a method for creating a printable orthodontic simulation comprising: (a) obtaining image data of an upper dental arch, lower dental arch, or both, and compiling the image data into a virtual three-dimensional model; (b) obtaining a predefined archform conforming to a dental arch of the virtual three-dimensional model, the predefined archform providing a reference for determining tooth positions and alignment; (c) obtaining a first set of rules that define anterior and posterior molar movement; (d) obtaining a second set of rules that define nonmolar movement based on determined defined molar movements, both molar and nonmolar movement advancing toward the predefined archform; (e) obtaining a third set of rules that define a final inclination, angulation, and rotation for each tooth according to skeletal class; (f) based on a result from each of the first set of rules, second set of rules, and third set of rules, determining a final position for each tooth relative to the predefined archform and an occlusal table; and (g) generating a printable file comprising printable instructions for at least one orthodontic aligner, which is suitable to enact at least one step of a process defined by the printable orthodontic simulation.

In a further embodiment, the method further comprising wherein the occlusal table is based on cusps of lower first premolars and first molars of the virtual three-dimensional model.

In a further embodiment, the method further comprising calculating a starting angulation and inclination of a tooth in the virtual three-dimensional model based on an angle created by the occlusal table and a central axis of the tooth.

In a further embodiment, the method further comprising calculating a starting rotation of the tooth based on a comparison of a distance from a mesial side of the tooth to the predefined archform to a distance from a distal side of the tooth to the predefined archform.

In a further embodiment, the method wherein starting inclination, angulation, and rotation measurements are compared to the inclination, angulation, and rotation measurements of the third set of rules to determine a differences in starting and ending inclination, angulation, and rotation.

In a further embodiment, the method wherein movement of the tooth from starting positions to end positions is determined in increments of less than 0.2 mm for distance changes and 3° for angle changes.

In a further embodiment, the method wherein the printable instructions include an option to print a new orthodontic aligner for every other incremental change.

In a further embodiment, the method further comprising measuring an actual ending inclination and angulation using the occlusal table and measuring an ending rotation using the predefined archform.

In a further embodiment, the method wherein the first set of rules does not permit anterior or posterior movement and allows side-to-side movement, rotation, or both.

In a further embodiment, the method wherein obtaining a predefined archform comprises obtaining a predefined archform selected from the group consisting of: medium ovoid, nonextraction ovoid #2, small ovoid, nonextraction ovoid #1, large square, medium square, medium tapered, nonextraction tapered, and small tapered.

In a preferred embodiment, a method for determining tooth realignment by an orthodontic appliance comprising: (a) receiving from at least one of an intraoral scan, a cephalometric X-ray, an image, or combinations thereof a data set for constructing a virtual three-dimensional model of an upper dental arch, a lower dental arch, or both; (b) applying to the virtual three-dimensional model a selected predefined archform, the selected predefined archform having a shape that correlates to the upper dental arch, the lower dental arch, or both; (c) calculating a molar bite class from the virtual three-dimensional model by measuring a distance from a first point on a mesial buccal cusp of an upper first molar and a second point on a buccal groove of a lower first molar of the same side of the mouth and yielding a molar bite class of class I when the distance between the upper first molar and the lower first molar is from −0.99 mm to +0.99 mm, yielding a molar bite class of class II when the distance is greater than or equal to +1 mm, or yielding a molar bite class III when the distance is greater than −1 mm; (d) obtaining a first set of rules that define a molar movement based on the calculated molar bite class; (e) obtaining a second set of rules that define upper teeth and lower teeth movement to the selected predefined archform; (f) obtaining a third set of rules that define a final position of the teeth based on known endpoint data; and (g) based on a result from each of the first set of rules, second set of rules, and third set of rules, determining the realignment of each tooth.

In a preferred embodiment, a method for determining tooth realignment and a three-dimensional simulation showing the determined realignment comprising: (a) obtaining a three-dimensional virtual model of an upper dental arch, a lower dental arch, or both, the three-dimensional virtual model based on data from an intraoral scan; (b) positioning a depiction of a predefined archform proximate to the upper dental arch, the lower dental arch, or both, the predefined archform having a same shape as the dental arch to which it is proximate; (c) obtaining a first set of rules that define a molar movement; (d) obtaining a second set of rules that determine how upper teeth and lower teeth will move to the predefined archform based on predefined simulation mechanics for a determined molar bite class; (e) determining a third set of rules which defines a goal end position of each tooth in relation to the archform and an occlusal table provided that each tooth end position is defined according to:

|          | Tooth No | Inclination Degrees | Angulation Degrees | Rotation Degrees |
|----------|----------|---------------------|--------------------|------------------|
| Molar    | 18, 28   | 87-97               | 88-92              | 1-7              |
| Molar    | 17, 27   | 87-97               | 88-92              | 4-10             |
| Molar    | 16, 26   | 87-95               | 85-92              | 3-10             |
| Premolar | 15, 25   | 87-93               | 85-90              | 0-5              |
| Premolar | 14, 24   | 87-93               | 90-95              | 0-5              |
| Canine   | 13, 23   | 92-93               | 97-99              | 0-5              |
| Incisor  | 12, 22   | 53-72               | 97-99              | 0-5              |
| Incisor  | 11, 21   | 46-64               | 91-98              | 0-5              |
| Molar    | 38, 48   | 92-98               | 88-92              | 0-5              |
| Molar    | 37, 47   | 92-98               | 88-92              | 2-9              |
| Molar    | 36, 46   | 92-98               | 85-92              | 5-12             |
| Premolar | 35, 45   | 92-98               | 85-90              | 0-5              |
| Premolar | 34, 44   | 93-95               | 90-95              | 0-5              |
| Canine   | 33, 43   | 89-95               | 85-97              | 0-5              |
| Incisor  | 32, 42   | 54-80               | 90-95              | 0-5              |
| Incisor  | 31, 41   | 54-80               | 87-93              | 0-5              | and (f) based on a result from each of the first set of rules, second set of rules, and third set of rules, obtaining a simulated orthodontic realignment of each tooth.

In a preferred embodiment, a method for determining tooth realignment and a three-dimensional simulation showing the determined realignment comprising: (a) obtaining a three-dimensional virtual model of an upper dental arch, a lower dental arch, or both, the three-dimensional virtual model based on data from an intraoral scan and defining within the three-dimensional virtual model at least one of an upper tooth, a lower tooth, or both; (b) laying a depiction of a selected predefined archform proximate to the upper dental arch, a lower dental arch, or both within the three-dimensional virtual model; (c) obtaining a first set of rules that define a molar movement that proceeds in stages of no more than 0.2 mm or 3° of rotation per stage; (d) obtaining a second set of rules corresponding to an occlusal table, said second set of rules defining movement of at least one tooth regarding a rotation to the predefined archform; (e) obtaining a third set of rules that define a final position of at least one tooth based on an endpoint data; and (f) based on a result from each of the first set of rules, second set of rules, and third set of rules, determining and displaying the realignment of the at least one tooth.

In a preferred embodiment, a method of generating an orthodontic appliance suitable to effect an orthodontic simulation comprising: (a) obtaining a three-dimensional virtual model of an upper dental arch, lower dental arch, or both, the three-dimensional virtual model compiled from an intraoral scan of a mouth; (b) based on a shape of a modeled upper dental arch, a modeled lower dental arch, or both, selecting a matching predefined archform; (c) obtaining at least one of: (i) a first set of rules that define anterior and posterior molar movement; and/or (ii) a second set of rules that determine a path of tooth movement to the matching predefined archform; and/or (iii) a third set of rules that define a simulation mechanics for moving at least one tooth to a final position based on known endpoint data and the matching predefined archform; and (d) based on a result from implementing at least one of the first set of rules and/or second set of rules and/or the third set of rules, determining a final position of the at least one tooth in relation to the matching predefined archform; and (e) creating a datafile corresponding to at least one orthodontic appliance suitable to impart a force on at least one tooth within the upper dental arch or the lower dental arch to effect the orthodontic simulation.

In a further embodiment, the method wherein the three-dimensional virtual model is visualized on a display.

In a further embodiment, the method further comprising one or more of:

(a) determining a bite classification using the three-dimensional virtual model and identify predefined archform to measure the distance of a surface of a molar from the predefined archform; and/or (b) performing a WITS value based on a cephalographic X-ray; and/or (c) based on a determined bite classification, the WITS value and the predefined archform, calculating at least one simulation that shows teeth realignment to the predefined archform and display a calculated simulation on the display; and/or (d) based on an endpoint table for the calculated simulation, identifying a final realignment position of at least one tooth.

In a further embodiment, the method further comprising a step of defining an occlusal table from the three-dimensional virtual model comprising detecting two points on distal buccal cusps and two points on buccal/labial cusps of each premolar.

In a preferred embodiment, a method for automatically creating a dental alignment plan comprising: (a) obtaining a first set of data corresponding to a tooth position of at least one tooth, said first set of data obtained through an intraoral scan; (b) obtaining a first set of rules that define an archform corresponding to an optimized fit of the archform to the first set of data; (c) obtaining a molar bite class (MBC) from said first set of data to yield at least one endpoint table corresponding to a goal final position of the at least one tooth; (d) generating a movement pattern that defines movement of the at least one tooth from the tooth position to a final tooth position of the at least one tooth wherein the movement repositions the at least one tooth to the goal final position with regard to rotation of the tooth toward the archform or inclination of the tooth to an occlusal table; and wherein the movement is provided based upon available space according to the first set of rules; (e) confirming from the first set of rules the movement from the first position to the goal final position of the at least one tooth; and (f) generating a data file that defines a printable file to create an aligner sufficient to enact movement of the at least one tooth from the first position to a second intermediate position toward the goal final position.

In a further embodiment, the method wherein the predefined archform is selected from a group of predetermined archforms.

In a further embodiment, the method wherein the molar movement is defined according to any one of tables 1 to 16 and wherein the amount of movement is defined by the molar bite class.

In a further embodiment, the method further comprising determining a WITS value and wherein the end table simulation is modified based upon the selected of one of three WITS values.

In a further embodiment, the method wherein the movement is adjusted to accommodate growth-based age, gender, and projected growth.

In a further embodiment, the method wherein a modification of any one of a defined datapoint within the three-dimensional virtual model results in a modification of the three-dimensional simulation.

In a further embodiment, the method comprising performing an intermediate scan and generating a second three-dimensional model and modifying the simulation result based on the second three-dimensional model.

In a further embodiment, the method comprising generating at least a second data file that defines at least a second printable file to create at least a second aligner to move the at least one tooth from a first intermediate position to the goal final position.

In a further embodiment, the method further comprising wherein the occlusal table is set by identifying a mesial buccal cusp of the first molar in an upper set of teeth; identifying a buccal groove of the first molar in a lower set of teeth; and identifying on the occlusal table where the mesial buccal cusp of the upper first molar perpendicularly intersects the occlusal table and where the buccal groove of the lower first molar perpendicularly intersect the occlusal table.

In a further embodiment, the method wherein a molar bite class defines a left side and a right side sufficient to define a mechanics for each of the left side and the right side of either of the upper dental arch, the lower dental arch, or both.

In a further embodiment, the method comprising determining a center axis within the three-dimensional virtual model and wherein the center axis is used to calculate a relative tooth inclination.

In a further embodiment, the method wherein the mechanics provide for a rotation of the at least one tooth relative to the archform.

In a further embodiment, the method wherein the upper dental arch or the lower dental arch, or both comprise a plurality of teeth wherein each individual tooth is defined with regard to an angulation, inclination, and a final end tooth position with the simulation.

In a preferred embodiment, a method for forming an orthodontic aligner, said method comprising: (a) creating a three-dimensional virtual model of an upper dental arch, a lower dental arch, or both by obtaining data from an intraoral scan; (b) creating a composite image by combining the data from the intraoral scan with a cephalometric X-ray to define the composite image having bone structure and a first tooth position; (c) selecting from a set of rules an archform to maintain that corresponds to the first tooth position; (d) defining an end tooth position corresponding to the archform to maintain; (e) defining via the set of rules a movement pattern from the first tooth position to the end tooth position wherein movement of each tooth is limited to about 0.2 mm or 3° in a given stage; (f) defining at least one aligner sufficient to create the movement pattern from the first tooth position to an intermediate or the end tooth position; (g) wherein the aligner is defined to exert a therapeutic force on at least one tooth in a given stage; and (h) defining a printable file corresponding to at least one aligner.

In a preferred embodiment, a method for providing a result of an orthodontic realignment simulation comprising:

(a) obtaining a three-dimensional virtual model of an upper dental arch, lower dental arch, or both, the three-dimensional virtual model compiled from an intraoral scan of a mouth; (b) based on a shape of a modeled upper dental arch, a modeled lower dental arch, or both, selecting a matching predefined archform; (c) obtaining at least one of: (i) a first set of rules that define anterior and posterior molar movement; and/or (ii) a second set of rules that determine a path of tooth movement to the matching predefined archform; and/or (iii) a third set of rules that define a simulation mechanics for moving at least one tooth to a final position based on known endpoint data and the matching predefined archform; and (d) based on a result from implementing at least one of the first set of rules and/or second set of rules and/or the third set of rules, determining a final position of the at least one tooth in relation to the matching predefined archform.

In a preferred embodiment, a system for generating multiple orthodontic simulations comprising: (a) a computer for executing instructions, the computer having a processor, a memory, access to a data storage, and access to a display, wherein the data storage stores: (i) one or more predefined archforms; (ii) one or more predefined simulation mechanics; (iii) one or more predefined molar movement rules; (iv) at least one table of target ending positions for each tooth in a mouth, the target ending positions including at least one of: an angulation, an inclination, or a rotation; (v) a cephalogram; and (vi) a three-dimensional virtual model of an upper dental arch, a lower dental arch, or both wherein each dental arch comprises a plurality of teeth; and (b) wherein when executed the instructions: (i) identify a predefined archform that emulates the upper dental arch, the lower dental arch, or both; (ii) determine a molar bite class from the three-dimensional virtual model; (iii) use a determined molar bite class to identify at least one predefined simulation having simulation mechanics designed for the determined molar bite class; and (iv) determine an endpoint position for each tooth in the plurality of teeth, the endpoint positions based on a simulation mechanics scenario defined by an identified simulation, the predefined molar movement rules, an identified predefined archform, a table of target ending positions, a start position for each tooth in the plurality of teeth, and rules for tooth movement that prevent tooth collision while determining a path for each tooth in the plurality from its start position toward a corresponding target ending position that is aligned with the identified predefined archform.

In a further embodiment, the system further comprising displaying a result of the identified simulation.

In a further embodiment, the system wherein the result is matched with and overlaid on the cephalogram.

In a further embodiment, the system further comprising replacing the identified predefined archform with a compatible archform if simulation mechanics define expanding a dental arch.

In a further embodiment, the system wherein identifying at least one predefined simulation comprises identifying a predefined simulation having mechanics selected from the group consisting of: nonextraction, extraction, maintaining the identified predefined archform, replacing the identified predefined archform, performing IPR, extracting first premolars, extracting second premolars, distalization, adjusting for growth, correcting a posterior crossbite, postsurgery mechanics, and combinations thereof.

In a further embodiment, the system wherein the start position for each tooth comprises a measurement indicative of an inclination, an angulation, a rotation, or combinations thereof and the endpoint positions are based on skeletal class.

In a further embodiment, the system further comprising where using the determined molar bite class determines at least two different predefined simulations having mechanics designed for the determined molar bite class and determines the endpoint positions for each tooth according to the two different predefined simulations.

In a further embodiment, the system further comprising: defining an executable file manufacturing an orthodontic tray from the executable file.

In a further embodiment, the system sufficient to enact the method.

In a preferred embodiment, a simulated orthodontic treatment plan comprising: (a) a simulation scenario including molar movement rules that are based on predefined simulation mechanics, predefined endpoint positions, and a predefined molar bite class; (b) start positions for a molar obtained from a three-dimensional virtual model; (c) wherein simulation logic uses the molar movement rules, the predefined simulation mechanics, and the predefined endpoint position to incrementally move the molar from the start position to the end position and to align with a predetermined archform without collisions; and (d) obtaining a result of the simulation scenario on the three-dimensional virtual model.

In a further embodiment, the simulated orthodontic treatment plan further comprising: defining within the three-dimensional virtual model an occlusal table.

In a further embodiment, the simulated orthodontic treatment plan further comprising: defining within the three-dimensional virtual model a molar bite class.

In a further embodiment, the simulated orthodontic treatment plan further comprising: obtaining a WITS value from a cephalogram and using the WITS value to identify the predefined endpoint position for that WITS value.

In a further embodiment, the simulated orthodontic treatment plan wherein the endpoint position varies based on WITS value.

In a preferred embodiment, a system for generating at least one dental aligner for enacting an orthodontic movement simulation comprising: (a) an intraoral scanner, a computer, and a device suitable to generate an orthodontic tray; (b) the system performing a method comprising: (i) capturing a data set defining positions of oral structures via the intraoral scanner; (ii) storing within memory of the computer the data set and defining a three-dimensional virtual model of the oral structures and displaying the three-dimensional virtual model; (iii) laying a depiction of a selected predefined archform over the displayed three-dimensional virtual model to set an archform to maintain; (iv) obtaining a goal endpoint data; (v) defining a final tooth position of each of tooth based upon the selected predefined archform to maintain; (vi) obtaining a first set of rules that define at least a molar movement or a bicuspid movement to adjust at least one tooth to the archform to maintain; (vii) creating a series of stages wherein use of the first set of rules moves at least one of the molar movement or the bicuspid movement to adjust the position of at least one tooth to the archform to maintain; wherein an output of each stage within the series of stages is defined as an orthodontic aligner; and (viii) creating an executable file for said orthodontic aligner.

In a further embodiment, the system sufficient to enact the method.

In a preferred embodiment, an apparatus comprising: (a) a computer to execute instructions; (b) storage operatively connected to the computer, the storage storing: (i) data from an intraoral scan of one or more teeth; (ii) data relating to one or more predetermined archforms; (iii) predefined molar movements; (iv) predefined endpoint positions for tooth angulation, inclination, and rotation; (v) predefined simulation mechanics; (vi) a cephalogram; or (vii) combinations thereof; and (c) wherein executing instructions enables the computer to: (i) in response to receiving an archform selection from the one or more predetermined archforms and a molar bite classification from a model based on the intraoral scan, identify predefined simulation mechanics corresponding to the molar bite class, the simulation mechanics including molar movement rules for the simulation mechanics; (ii) use the molar movement mechanics rules for the simulation mechanics, calculate how much a molar selected from the intraoral scan needs to move and in what direction to align with the selected archform; and (iii) use endpoint data for the simulation mechanics, determine a final molar position.

In a further embodiment, the apparatus further comprising: a screen operatively connected to the computer, the screen to display a simulation of the results of molar movement.

In a further embodiment, the apparatus sufficient to overcorrect the rotation of the tooth in order to counteract the limitations of plastic inefficiency of the aligner.

BRIEF DESCRIPTION OF THE FIGURES

FIG. 4B is a cephalogram defining the tooth's central axis.

FIG. 5 a flowchart depicting the logic regarding the occlusal table, the central axis, inclination, and angulation.

FIG. 8 is a flowchart of the logic determining molar bite classification.

FIG. 16 is a flowchart of overlaying data on a cephalogram.

DETAILED DESCRIPTION OF THE INVENTION

Definitions

Figure 1:
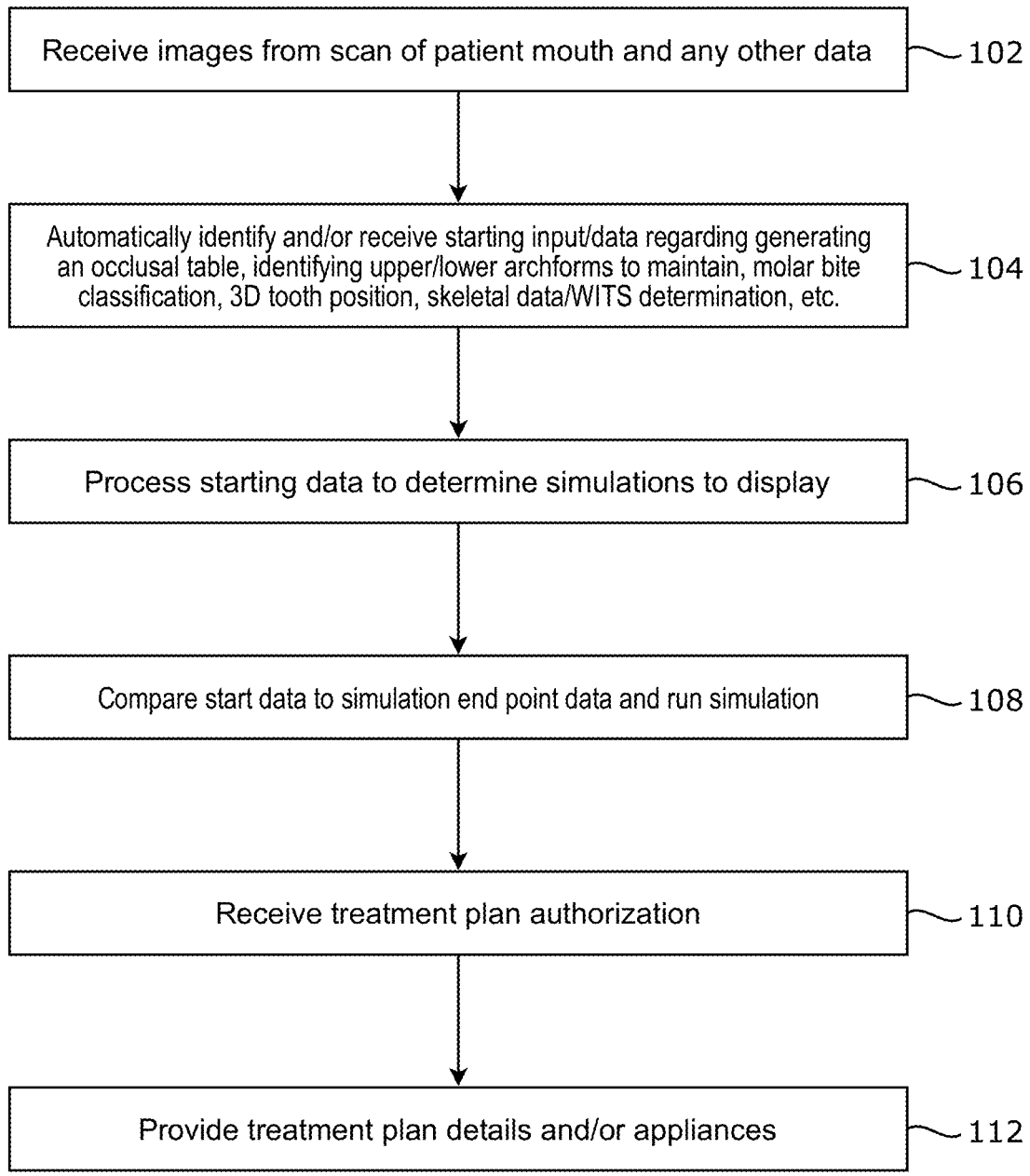
FIG. 1 is an overview flowchart of an orthodontic simulation.

Various embodiments are described more fully hereinafter with reference to the accompanying drawings, which form a part hereof, and which show, by way of illustration, specific exemplary embodiments by which the innovations may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media, devices, or any similar or equivalent arrangements known to those skilled in the art. Accordingly, the various embodiments may take the form of an entirely hardware embodiment, an entirely software embodiment or an embodiment combining software and hardware aspects. The following detailed description is, therefore, not to be taken in a limiting sense.

As used in this application, the words "a," "an," and "one" are defined to include one or more of the referenced items unless specifically stated otherwise. The terms "approximately" and "about" are defined to mean ±10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

As used herein, the below terms will have the following meanings as may be supplemented elsewhere in this specification:

ALIGNER: An orthodontic appliance that is molded to fit over the teeth and is used to correct their alignment.

APPLIANCE: Any device designed to influence the shape and/or function of the stomatognathic system.

ARCH: Collectively, the teeth of either jaw, i.e., the term maxillary arch would include all teeth in the maxillary arch.

ARCHFORM: The geometric shape of the dental arch or of an archwire when viewed in the horizontal plane (e.g., square, tapered, ovoid).

BUCCAL: Toward the cheeks.

CEPHALOMETRIC ANALYSIS: The process of evaluating dental and skeletal relationships by way of measurements obtained directly from the living head or, more commonly, from cephalometric radiographs and tracings. Refers also to the standardized sets of cephalometric measurements (e.g., Downs Analysis) commonly used in the evaluation.

CEPHALOMETRIC LANDMARKS: Points on a cephalometric radiograph or tracing representing certain hard or soft tissue anatomical structures (anatomical landmarks) or intersections of lines (constructed landmarks).

CEPHALOMETRIC RADIOGRAPH: A standardized radiograph of the head characterized by a precisely defined relationship among X-ray source, subject and film.

CEPHALOMETRIC TRACING: A tracing of salient cephalometric structures, landmarks and pertinent measurements, which is used for diagnostic purposes.

CONDYLE: The rounded cartilage and bone articulating element of the mandible. The superior portion of the ramus that articulates with the temporal eminence in the glenoid fossa.

CONDYLION (Co): A cephalometric landmark. The most superior and distal point on the head of the condyle.

CROSSBITE: An abnormal relationship of a tooth or teeth to the opposing teeth, in which normal buccolingual or labiolingual relationships are reversed.

CROWDING: Dental malalignment caused by inadequate space for the teeth.

DISTAL: A direction oriented along the dental arch away from the dental midline; right or left in the anterior segment posteriorly in the buccal segments.

DISTALIZATION: The process of moving teeth distally in an arch.

GNATHION (GN): A cephalometric landmark: The point on the anterior cymphasis closest to the intersection of N-Po line and the inferior border of the mandible.

INCISAL: Pertaining to the cutting edge of the anterior teeth.

INCLINATION: The angle of the long axis of a tooth from a particular line of reference; the tilt or tip of a tooth.

LABIAL: Of or pertaining to the lip. A term that describes a tooth surface facing the lips. Has the same meaning as 'facial' in the anterior portion of the dentofacial complex.

LEVELING: A phase of comprehensive orthodontic treatment when fixed appliances are used to change the line of intercuspation from a curve to a straight line; to align the teeth in the same plane.

LINGUAL: Of or pertaining to the tongue. A term used to describe surfaces and directions toward the tongue.

MALOCCLUSION: Of relationship of teeth in occlusion, a deviation in intramaxillary and/or intermaxillary relations of teeth from normal occlusion. Often associated with other dentofacial deformities (see Angle classification).

MANDIBLE: The lower jaw.

MAXILLARY: Of or pertaining to the upper jaw. May be used to describe teeth, dental restorations, orthodontic appliances or facial structures.

MESIAL: Toward or facing the midline, following the dental arch. Used to describe surfaces of teeth, as well as direction.

OCCLUSAL: Pertaining to the chewing surfaces of the posterior teeth. May be used to identify those tooth surfaces, as well as the direction (upward in the lower arch, downward in the upper).

OCCLUSAL PLANE: Intersection of cusp tips of upper and lower first molars, bisection of incisors, overbite, or open bite (a cant of the occlusal plane results when molars are at a more superior position, right vs. left). One of the five planes used in the McGann cephalometric analysis.

OCCLUSION: The relationship of the maxillary and mandibular teeth as they are brought into functional contact.

OPEN BITE: Lack of tooth contact in an occluding position.

OVERBITE: Vertical overlap of maxillary teeth over mandibular anterior teeth, usually measured perpendicular to the occlusal plane.

OVERJET: Horizontal projection of maxillary teeth beyond the mandibular anterior teeth, usually measured parallel to the occlusal plane. When not otherwise specified, the term is generally assumed to refer to central incisors and is measured from the labial surface of the mandibular tooth to the lingual surface of the maxillary at the level of the edge of the upper incisor. Unique conditions may sometimes require other measuring techniques.

RETRACTION: Retracting teeth refers to moving teeth back, as is done in extraction cases (the opposite of "advancement").

ROOT: That part of the tooth not covered by enamel. It normally lies within the alveolus where it is attached to the bone by the periodontal membrane (ligament).

ROOT MOVEMENT: The transverse tooth movement characterized by little displacement of the crown and the center of rotation located on the long axis and at or near bracket level.

ROTATION: Can occur around any axis. Orthodontic rotation usually refers to motion around the long axis of the tooth.

TORQUE: A third order couple that moves the crown in one direction and the root in the opposite direction.

WITS: A, B, perpendicular A cephalometric measurement used to determine skeletal class, more reliable for class III. Distance in mm between a vertical line drawn at a right angle from the A point (on the cephalogram) to the occlusal plane and the B point to the occlusal plane. When the A point is in front, the number is positive; if the B point is in front then the number is negative.

Additional terms used herein are defined as follows:

DATA/INFORMATION: Facts, figures, measurements, etc.

DIGITAL/VIRTUAL: Computerized, online, digitized, not physical.

SIMULATION: Computerized modeling of a behavior and/or object.

SOFTWARE: Instructions that can be executed by a computer

Current practice for straightening teeth using dental aligners is to conform all malocclusions to a single ideal finish regardless of the specific issues and physiologic constraints present in a particular case. The goal is for each and every patient to have the same perfect smile. In most cases it may take time for the patient to receive an aligner because data is exported from one office to another office where a human stager sends back a first proposal. The first office either agrees or disagrees with the first proposal; agreement is the exception and not the norm. As such, the first proposal is sent back to the human stager for another attempt at devising an acceptable aligner. There can be many such iterations of back and forth before an aligner is approved for printing. The back and forth between various people, some of which may not even be dental professional, add inaccuracies, time, and cost making many of these treatment options unavailable due to cost. Aside from cost people are not invariable; each case may be slightly different, which in turn can increase inaccuracies in the approved appliance, increase time for creating the approved appliance, or both.

The present disclosure overcomes these and other deficiencies by providing an integrated method embodied in software deploying the logic for use with a computer for rapid, efficient, and accurate determination of orthodontic treatment plans that can be visualized by the practitioner, patient or both so that a particular treatment plan can be selected at the outset before commitment to the plan based on a realistic depiction of the outcome of one or more treatment plans that are suitable for the particular patient. Additionally, if the office is equipped with a 3D printer, one or more aligners may be immediately printed so treatment can begin that day. Otherwise, instructions may be provided to other facilities skilled in 3D aligner printing for fulfillment without undue delay. In addition to reducing cost and time, the three-dimensional characterization of each tooth in a given patient's mouth coupled with rules regarding allowable simulated molar movement for the patient's determined molar bite class and/or skeletal structure per a particular simulation scenario give the practitioner and the patient the ability to visualize what can realistically be achieved for that patient under orthodontic procedures. The patient's own body determines what is possible for that patient and he/she is not forced to accept a one-size supposedly fits all smile.

As disclosed herein, and as will be further detailed by the disclosure, figures, and tables, a three-dimensional virtual model of a patient's mouth is analyzed to determine the starting position of each tooth according to three different axis (i.e., x, y, and z) and how each tooth relates to the others. Using detectable features of the three-dimensional virtual model of the upper dental arch, the lower dental arch, or both, wherein the virtual model of the upper or lower dental arches provides a visual model of teeth and/or additional oral structures within the three-dimensional model, including the occlusal table for that patient. The occlusal table is used for reference when analyzing possible tooth repositioning per repositioning rules. Another reference used when analyzing possible tooth repositioning, is an archform that is selected from predefined archforms where the selected archform conforms to the patient's natural dental arch. Archforms are selected for both upper and lower dental arches. Further, data is obtained from a cephalogram to determine in which skeletal class a particular patient resides. Taking start position data, logic determines the possible movements of each tooth per universal rules and/or simulation specific rules to determine how that patient's teeth can be moved toward final endpoint positions that are predefined by endpoint tables corresponding to simulation specifics, skeletal structure, or both. The patient can view all of the simulations that are possible for his/her measurements and prescribed endpoint positions to determine which result appeals to that patient. The entire simulated movement can be displayed or just the end results. Either way, the practitioner and patient have a modular plan in hand including timelines, appliances needed, and other details by the time the office visit has finished.

To better understand the disclosure herein, relevant figures are referenced to provide nonlimiting examples that may be embraced by one or more embodiments described herein. As such, referring to FIG. 1, which is a high-level overview (100) of how various orthodontic simulations may be generated for display. Generally, the practitioner scans the oral cavity of a patient's mouth to obtain detailed images. These images can be stitched together to create three-dimensional, virtual representations that are fully accurate digital/virtual reproductions of what was scanned. The practitioner then selects one or more three-dimensional images to import into the simulation logic (102). The practitioner may also import other data into the simulation logic such as X-rays and photos of the patient (102). Using the imported information, the simulation logic can autodetect the three-dimensional position of each tooth present in a patient's mouth (104). The simulation logic can also autodetect/receive skeletal information from X-rays, photos, etc. (104) and process data (106) to determine which simulation/set of simulations to display and/or just the ending result (108). Based on the simulation selected (approved) by the patient/practitioner (110) the details (112) of the selected/approved simulation/treatment plan are presented such as by display, print, saved to a file, etc. Data received, generated, calculated, etc. can be stored and retrieved on demand. The simulation, which being saved to a file, may be a printable file, that can be executed on a three-dimensional printer, such as those which print using certain plastic materials, and which can then print a single orthodontic aligner (tray) or a series of aligners which can be used in sequential order by a patient to produce the effects of the orthodontic simulation. Alternatively, the simulation and/or related files can be sent to a third party to create aligners.

Figure 2:
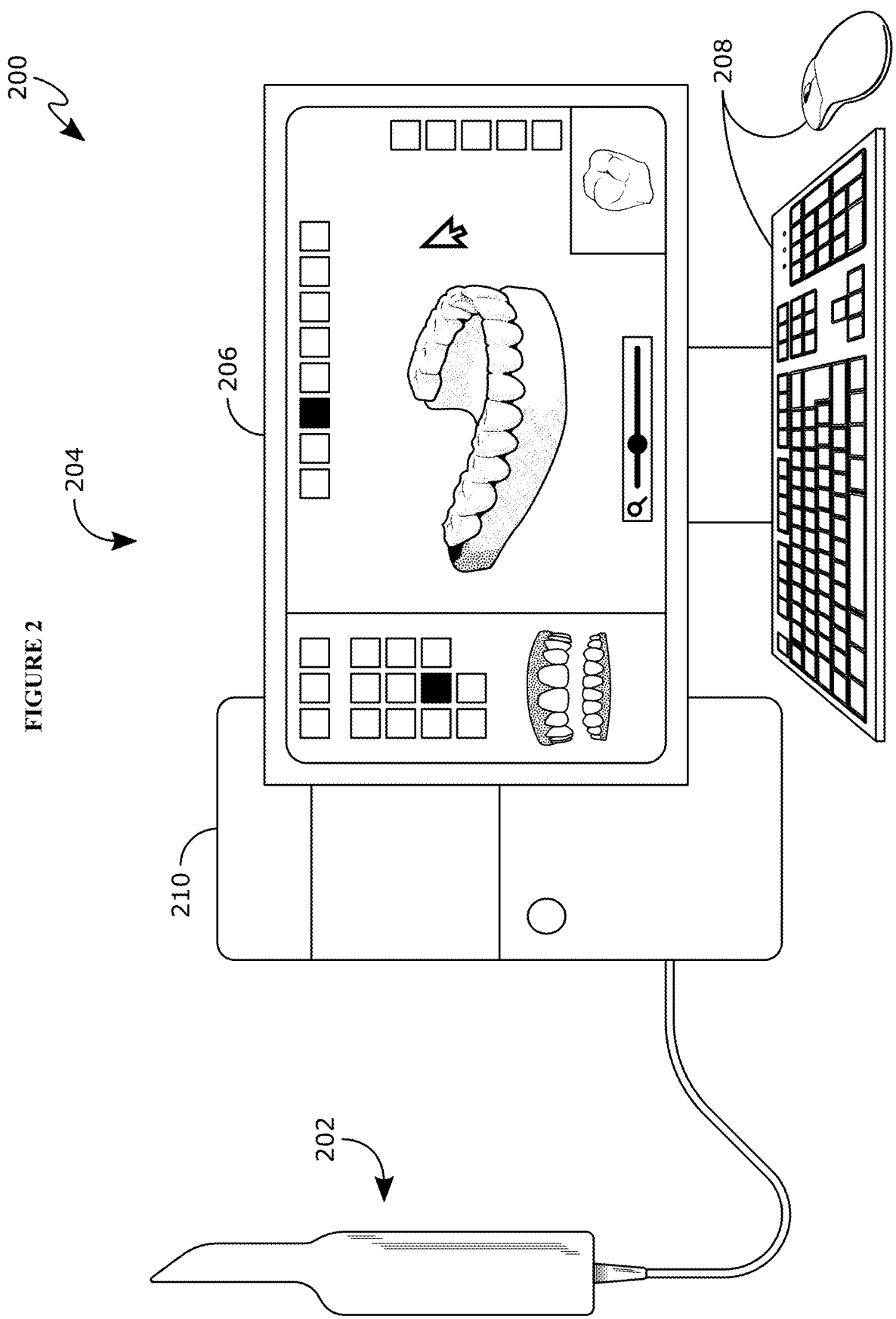
FIG. 2 depicts an embodiment of a system for generating three-dimensional orthodontic simulations.

FIG. 2 depicts an example of a system (200) for implementing an embodiment of the disclosure. The system (200) can include an intraoral scanning device (202), such as those manufactured by Medit, that takes a series of images that are combined together to give a three-dimensional view of the mouth, featuring the upper dental arch, the lower dental arch, which displays the teeth, and typically the gums, and the palate. One or more scanned three-dimensional images may be saved on a computer (204), the cloud (not shown), a server (not shown) displayed (206) or combinations thereof. The computer (204) may include one or more input devices (208), processor, memory, internal storage (collectively shown within [210]), connection to the Internet. Embodiments may also include cloud/Web-based processing and storage capabilities. For best simulation visualization, the computer (local, Web, cloud) should be enabled to handle data processing, graphics, etc. for running the simulation software which executes the logic.

Generally, the intraoral scanner (202) takes a plurality of images that are combined or stitched together and saved within a file of the upper and lower dental arch including images of the corresponding teeth. The file can then be accessed and opened by software designed to visualize the image. Images selected for use in simulation logic allow for orienting the images in a variety of manners, including to zoom in or out, and to rotate the image as well as inverting the image as desired. Display of these images, however, is not necessary for the simulation logic to autodetect the three-dimensional starting positions for a tooth.

One advantage disclosed herein is the ability for the software logic to automatically identify tooth and/or mouth structures and use these structures to calculate certain measurements, which are used for simulating tooth realignment from their starting point to one or more endpoints. A series of rules then govern the movement of the teeth from their starting point, through one or more intermediate points, and to one or more endpoints. One image that may be generated by the software logic, imported into the software logic, or both is an image showing the teeth that are present in the patient's mouth. Although discussion herein refers to a full set of adult teeth, embodiments are not limited thereto. In reality, the software logic can identify/receive input regarding any number of teeth including primary and permanent teeth. Simulations are programmed to be able to accommodate numerous starting scenarios relating to the number and condition of the patient's teeth.

Figure 3A:
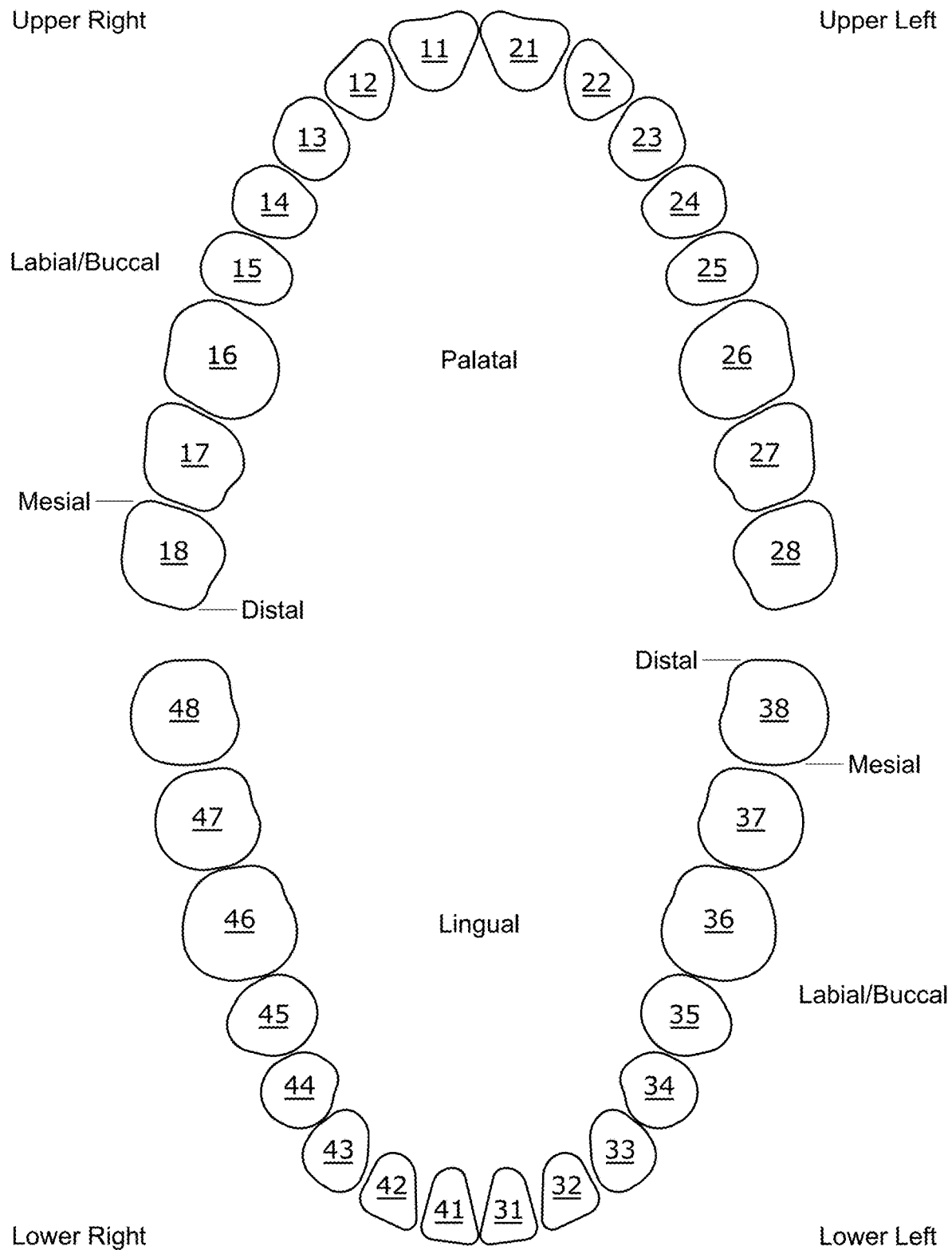
FIG. 3A is a standard tooth numbering chart using a Fédération Dentaire Internationale (FDI) based notation system.
Figure 3B:
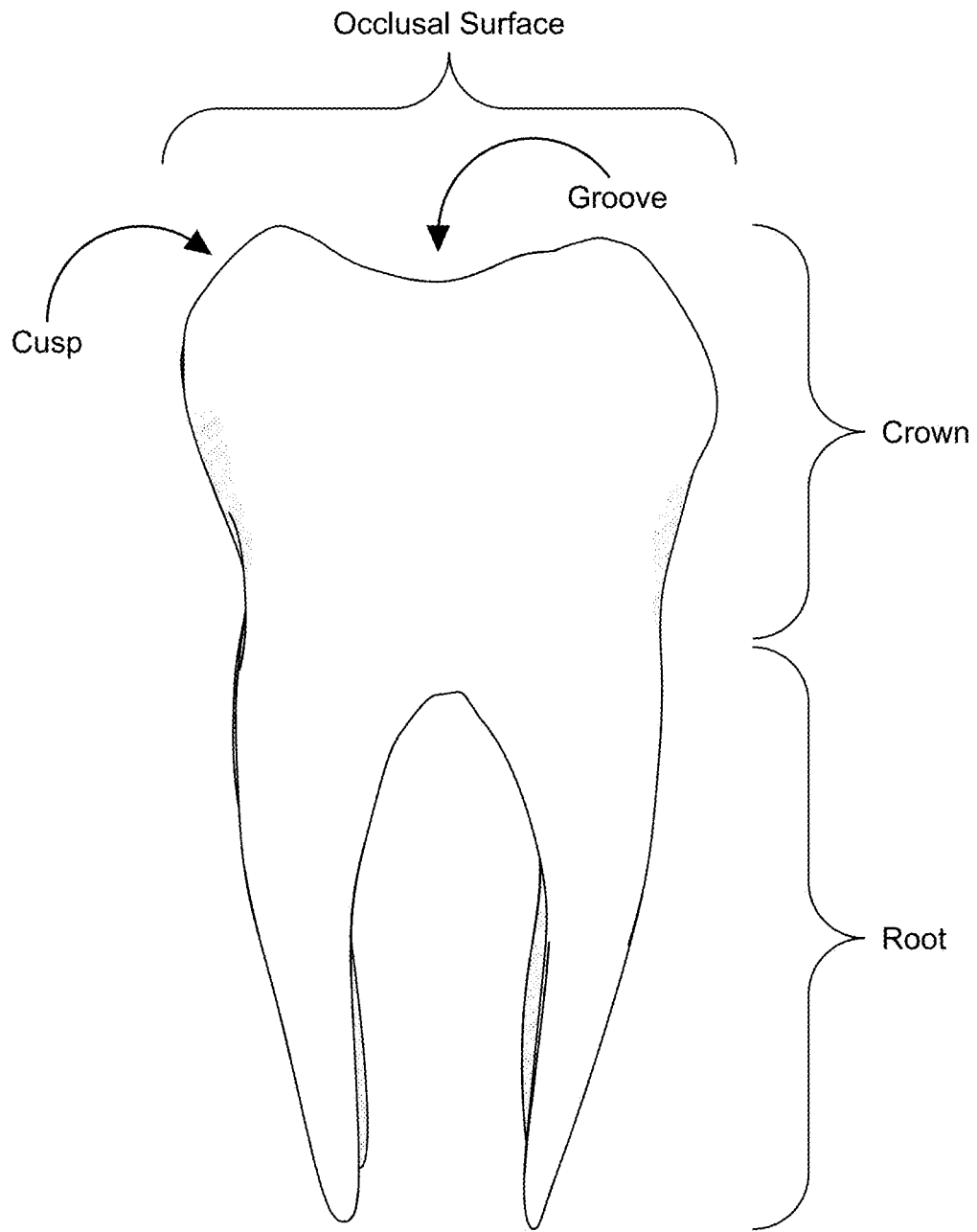
FIG. 3B is a depiction of tooth surfaces.

FIG. 3A represents an image of a patient's teeth information using a Fédération Dentaire Internationale (FDI) based notation system. For example, teeth are divided into four quadrants; the first quadrant corresponding to the upper right of the mouth, the second quadrant the upper left of the mouth, the third quadrant the lower left of the mouth and the fourth quadrant the lower right of the mouth. Thus, in a two number identification system, the first number indicates the quadrant in which the tooth is located. The second number in the two number system identifies the type of tooth; 1 corresponds to central incisors, 2 corresponds to lateral incisors, 3 corresponds to canines/cuspids, 4 corresponds to the first premolar/bicuspids, 5 corresponds to second premolars/bicuspids, 6 corresponds to first molars, 7 corresponds to second molars and 8 corresponds to third molars or "wisdom teeth." Thus, each number in the FDI numbering system identifies the quadrant (1-4) and the type (1-8) of the tooth. For instance, 11, 21, 31, and 41 correspond to all four central incisors whereas 18, 28, 38, and 48 correspond to all four wisdom teeth (in some instances the numbers are also separated by a period, such as 1.1, or 2.1, etc., as known to those of ordinary skill in the art). Also labeled in FIG. 3A are directional terms. For example, the terms "palatal" and "lingual" are used to identify the surfaces of the teeth that face, or should face, the palate or the tongue or in that direction. The term "lingual" is often used to designate both palatal and lingual directionality, surfaces of the teeth, or both. The opposite surfaces/directions indicated as "labial" (lip) or "buccal" (cheek). Again, these terms may be used interchangeably to describe the direction of toward the lip/cheek, facing the lip/cheek, or the like. A midline, such as the vertical line (434) in FIG. 4A, may be envisioned between central incisors splitting the teeth/mouth into left and right sides. The mesial direction/surface or the like is toward the midline whereas the distal directions/surface or the like is further away from the midline. Additional tooth structures, surfaces, features, directionality, and the like are described in the definitions and/or other sections of this disclosure, some of which are further identified in FIGS. 3B-3G, specifically FIG. 3B labels the various parts of the tooth, namely the occlusal surface, the cusp, the groove, the crown and the root.

Figure 3C:
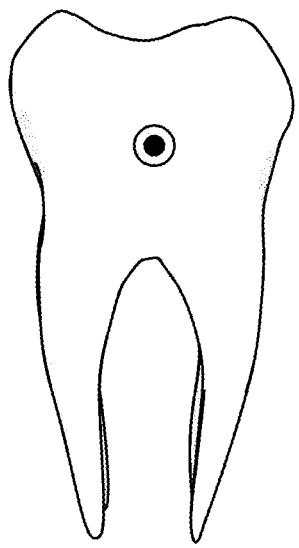
FIGS. 3C-3G depict different orientations of tooth surfaces.
Figure 3D:
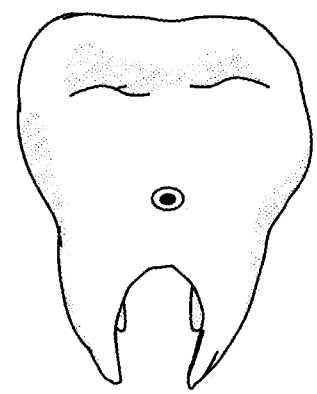
Figure 3E:
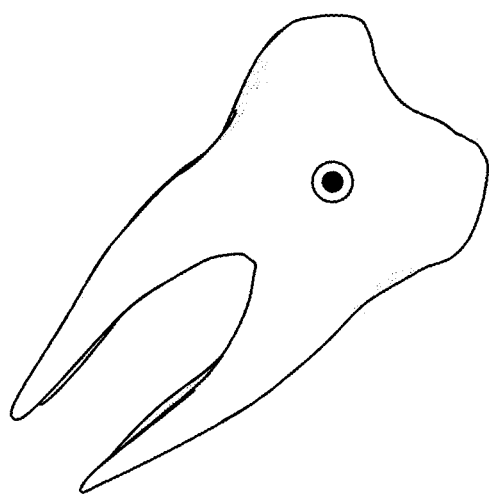
Figure 3F:
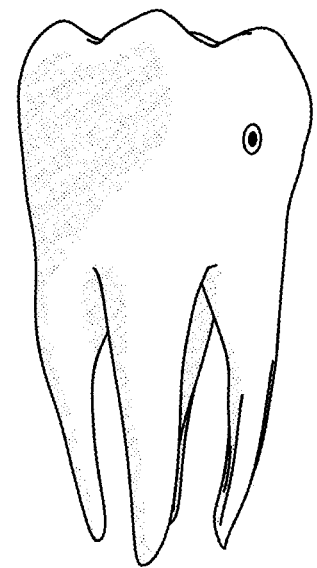
Figure 3G:
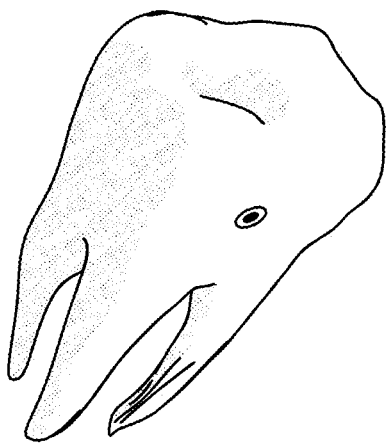
Figure 4A:
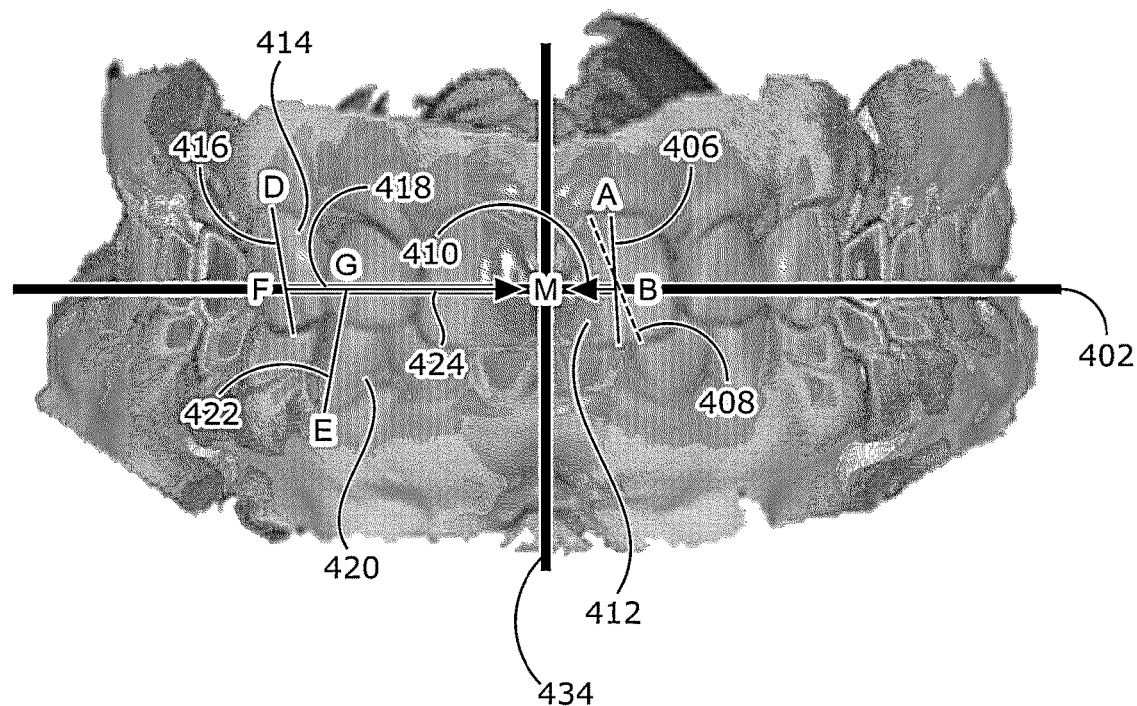
FIGS. 4A and 4B are cephalographic images depicting figures that are detected in the orthodontic simulations.

The software logic can identify the three-dimensional starting position of each tooth in the scan. Precise identification of tooth starting position allows the software logic to determine, using rules, and endpoint position values, how the teeth will realign during the simulation, therefore allowing appliances, such as aligners, brackets, or a combination thereof, to enact the orthodontic movement of the simulation. There are three different positions of note: inclination, alignment, and rotation. Referring to FIG. 3C, a three-dimensional molar is shown in a "neutral" position, with the occlusal surface facing up. As such, the bullet (dot) on the tooth faces lingually, the right side mesially, and the left side distally. FIG. 3D demonstrates tooth inclination. In this case, the inclination is lingual, or toward the tongue. FIG. 3E demonstrates tooth angulation or tipping. In this case, tipping or angulation is mesial, toward the midline. FIG. 3F demonstrates tooth rotation, which can be in the mesial or distal. FIG. 3G demonstrates simultaneous inclination, angulation, and rotation.

At the start of an office visit, after a three-dimensional model/scan of the patient's teeth is available to simulation logic, it will analyze the model to determine the starting inclination, angulation, and rotation positions of each tooth in the model using the collection of data input into the system. Broadly, simulation logic uses each of the starting angulation, inclination, and rotation measurements and predefined ending angulation, inclination, and rotation measurements (for each tooth) and determines the difference therebetween. Known differences between start and desired endpoint positioning is used by the logic when determining a path toward the end result. This movement can be depicted in a simulation, which can be visually enacted on the display. Notably, the start of treatment may be before any treatment has occurred or at any stage during treatment such as during a progress check, which is an intermediate position. In such a progress check, a new scan, or other new data is captured and forms a new tooth start position. This can be compared to a predefined goal target position at the given stage of the treatment, or can be used independently to simply plan the subsequent step and movement within the orthodontic simulation.

Each of the inclination and angulation measurements are angles, measured in degrees. Generally, to determine inclination and angulation, the logic measures angles between the center axis of a tooth and the occlusal table. Inclination refers to the degree to which a tooth is inclined labially/buccally or lingually/toward the palate (e.g., FIG. 3D). Thus, the relevant angle in determining inclination is between the central axis and occlusal table in the lingual/palatal direction. The relevant angle in determining angulation is between the center axis and the occlusal table toward the midline on the labial/buccal side of the tooth. A tooth's angulation designates the degree to which a tooth in angled mesially or distally (e.g., FIG. 3E) relative to the occlusal table.

Figure 4B:
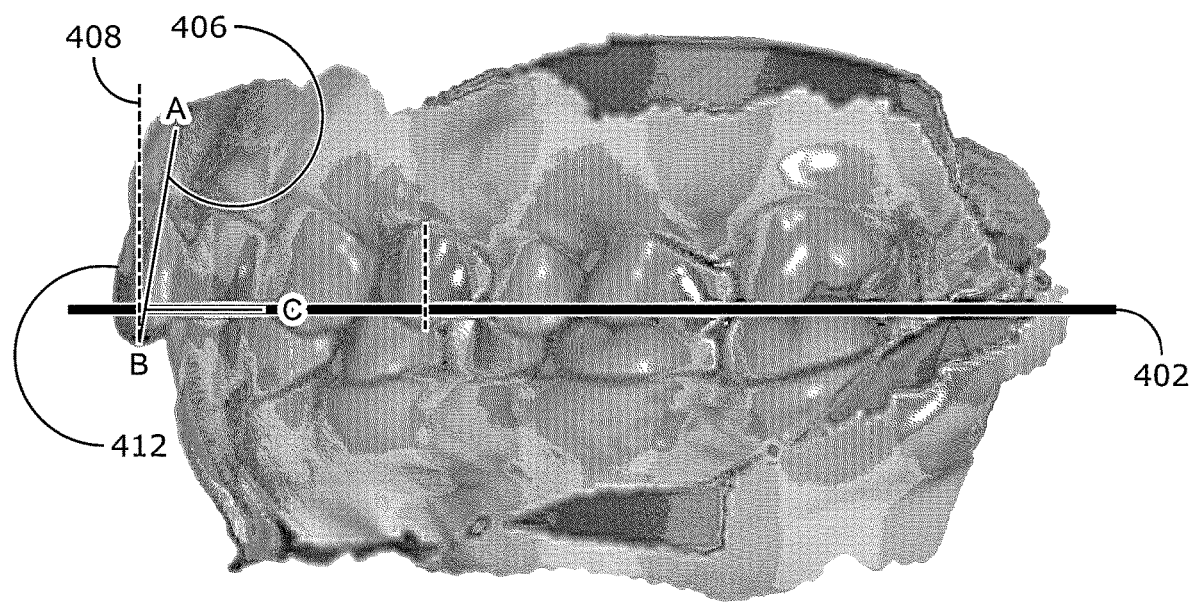
Figure 4C:
FIG. 4C is a cephalogram showing a central axis from the tip of a buccal cusp to the CG point.

Thus, to determine inclination and angulation, the logic determines the central/center axis of each tooth and the plane of the patient's occlusal table. Referring first to the central axis, logic may auto detect/identify the center axis of each tooth, or it may, manually drawn or adjusted (e.g., virtually on the scan of the oral cavity), or both. Using a central incisor (412) of FIGS. 4A and 4B as an example, the tooth's central axis is shown at line A-B (406) in FIGS. 4A and 4B, which extends from the incisal edge through the three-dimensional center of the tooth to the root (not shown). Alternatively, the center axis may be represented by a line extending from the incisal edge or buccal cusp to the crown-gingival (CG) point such as the dotted line (404) on the first premolar shown in FIG. 4B. As yet another alternative, the center axis of certain teeth may be identified as being parallel to the mesial edge/side of the tooth. This alternative may be employed at least when teeth are crowded or in other instances where tooth anatomy is difficult for the software logic to detect. It should be noted that the lines and other markings in the figures that were generated by software logic are not necessarily needed for logic to perform the detection, calculation, or the like. Lines and other markings are depicted to assist in understanding how the logic performs. Nonetheless, an embodiment enables display of the result of the determination such as positioning of the central axis of each tooth. Display of logic results may then be altered by the practitioner such as by moving one or both ends of a line.

Figure 4D:
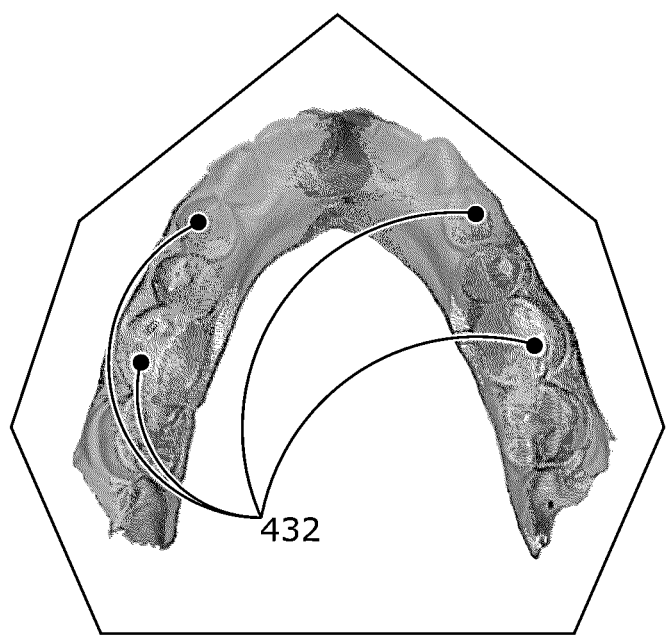
FIG. 4D is a cephalogram showing four points defining the occlusal table.

The other reference for determining the degree of inclination and angulation of a tooth is the occlusal table. In an embodiment the occlusal table is auto identified and in another embodiment the occlusal table is generated based on data input from the practitioner using a process (500) detailed in FIG. 5. Either way, the occlusal table is set by identifying three to four points ([432] from FIG. 4D) on lower occlusal surfaces. For example, when using three points, one point is the incisal edge of central incisors at the midline, and the other two points are on the distal, buccal cusps of each opposing first molar. When preferably using four points, the two points on each of the distal, buccal cusps are still used, but instead of the single incisal point, two points are identified on the buccal/labial cusps of each first premolars (502). The four points (432) defining the occlusal table are shown in FIG. 4D. Still referring to FIG. 5 and FIG. 4D, the occlusal table is leveled at the four (or three) reference points (504). When viewed from the front or the side, the occlusal table rests on the tips of the cusps of the four lower occlusal table reference teeth (506). Initially, the remainder of the lower teeth may be above, below, or at the occlusal table.

Referring now to FIG. 5 and FIGS. 4A, 4B, and 4C together, and still using an upper central incisor as an example, the starting inclination for the incisor can be determined by measuring the angle created by intersecting lines A-B (incisor center axis) and B-C (lingual/palatal side of occlusal table). See, e.g., FIG. 5 at steps (508) and (510).

In the same way, the inclination of each tooth (upper and lower) may be auto determined. See, e.g., FIG. 5 at steps (508) and (510). A representation of the central axis and not the actual central axis may be used to determine tooth inclination. In an embodiment, the central axis may be represented by a virtual line from a tip of a buccal cusp to the CG point. Preferably, however, the actual center axis of each tooth, including molars, may be identified as is shown by the dotted lines (404) in FIG. 4C. Either way, the angle created by the lingual intersection of a tooth's central axis (or representation thereof) and the occlusal table (e.g., horizontal solid line [402] in FIG. 4C) can be electronically determined and saved as a start point inclination for each tooth identified in the scan.

Tooth angulation (e.g., "tipping") is also determined by the logic as an angle between the tooth center axis and the occlusal table. Angulation, however, is indicative of whether the crown of a tooth is "tipped" mesially (toward the midline) or distally (away from the midline) (e.g., FIG. 3E). For example, in FIG. 4A, the solid line A-B (406) represents the center axis of the incisor as it is in the image. But if the tooth were angled ("tipped"), the center axis could be as indicated by the dotted line (408). Thus, angles created by the intersection of the center axis of a tooth and the occlusal table on the labial/buccal side of the teeth and in the direction of the arrow, toward the midline (434), are indicative of tooth angulation. In the example shown in FIG. 4A, angulation of central incisor 21 (412) is calculated as the angle created by the intersection of lines A-B (406) and B-M (410). As another example, the angulation of canine 13 (414) is the measure of the angle created by lines D-F (416) and F-G (418). Similarly, the angulation of canine 43 (420) is the (digital) measurement of the angle created by lines E-G (422) and G-M (424). The center axis of molars may also be determined from by a line extending from the mesial buccal cusp near the central groove to the gingival-crown curvature so that the tooth is "halved." The angulation may be measured from the occlusal table to the line on the mesial side. Alternatively, the starting angulation of molars may be determined using a line from the mesial marginal ridge to the distal marginal ridge instead of the central axis.

Figure 6:
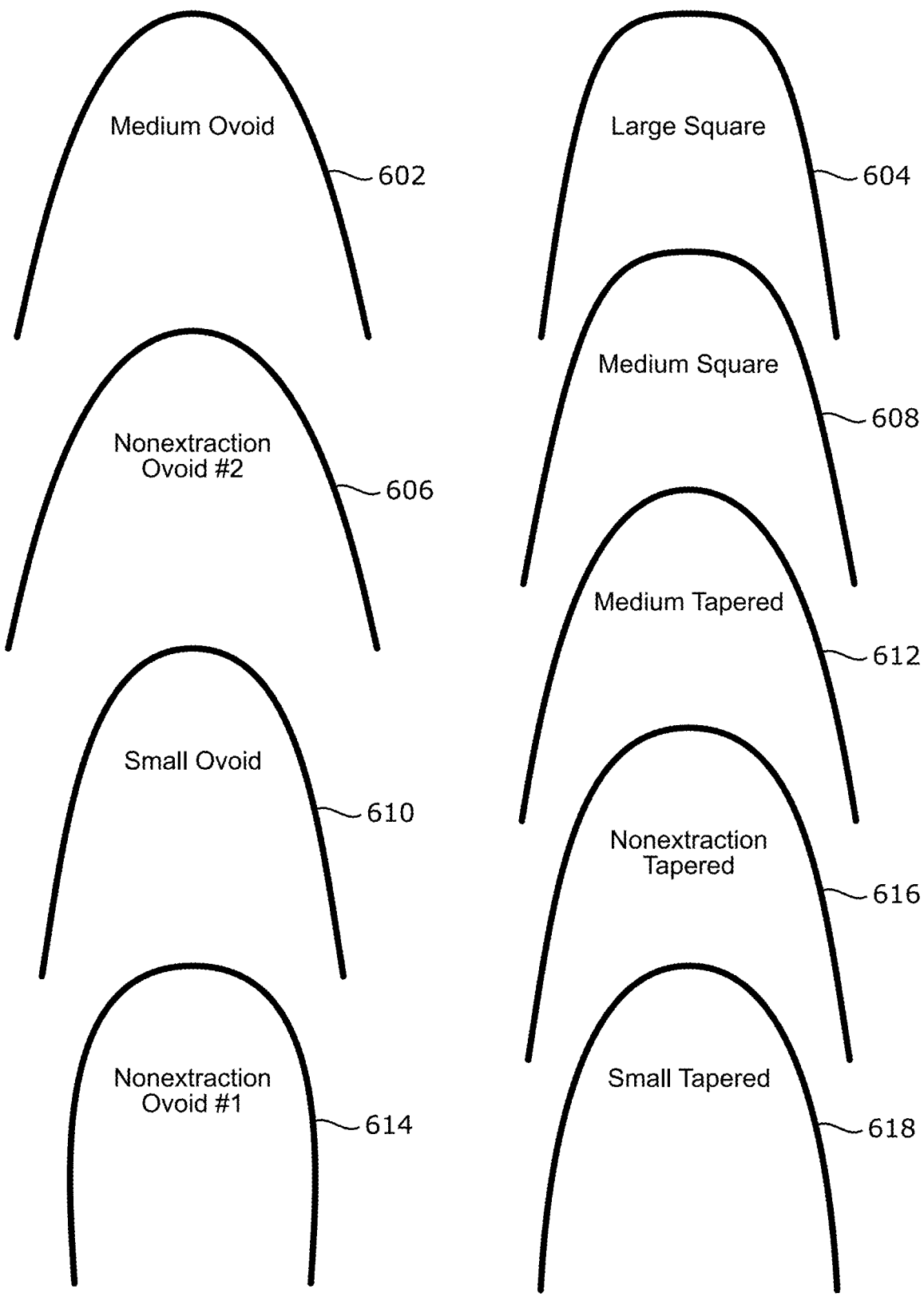
FIG. 6 depicts the nine predefined archforms.

Tooth rotation is relative to an archform that is selected to best match the natural arch formed the patient's teeth. In an embodiment, during start position identification, a default archform is aligned with the incisors so that the center of the arch is at the midline. An archform is so aligned for both the upper teeth and the lower teeth. If the practitioner desires, he/she can move the archform by dragging and dropping into a desired position. Dragging and dropping includes the ability to rotate the archform to conform to the patient's natural archform. If the practitioner also desires, he/she can select a different predetermined archform shape. Although nine predetermined archforms are shown in FIG. 6, embodiments may include additional predetermined archforms. The same archform shapes shown in FIG. 6 may be utilized for both upper and lower teeth. In an embodiment, the default archform for upper and lower jaws is the "medium ovoid" archform (602). In an embodiment, the software logic determines the "best fit" archform for the natural curvature of the patient's upper and lower teeth and displays the "best fit" as the default archform. Either way, if the default archforms are not changed by selecting a different option, the default archforms are set as the "archform to maintain" during simulation. If, however, the practitioner selects a different embodiment of an archform (upper, lower, both) the last archform selected will be the archform to maintain. In an embodiment, the practitioner actively approves the archform to maintain for simulation before going on to the next step. The predetermined archforms that can be selected to maintain are: medium ovoid (602), nonextraction ovoid #1 (614), nonextraction ovoid #2 (606), small ovoid (610), large square (604), medium square (608), medium tapered (612), nonextraction tapered (616), and small tapered (618), which are shown in FIG. 6. The predetermined archforms are based on extensive review of actual patient data to determine the most common natural arch curvatures and sizes. Matching a simulation archform to the bone structure of each patient (e.g., size and shape of bone and jaw) creates a simulation of a stable result. In other words, each person has a dental arch that is normal for that person that harmonizes with other facial features and bone structure. Using a predefined archform shape throughout a simulation scenario ensures that harmonization is retained from beginning to end. Stated another way, the logic has a consistent refence (e.g., archform to maintain) in the predefined archform such that logic does not alter the archform in an effort to create space unless specific directed to do so. As such, the end result that the patient observes is a stable outcome for that patient's physiology. Current practice does not consider an archform shape or size, which may result in an expectation that cannot be realistically achieved, is unstable and will revert over time, or both. Thus, there is more than one technical benefit to utilizing predefined archforms including having a consistent reference for logic to determine starting teeth positions, endpoint positioning, facial harmony, and realistic, stable demonstrations of what the patient can expect per a specific treatment plan. Further, using the preset references simplifies determining acceptable tooth advancement toward finished alignment and allows the logic to determine a particular outcome based on the selected archform to maintain. The logic uses whichever archform is selected to maintain at this point to determine how all of the teeth should move to that selected archform. Per preset rules, logic moves teeth to the preset archform, parallel or rotated thereto as required by preset endpoints and at defined inclinations and angulations. Having a preset archform options also enables logic to replace the selected archform for a different archform that is consistent/compatible with the patient's facial structure should the protocol call for it. The endpoint arch formation is known to the logic, which allows recalibration to the different archform for a different potential result. Current practices do not use predetermined archforms to use as a reference for beginning and endpoint positioning and alignment. Doing so simplifies the process so that logic can determine where every tooth will be in space at any given time. This amount of predictability allows logic to switch archforms (if called for) and change movement mechanics for a different result. Without the preset archform, end results would not be as accurate or predictable and the movement mechanics needed and sequences of movement would not be as easily determined. Thus, a technical advantage per this disclosure simplifies processing options by having a set of predefined archforms to reference for feasible simulation results. Since the archforms are predefined, switching from one to another is relatively easy as it is another known endpoint.

Tooth rotation is calculated as the degrees of rotation (e.g., FIG. 3F) with respect to the selected archform to maintain. Simulation scenarios generally correct rotation by bringing teeth to straight with respect to the reference archform. There is some leeway with what is considered as straight; in some embodiments, ±about two degrees may be acceptable. Furthermore, many simulation scenarios also overcorrect rotation and leave the tooth in the overcorrected rotational position. Overcorrection, if any, is sometimes, indicated for molars. Nevertheless, correcting rotation and other positioning issues begins with accurate determination of tooth starting position.

Figure 4E:
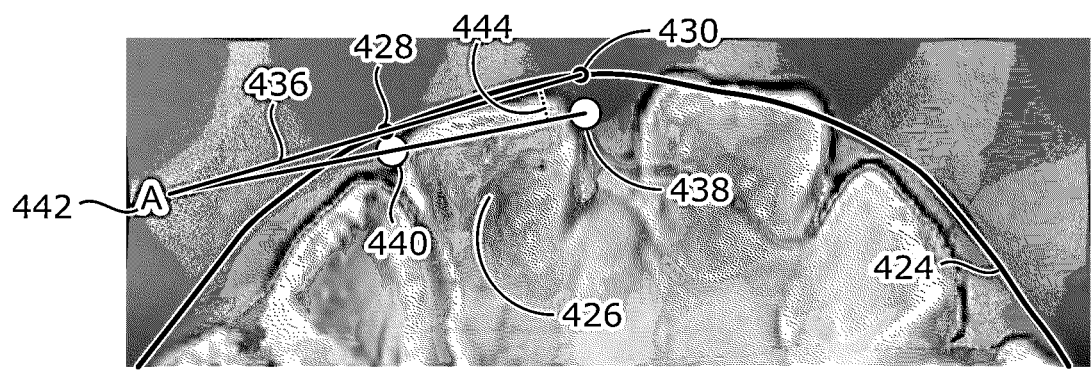
FIG. 4E is a cephalogram defining a reference archform on the labial side of the incisors.
Figure 7:
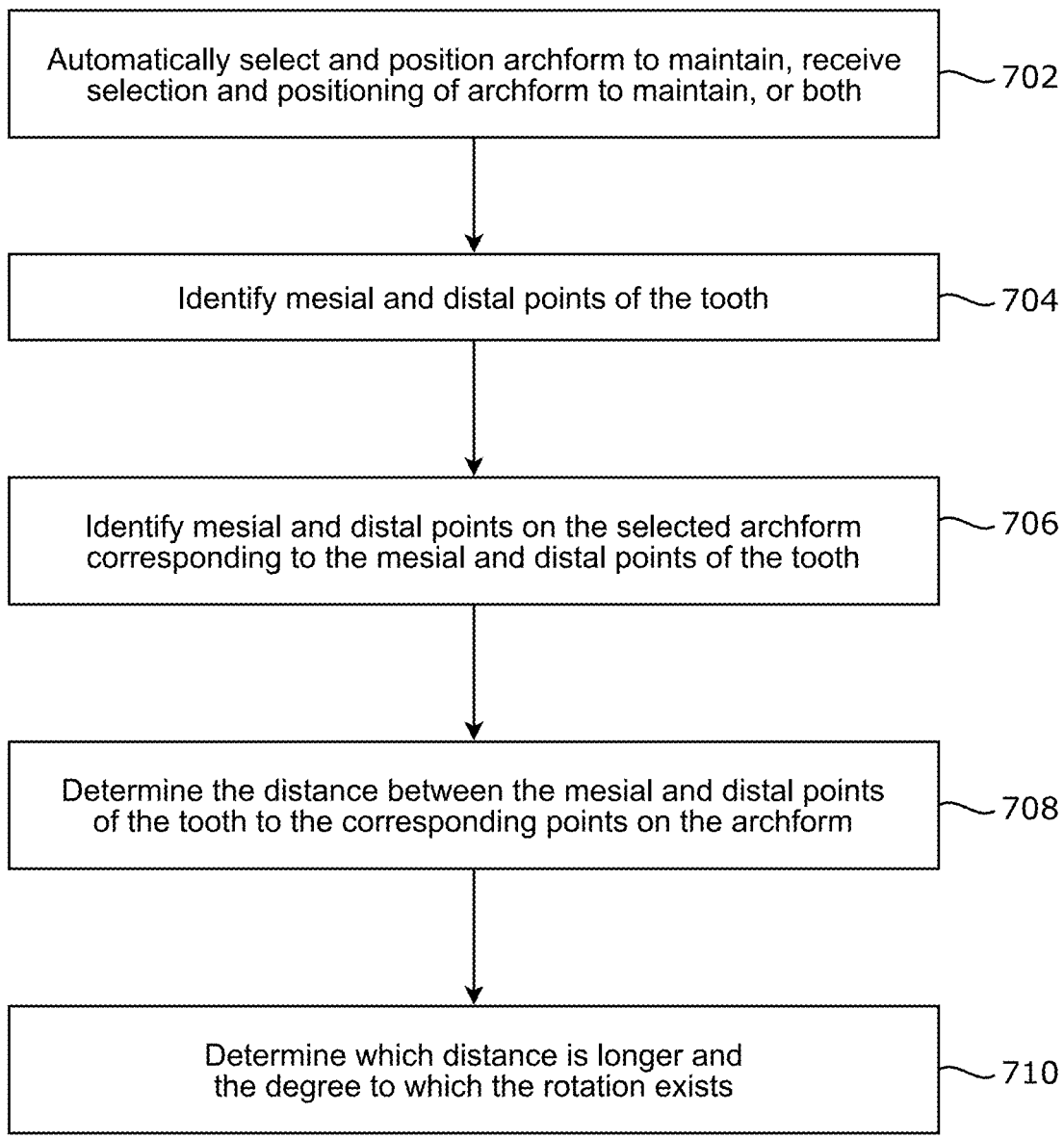
FIG. 7 is a flowchart of the logic determining tooth rotation.

A method (700) representing logic for determining tooth rotation is shown in FIG. 7. Since rotation is measured with respect to the archform, the logic utilizes the automatically selected/positioned archform or the archform positioned and/or selected per the practitioner's input (702). Referring to FIG. 4E the reference archform is shown as the solid line positioned on the labial side of the incisors (424). Logic may also automatically identify mesial ([430] from FIG. 4E) and distal ([428] from FIG. 4E) points of the subject tooth (704). Examples of mesial ([430] from FIG. 4E) and distal points ([428] from FIG. 4E) are shown in FIG. 4E by the dots. One way to determine the direction/degree of tooth rotation of a tooth is to identify corresponding mesial and distal points on the reference archform (706). Mesial (430) and distal (428) points on the reference archform (424) should be a straight line (436) from the respective point (438 and 440) on the tooth to the archform as if creating a 90° angle. Logic can determine the direction of rotation by determining if the distance between from one of points on the tooth to the corresponding point on the archform is greater (708). Whichever distance is greater is usually the direction of rotation (710). For example, in FIG. 4E, the distance from the mesial side of the tooth to the archform is longer; hence, rotation is mesial. Still referring to FIG. 4E, the degree to which rotation is mesial may be calculated by measuring the angle (444) created by where a line through the points on the archform and a line through the points on the tooth meet at "A" (442) (710). In the figure, the angle is five degrees. Note that in this case the top line goes through the mesial and distal points of the reference archform, and the bottom line goes through the mesial and distal points on the image of the tooth. Thus, the simulation defines the variance from the archform as part of an initial calculation and defines the amount of rotation necessary to meet the archform to maintain for each tooth. In some cases, a tooth may already be in alignment, but is necessarily moved to create space for other tooth movements, and the tooth can thus be moved and returned to a final position as necessary for enacting the orthodontic simulation.

To identify various features of tooth anatomy calculate distances, degrees and other calculations, the software logic uses a three-dimensional matrix/grid model of scanned images to plot various points on the x-, y-, and/or z-axis and perform calculations, measurements, etc. based on the plotted points and their relation to each other. For instance, the software logic can identify various features of tooth anatomy based on shadows, curves, flat surfaces, contact points, etc. and plot those features on the three-dimensional grid. As one example, mesial and distal points of an incisor may be identified by distinctive gradient of shadows, transition curves, or both. Distinctive shadowing includes those proximate the tooth's incisal edge and lingual/palatal shadowing the transition from the gumline to mesial and distal sides of the incisal edge. Other features the software logic may use to create a three-dimensional map/grid include the relatively flat labial surface of incisors, the curvature of the incisal edge, curvature at contact points, and typical areas of wear and tear on the tooth. For each type of tooth there are landmarks or features that the software logic can use to create a three-dimensional graph/grid-based map used for calculations, measurements, and the like, where the features including shadowing and/or the degree of shadowing identifiable by tooth type, identifiable curvatures, cusps, grooves, ridges, etc. on the type of tooth. In this way, the software logic can use grid/map data and occlusal table/reference archform data to calculate the starting angles corresponding to each tooth's inclination, angulation, and rotation. Such information provides a unique known starting point for each tooth and allows for improved mechanics toward an end goal tooth position for each of the teeth.

Another measurement obtained via a scan of the oral cavity (and three-dimensional mapping thereof) is the molar bite classification on each side (right/left) of the jaw. Molar bite classification is measured in millimeters (mm) and is generally the distance between the mesial buccal cusp of the upper first molar and the central groove of the lower first molar. Before this disclosure, standard practice for measuring distances for molar bite class was in two dimensions on as single. Now molar bite class measurements can be determined using a three-dimensional virtual model, selected archforms, and the occlusal table. Measurements made in three-dimensions are more accurate than those taken in two dimensions. Since the simulation selection logic disclosed herein utilizes the scope of molar bite to determine which simulations are relevant to a particular patient, the greater the accuracy of the determination, the better the molar bite classification (MBC), the better the results. An embodiment of a method (800) representing logic for measuring molar distances according to this disclosure is detailed in FIG. 8. In an embodiment, MBC may be auto determined based on measurements taken on the grid/map corresponding to the mesial buccal cusp of the upper first molars and the buccal groove of the lower first molars. The practitioner, however, may either move lines superimposed on the scan to indicate the buccal cusp and buccal groove by dragging and dropping lines created as a result of auto identification, or the practitioner may place virtual lines indicative of the cusp and groove over the image. Either way, both the mesial buccal cusp of the upper first molar and the buccal groove of the lower first molar are identified by the logic. When positioning the line (auto, virtual, or practitioner) on the buccal groove of the lower first molar, is should be perpendicular to the occlusal table. From there, a perpendicular line (not seen) from the occlusal table to the archform identifies a first point on the archform for measuring bite class (802). When positioning the line on the mesial buccal cusp of the upper first molar, it should be perpendicular to the occlusal table. From there a perpendicular line (not seen) from the occlusal table to the archform identifies a second point for measuring bite class (804). The distance between the two reference points on the upper and lower archforms is measured (806). The process is repeated for the other side of the jaw (808). If the distance between the two reference points is between 0 mm and 1 mm regardless of the direction (mesial or distal), the molar bite is identified by the logic as being MBC I. If the distance between the two reference points is greater than 1 mm and the lower reference point is distal to the upper reference point, the logic identifies it as MBC II. And if the distance between the two reference points is greater than 1 mm and the lower reference point is mesial to the upper reference point the logic identifies it as MBC III.

Applicant is using rules, rather than hand staging to set an end goal tooth position based on the starting position and the archform to maintain, the molar bite class and the occlusal table. The rules then define a movement through a series of incremental stages that can be enacted in the patient by an apparatus used by the patient. The use of a starting position, a goal end tooth position, the molar bite class, the archform, and the occlusal table and defined rules yield an improved clinical outcome. Indeed, patient molar bite classification is used to determine which simulations are available to the patient. Three molar bite classes (MBC) are used for simulation selection; MBC I, MBC II, and MBC III. If the distance calculated by a method the same as or similar to method 800 is between about −0.99 and +0.99, including the endpoints, the software logic designates the MBC as MBC I. If the calculated distance is greater than or equal to +1.00, the software logic designates the MBC as MBC II, and if the calculated distance is less than or equal to −1.00 then the software logic designates the MBC as MBC III.

Figure 9:
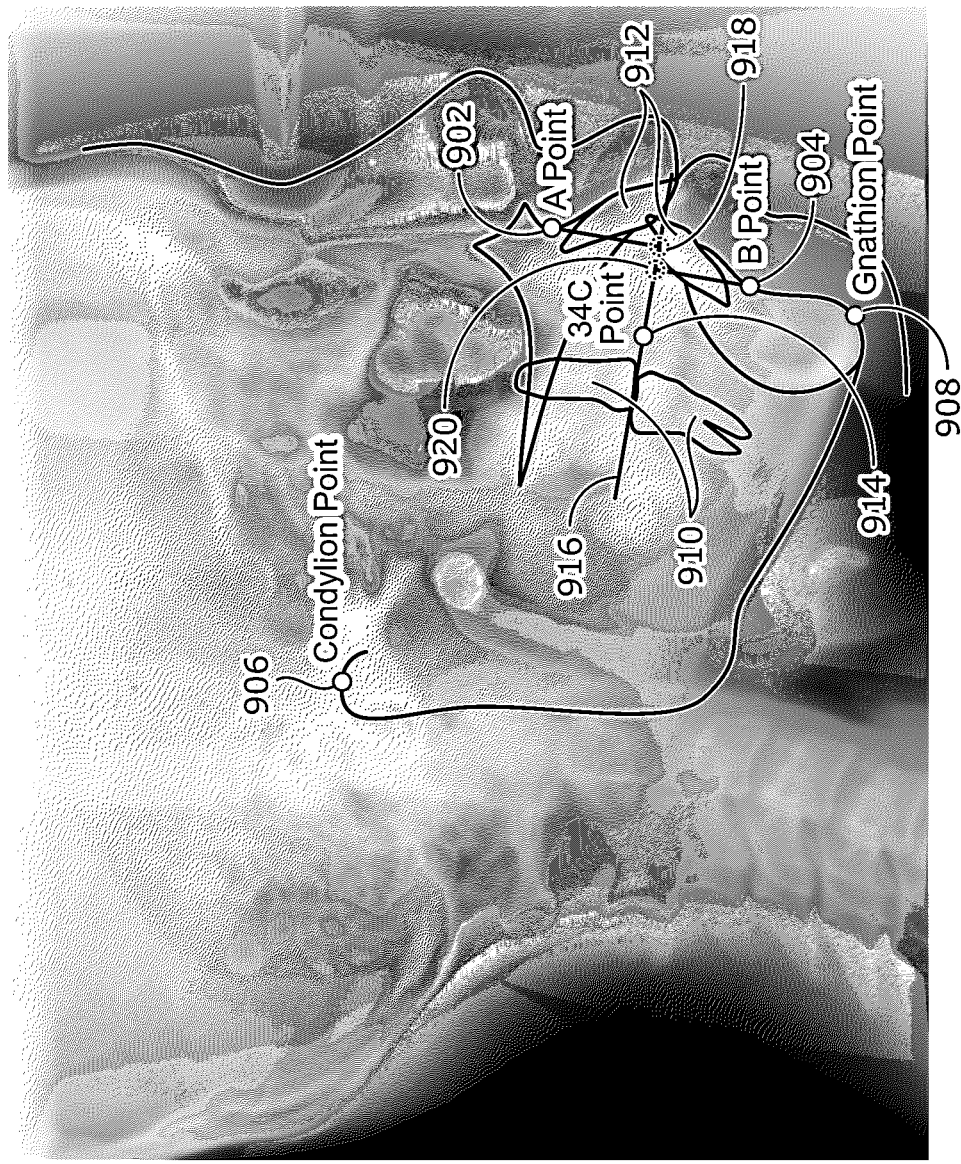
FIG. 9 defines features within a cephalogram suitable for determining a WITS value.
Figure 10:
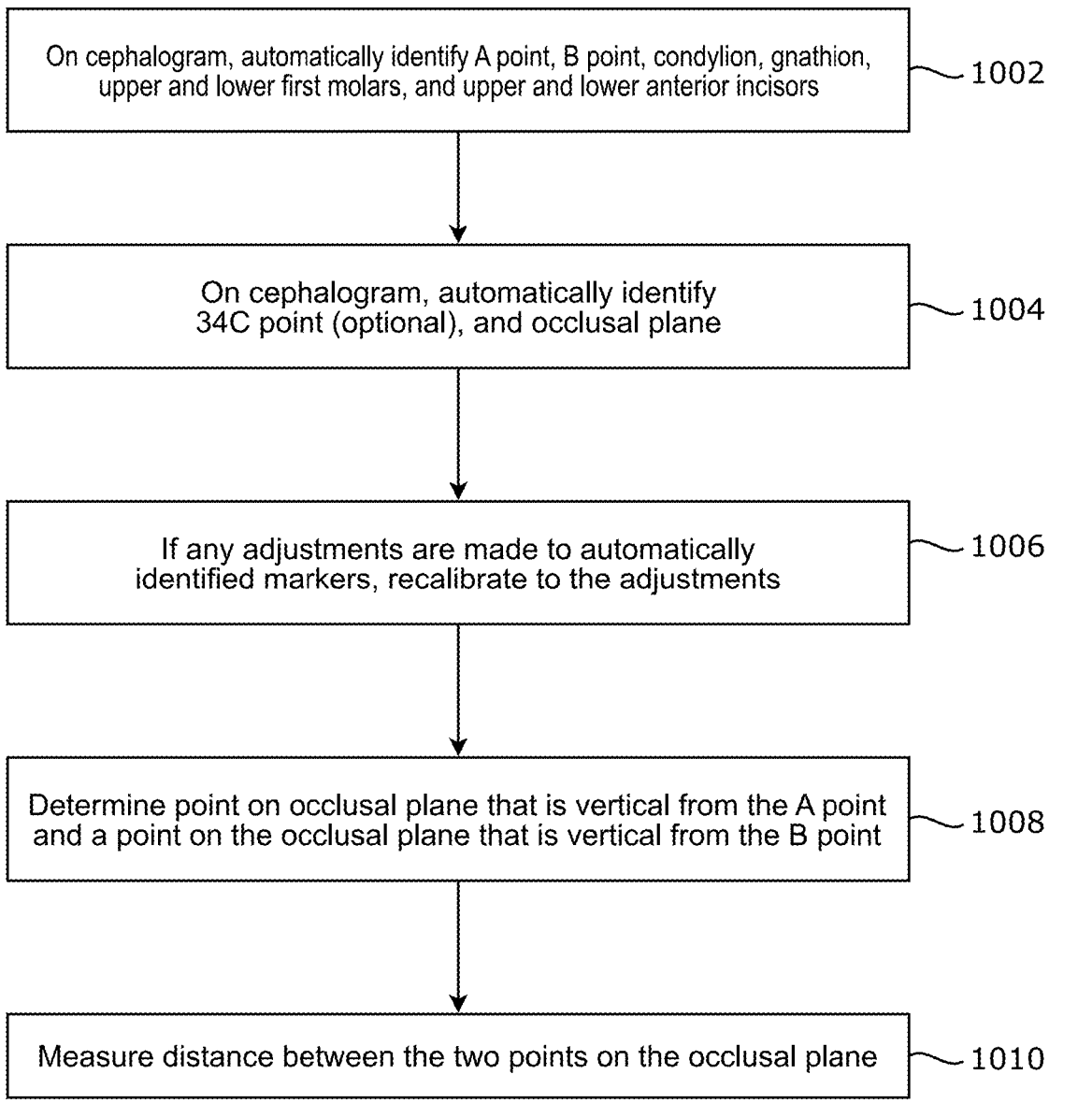
FIG. 10 is a flowchart for calculating a WITS value.

Patient starting data may also include data based on the patient's skeletal structure. In particular, the WITS value for a particular patient helps the software logic decide which simulations are desired for that patient. To calculate a WITS value, the software logic auto identifies various points and structures on an imported cephalogram (FIG. 9). A method (1000) of determining a WITS value using data obtained from the cephalogram (FIG. 9) is described with respect to both FIG. 9 and FIG. 10. Generally, the software logic auto identifies the following points and structures on the lateral cephalogram of the patient: the A Point (902), the B Point (904), condylion (906), gnathion (908), upper and lower first molars (910), and the upper and lower incisors (912) that are the most anterior and visible on the X-ray (1002). The software logic may also identify a 34C point (914), which is the cusp tip on the first premolar and it may set the occlusal plane (1004). The practitioner is able to adjust auto identified points and structures, including the occlusal plane, should the auto identify indicator need to be altered (1006). For example, points may be auto identified on the cephalogram by a dot or dot-like marker and structures may be traced (FIG. 9). Both dots and traces are adjustable by the practitioner. To calculate the WITS value, two points on the occlusal plane are identified and the distance between the two points is measured and expressed in millimeters (mm) in an embodiment (1008, 1010). The occlusal plan in two-dimensions is the occlusal table in three-dimensions. One point on the occlusal plane (916) corresponds to a vertical line being drawn from the A point (902) on the cephalogram to the occlusal table (916) on the cephalogram so that the line would form a 90° angle (918) with the line depicting the occlusal table ([916] from FIG. 9). The other point (920) is the same except for being drawn from the B point ([1008] in FIG. 10, [904] from FIG. 9). The determined distance between these two points made on the occlusal plane is the WITS value (1010). If the point on the occlusal from the A point (902) is in front of that from the B Point (904), the WITS value is positive, but if the point on the occlusal table extending from the B Point (904) is in front of that from the A Point (902) then the WITS value is negative. The WITS value is used in simulation selection as an indicator of skeletal class. Skeletal class I is indicated by a WITS value of negative 3 (−3) to positive 3 (+3), skeletal class II is indicated by a WITS value of greater than 3 (>+3), and skeletal class III is indicated by a WITS value of less than negative 3 (<−3). In other words, simulation selection and/or endpoint determinations are based on the WITS value among other factors. In particular, for a given simulation, logic references an endpoint table defining endpoint positions for each tooth (i.e., angulations, inclination, and rotation), where the indicated endpoints are based on the skeletal differences determined by the WITS value. Thus, certain WITS values will implicate the movement available to a given patient, where some patients may have more or less available skeletal movement as compared to another patient. Therefore, use of WITS value can eliminate some mechanics options from a given patient due to structural limitations.

Figure 11:
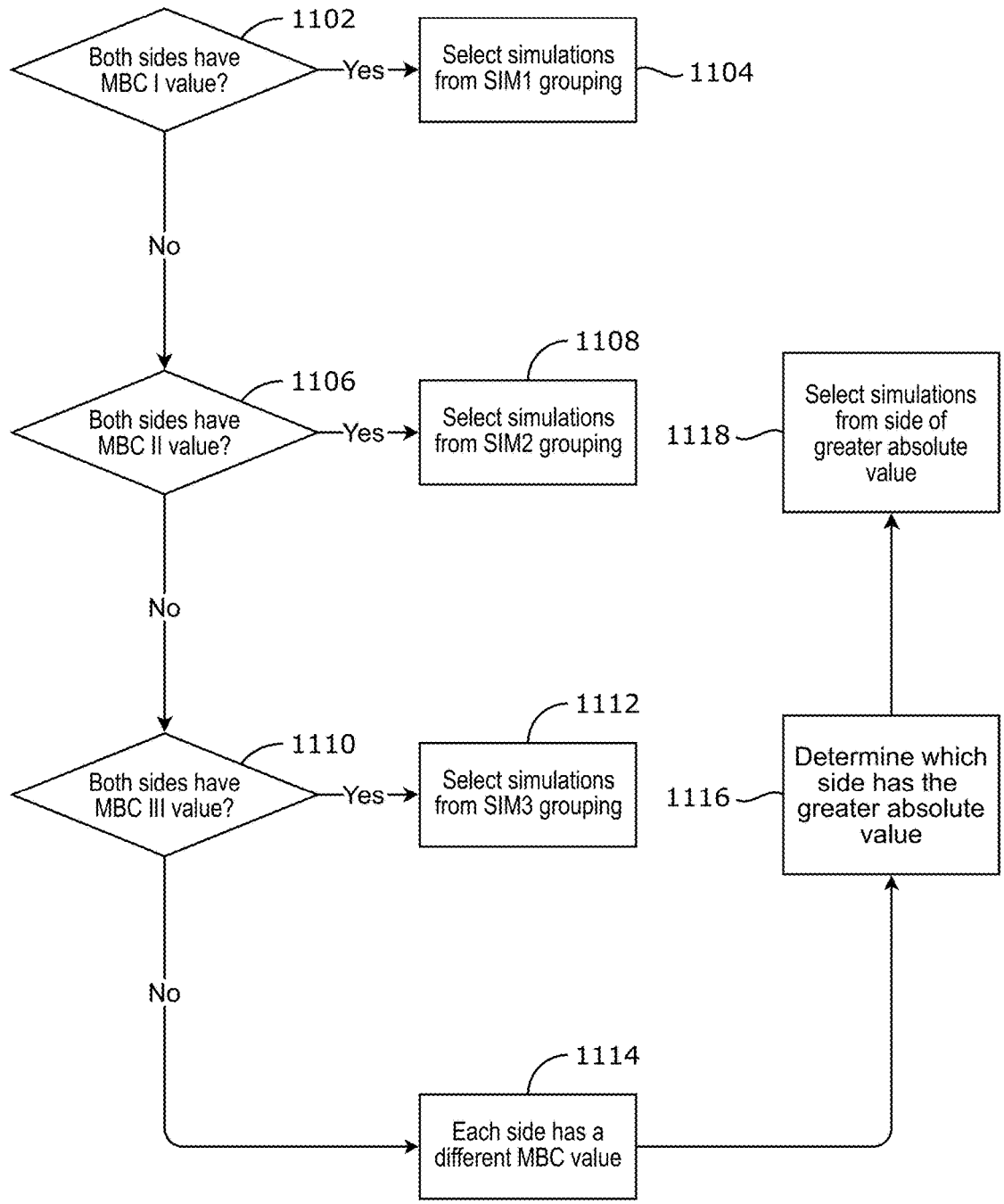
FIG. 11 is a flowchart for the logic for determining SIM group (SIM1, SIM2, SIM3) selection and related rules.

The software logic uses patient start point data described above in FIGS. 8, 9 and 10 to determine which one or more simulations are appropriate for the patient. Turning to the logic (1100) described in FIG. 11, first, using the determined MBC, the software logic identifies a simulation group ("SIM group") that is available to the patient. SIM groups correspond to MBC. If both sides of the patient's jaw have an MBC I value (1102), the software logic selects simulations in the SIM1 group (1104). If both sides of the patient's jaw have an MBC of II (1106), the software logic selects simulation in the SIM2 group. If both sides of the patient's jaw have an MBC of III (1110), the software logic selects simulations in the SIM3 group (1112). This is easy enough if the patient has the same MBC determination on both sides of the jaw. If, however, the MBC determination on one side if the jaw is greater than the other side (1114) then the software logic determines which side of the jaw has the greater absolute value (1116) and uses the larger valued classification for selecting one or more simulations that are available to the patient (1118).

Regardless of the actual simulation/s that are available to a patient, the software logic determines how to virtually move each tooth from the start (utilizing start data) to align with the archform to maintain using tooth position endpoints corresponding to a particular endpoint table. Rules may be "universal" or specific to a particular simulation. One universal rule applicable to all simulations is that the logic may never move lower molars to the back in a posterior direction. Further, upper molars can only be moved in a posterior direction under limited circumstances, which are simulation specific. Both upper and lower molars may be moved forward, or in an anterior direction. Anterior molar movement, however, is simulation specific. Also, with respect to molar movement, the simulation logic will attempt to make both the right side and the left side of dental arches symmetrical, thus, molar movement on each side does not necessarily have to be the same distance or degree, but it still has to abide by the limits of a particular simulation. Additional rules that the software logic has to follow are directed to anterior teeth such as canines and incisors. For example, anterior teeth may be moved in an anterior direction to create space needed for tooth realignment. However, they can only be moved forward to the point where they "hit" or collide with the archform. Thereafter, if the anterior teeth need to be moved to provide additional space, the archform itself must move forward before allowing any additional anterior movement of the anterior teeth. Anterior movement of front teeth may enable teeth posterior thereto the room needed to realign to/toward the reference archform at the prescribed endpoint positions. Further limitations on tooth movement include being able to detect if teeth will collide with one another during repositioning and accommodating tooth collisions and ensuring that at the end of a simulation spaces are closed. Thus, while calculating the differences between start and endpoint inclination, angulation, and rotation of teeth, and other movements, the software logic may be limited in what it can generate at the end of the simulation due to the above constraints and more. In other words, the simulation is not going to show a set of perfectly aligned teeth if the simulation mechanics, rules, and endpoint positions prevent that from being achieved for the patient. Further, the software logic orchestrates changes about an axis in one-degree increments. That is, for degree-based changes such as with inclination, angulation, and rotation, the software logic will allow the tooth to change its position one degree at a time (e.g., per stage) from the start measurement to the endpoint prescribed in the appropriate endpoint table and aligned to the archform. Likewise, for distance-based changes such as intrusion, extrusion, expansion, constriction, and the like the software logic will calculate changes in increments of about 0.1-0.2 mm per stage. Thus, per each stage of tooth movement, each angle (e.g., inclination, angulation, rotation) of each tooth may change up to one degree until the desired endpoint is reached and may be moved up to about 0.1 to 0.2 mm per stage. How many stages and the length of time a patient stays in a particular stage depends upon each unique patient start point, archform to maintain, prescribed tooth position endpoints, and obstacles (e.g., collision, growth, posterior crossbite, etc.) that may need to be overcome. With aligners, a new aligner may be printed per stage (an intermediate position of the teeth), from the first stage to the Nth stage, until the last endpoint for each tooth has been obtained, or as close thereto as possible.

In an embodiment, a patient may be allowed to accelerate treatment by having the aligner for every other stage printed, hence skipping every other stage. This would force the patient to move at more than the about 0.1 to 0.2 mm, including up to about 0.4 or even 0.5 mm over the course of the now, two, stages, as the patient would virtually pass through the skipped stage. This increases the velocity of the treatment, forcing a faster rate of movement using aligners as the orthodontic apparatus. Thus, where large movements are desired or required, it is not that the stage does not exist, it may simply be passed over to effectuate some larger movements needed for the orthodontic simulation to proceed.

Although all teeth in the upper and lower arches may simultaneously be repositioned (both distance and degrees) at each stage, software logic has several overall goals with regard to tooth movement, which may or may not be phased. These goals include leveling the teeth in relation to the occlusal table, moving the teeth to align with the archform, changing three measured positions for each tooth so that when the simulation is finished each tooth is at or as close to the prescribed angle as possible, and all the while avoiding tooth collision. Since patient problems vary and their measured start points vary greatly the path that the simulation logic "chooses" for each patient from start to finish will also vary. This is especially true given that archforms, while predefined, will also vary from patient to patient as will their molar class and skeletal structure. Thus, although the various goals are described linearly, the software logic will choose what to do next with regard to a particular tooth based on several factors including where it needs to go to accomplish the goals and how each tooth will relate to the other once moved. If the proposed movement causes a collision, another problem presents, is not allowed by the simulation mechanics and/or rules, the logic "tries again" until an acceptable next stage is reached. Thus, for each simulation scenario (and each patient for which the simulation is run) the logic's determined path to the end of the simulation may differ. As such, the following description regarding tooth movement is centered on the goals trying to be achieved and not necessarily the actual order of movement.

Since inclination and angulation measurements are relative to the occlusal table, one of the logic goals is to "level" teeth thereto. Leveling does not mean that all teeth are at the same height, rather, there are specified relational distances with respect to teeth height. At the same time, the logic is moving teeth to align with the archform to maintain. Thus, although movement of teeth may be described as being phased generally first to the occlusal table (e.g., inclination and angulation) then to the archform to maintain (e.g., rotation), in reality, movement distances, directions, changes along the central or other axis, etc., may occur simultaneously, sequentially, sequentially with overlapping timelines, and other variations as repositioning teeth to a particular endpoint result depends upon taking many factors into consideration to obtain the desired result.

Figure 12:
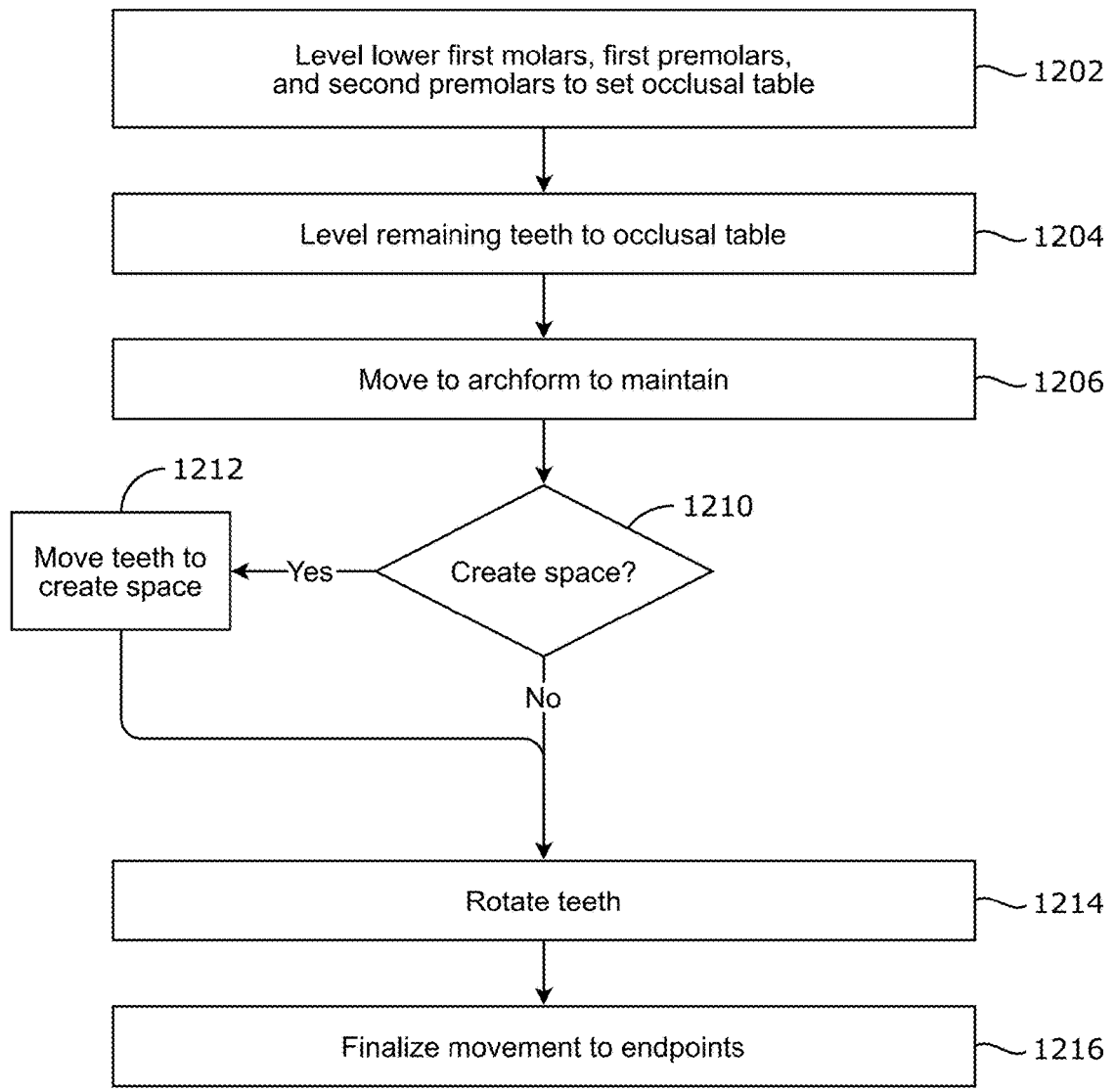
FIG. 12 is a flowchart regarding movement logic.

Regarding repositioning with respect to the occlusal table, the software logic looks to the occlusal table reference teeth to determine what changes are needed to "level" these teeth to the occlusal table. Generalized logic for an "ideal" leveling is represented by the method shown in FIG. 12 (1200). For example, in an embodiment, the tips of the distal buccal cusps of the first molars and the tips of the buccal cusps of the first premolars are the reference points to establish the occlusal table. That does not mean that the entire tooth is leveled with respect to the occlusal table. These teeth (lower 4s and 6s) may still be angled and/or inclined, and as such the software logic will address these changes to reposition the reference teeth. For example, although the cusp tips may be on the occlusal table, other parts of the tooth may be either above or below the occlusal table. If above the occlusal table then the tooth may be intruded to move it toward the bone or if below the occlusal table then the tooth may be extruded to move it away from the bone. Since intrusion and extrusion are measured in millimeters (mm) the software logic will determine how many 0.1 mm increments are needed to level the lower first molars, first premolars, and second premolars to the occlusal table (1202). Intrusion and extrusion can also alter the angulation of the teeth being moved and set to the goals as defined, for example in the endpoint table defined herein. As such, angulation (and inclination) changes may also take place at the same time as extrusion/intrusion with the logic noting the appropriate rates of change (e.g., degrees, millimeters, both). Second premolars are also leveled with respect to the occlusal table with a desired endpoint angulation being about 90°. Ideally leveled lowered first molars will be at occlusal table with the mesial buccal cusp tips slightly above the occlusal table at angles prescribed in the relevant EPT, the first buccal cup tips of the first premolars are leveled to the occlusal table with an inclination and angulation prescribed in the relevant endpoint table, and the second premolars will be leveled so the buccal cusp tip is on the occlusal table and marginal ridges are parallel thereto, at a preferred angulation of about 90°.

The lower second and third molars (7s and 8s) may be leveled (intruded/extruded) to the occlusal table to be at about the same height as the first premolars. Even so, endpoint inclination and angulation indicated for second and third lower molars may or may not be the same as those indicated for first premolars. Lower canines and lower incisors may also be virtually extruded/intruded to be at the corrected height with respect to the occlusal table (1204). For example, in an embodiment, lower canines are intruded/extruded to both be about 0.5 mm above the occlusal table. At the same time, the angulation of the lower canines may be moved toward their prescribed endpoint positions. Lower incisors should ideally be repositioned (e.g., intruded/extruded) to be level with the height of the occlusal table, but as with most leveling, being leveled can be secondary to endpoint inclination and angulation specifications. Leveling and angulation are separate where leveling refers to a height of the tooth with respect to the occlusal table (e.g., above, below, at, in millimeters) while angulation refers to whether a tooth is tipped in one direction or the other with respect to the occlusal table (degrees). A tooth can be at the height of the table yet tipped so that a portion is slightly above or below the occlusal table.

Teeth in the upper dental arch can also be leveled to a height with respect to the occlusal table (1204). Since the upper teeth overlap portions of the lower teeth, the occlusal table may be envisioned as being horizontal plane at the level of central groove of the upper first molar (6s) and the mesial line angle (labial/buccal) of the upper first premolar (4s). Thus, the buccal cusp tips of premolars and molars are typically below the occlusal table when leveled thereto. As such, when in a closed bite position, the inclined planes of the upper and lower occlusal surfaces will fit together, like puzzle pieces. Proper inclinations of teeth help establish proper fit of upper and lower teeth at the level/height of the occlusal table. For at least this reason, concern addressed by software logic is calculating the position differences between start and endpoint measurements to incrementally change the positions (e.g., inclination, angulation, rotation height) of those teeth with reference to occlusal table while determining if a particular change will result in a collision with another tooth. Like the bottom teeth, the upper canines and incisors are also leveled with respect to the occlusal table. In this case, however, the central incisors and the canines are expected to sit below the occlusal table by about 1.5 mm. Since the lower incisors are generally level/at the height of the occlusal table, there will be an overbite of the upper incisors of about 1.5 mm. An overbite of this size allows the inclined planes of the posterior teeth to fit together for proper occlusion. It also prevents the lower incisors from impacting the lingual surfaces of the central incisors. Lastly, per leveling relative to the occlusal table, the upper lateral incisors will ideally about 0.5 mm above/superior to the occlusal table. Thus, like lower teeth, upper teeth may be virtually inclined, angled, intruded, extruded, relative to the occlusal table, or as much as is possible to be in accordance with predetermined endpoint positions per a simulation specific EPT.

Teeth are also being moved from their start positions to the archform to maintain so that the teeth are aligned per the archform and rotated with respect thereto (1206). Ideally, the reference archform should be virtually identified/fixed in space by the software logic as being on the labial/buccal side of the first molars and first premolars/canines about halfway between cusp tips and the gingival crest, and parallel to the occlusal table. In this way, the software logic can identify tooth position relative to the archform/s as well as to the occlusal table, each representing fixed points in space that the software logic references to determine the incremental movements needed to be at the desired inclinations and angulations relative to the occlusal table while at the same time in a desired endpoint alignment and rotation with respect to the archform to maintain. Again, incremental movements for changes in rotation, inclination, and angulation (about an axis) are one degree at a time, whereas any distance that a tooth has to travel is in about 0.1-0.2 mm increments. Embodiments, however, may utilize a different movement rate compatible with reaching end goals of simulation, treatment, or both. As such, using the archform to maintain as a reference, the software logic will determine if a tooth has to move toward the archform, away from the archform and by how much, as well as the desired rotational endpoint.

To move teeth toward the archform, teeth appear to shift crown first with the incisal edges, cusp tips leading the way with root movement coordinated therewith (1206). To the extent possible, rotation, angulation, and inclination of lower (and upper) molars is determined first with movement toward endpoint parameters and with reference to the occlusal table and archform to maintain. Thereafter, other tooth movement may be determined. Rotation is relative to the archform to maintain, e.g., the archform from FIG. 6 selected for start position calculations. In an embodiment, the selected archform to maintain remains the rotational reference even if a particular simulation/set of rules calls for the archform to be changed during the actual simulation such as for expansion. Since logic attempts to move a molar first and then other teeth in relation thereto, molar rotation or other movement may be prevented if other teeth are crowded and block the path of intended molar movement. As such, logic may need to move anterior teeth (1212) before virtually repositioning a molar to create space (1210) for the molars to move into. If space is not an issue, the logic can move the desired tooth, i.e., its rotation (1214) and finalize movement to the goal endpoints (1216). It should be noted that in some cases, when the archform to maintain is an expansion, such expansion may be temporary to create space, even as little as 0.1 mm, to allow for freedom of movement, and wherein the nonexpansion archform is still desired as the goal endpoint.

Figure 13:
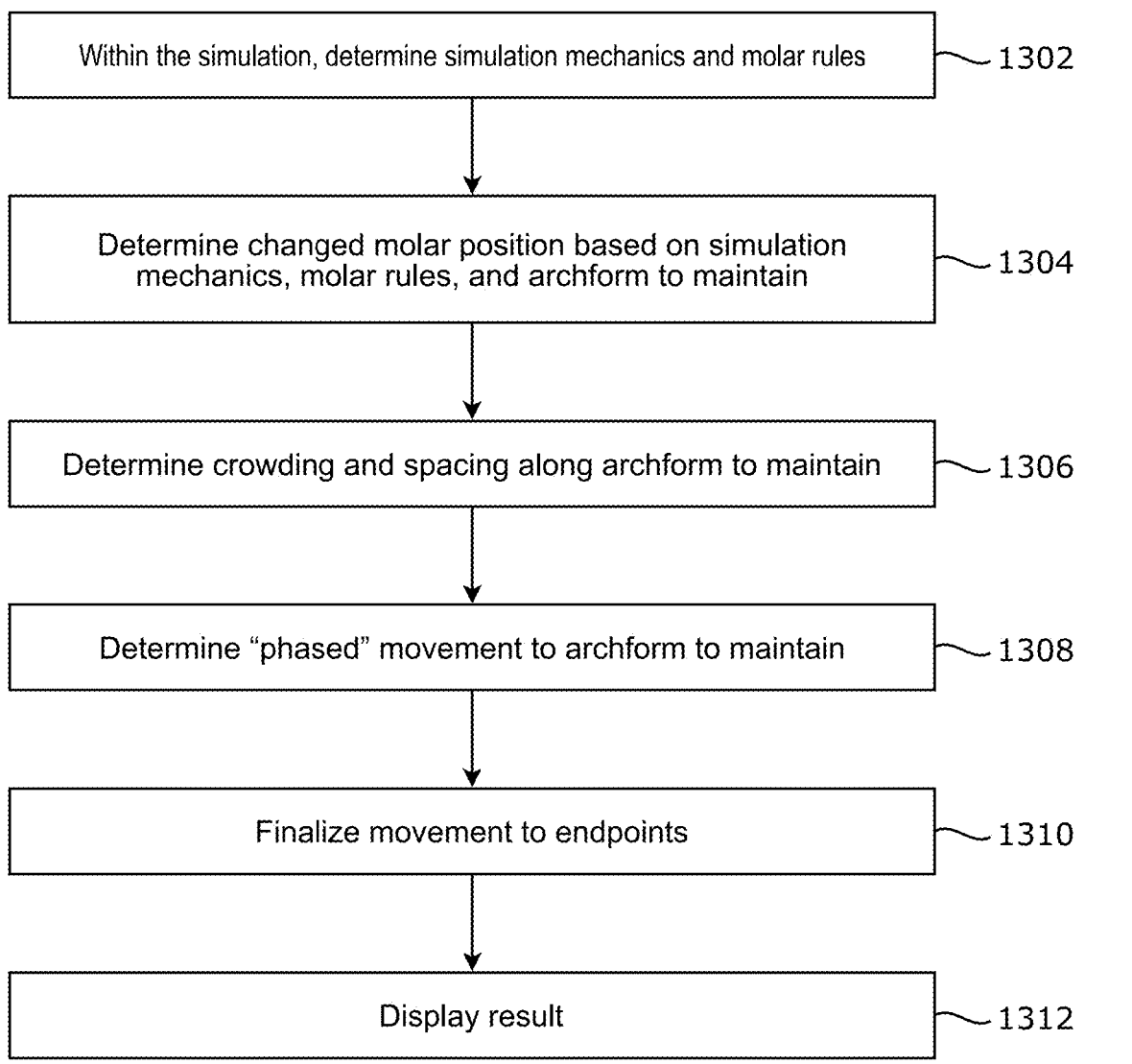
FIG. 13 is a flowchart for determining simulation mechanics.

Thus, as is shown in FIG. 13 logic calculates incremental movements for teeth from their start positions to their end positions using the particular simulation parameters such as defined mechanics and rules (1302). Logic may try to determine a virtual path forward by analyzing molar positioning (e.g., in increments, where molars need to be at the end of the simulation, or both) and if allowed, virtually repositioning nonmolars (1304). In an ideal situation the incremental movements are unhindered and can be repositioned by logic without complication. Nonetheless, logic also determines crowding before and/or after tooth movement especially with respect to the archform to maintained as it is desirous for final alignment to emulate the shape of the archform to maintain (1306). To the extent possible, the logic may implement "phased movement" (1308), with teeth being leveled, angled, and inclined relative to the occlusal table while progressing toward predetermined endpoint values. In the next "phase" teeth may be moved toward the archform to maintain (if not already at or heading in that direction). If either of these phases are not possible and a particular path is blocked (e.g., another tooth is in the way), an alternative movement path to desired tooth positioning can be determined. This can include, but is not limited to simply choosing a different movement mechanism, or modifying a linear movement, of each tooth, and instead moving one tooth instead of another, to create the space to prevent the collision of the two teeth. Notably, although the lower molars cannot be moved in the posterior direction while potential repositioning is being determined, they are allowed to move "sideways" toward the archform while being leveled to the occlusal table (e.g., by extrusion/intrusion) and rotated. In the final stages of simulated realignment, teeth are being put as close to their final endpoint positions as possible in the shape of the archform to maintain and spaces are closed up (1310). Final results of a particular simulation may be displayed (1312) for patient viewing.

Ideal scenarios are most likely the exception to a nonideal rule. That is, people generally seek to straighten their teeth where there are issues such as overcrowding of teeth. There is not enough space in the dental arch/es to allow the teeth to be in proper or acceptable positions. Further, crowded teeth can be prevented from moving because they are touching in a way that prevents corrective movement or they will be touching in such a way once an incremental movement takes place. Thus, as the software logic determines the changes the teeth need to make to be repositioned per a given endpoint table, it also determines which teeth will collide in a way to block progression toward endpoints. Since collisions are more significant when trying to reposition teeth with aligners than with brackets, the software logic determines how to strategically straighten teeth (e.g., with aligners) while avoiding collisions or using collisions advantageously. Generally, space can be made to accommodate teeth by moving anterior teeth forward (advancement) and/or to the side, expanding (widening) the archform, or both. Under certain circumstances molars too may be moved forward to create space for repositioning. Thus, while determining changes from start point positions to endpoint positions, the software logic will also identify when one or more teeth cannot move due to a collision, can move even though there is a collision since the other tooth is also moving in a way that does not prevent movement, or are free to move in the desired direction since no collisions are detectable. Accordingly, one of the technical advantages of the present embodiments is that because of the precision of the measurements, the modeling of each movement within the system, and the movement rules, collisions can be mitigated and prevented better by use of the methods and systems described herein, than as compared to the prior art. Indeed, because of the precision, modeling of fine tolerances, such as even 0.1 mm, can be utilized to prevent collisions when use of molds and other prior art systems the error rate and variance of such systems would not allow for such narrow tolerances without undue risk of collisions within their simulation and treatment plan. Generally, the software logic can identify a collision when two adjacent teeth are calculated to be at least partially (e.g., mesial-distal contact of adjacent teeth) in the same space at the same time. In other words, two objects cannot occupy the same space at the same time; thus, if two teeth are projected to be in the same space at the same time due to a particular attempted virtual movement, a collision is detected and has to be delt with by logic. If an adverse collision (e.g., movement is blocked) between two teeth is identified by the software logic, the situation may be addressed early on by coordinating movements to separate the contacts as they expand or constrict crowns toward the archform. Further, incisors can be advanced to create space to allow for subsequent movement, and do so within the narrow tolerances as afforded due to the precision of the methods and systems detailed herein. This allows for a more narrow movement plan than can be provided in previous systems where the tolerances and error ranges would not allow for such fine distinctions as provided by the rules within the methods and systems of this disclosure.

A different sort of collision takes place when a tooth reaches the archform, which is the limit of expansion. This is especially relevant for posterior tooth movement toward inclination endpoints as crowns move laterally for inclination adjustment. Similarly, collision with the anterior/forward portion of the archform also limits the extent to which room can be made for crowded teeth anterior thereto. The anterior teeth cannot be moved laterally due to collision with the archform in that direction. As such, the software logic can move the archform forward to create more space for teeth. In this case, if space is available, the archform can move back toward stationary molars to close any gaps such as during the last phase of treatment.

Another potential collision is when upper and lower incisors inappropriately collide. For example, incisors are not allowed to be imbedded in each other such as when lower incisal edges collide with upper cingulum, which is palatal ridge near gum line. How software logic accommodates for this, and other types of collisions, depends on specific simulation instructions/rules, but general strategies include: (i) after incisor leveling intrude upper and/or lower incisors, (ii) change the inclination/torque of the upper and/or lower incisors, (iii) advance the upper incisors, and/or (iv) change the position of the lower incisors using IPR. If the inclination/torque of incisors is an available option to overcome upper/lower incisal collision, with respect to the upper incisors, the crown may be inclined labially without moving the root, or the upper root may be inclined lingually. In contrast, the crown of lower incisors may be moved back lingually with the root staying the same. Also, although upper anterior teeth may be moved forward to accommodate crowding, the lower teeth may not be moved forward or not to the extent that it will cause incisal collision. As a result, the software logic will leave lower crowding without advancing the lower incisors. Thus, regardless of which SIM group (1, 2, or 3) the software logic determines is appropriate based on molar bite classification, the simulations generally try to move molars first and remaining teeth moved/reposition after determining molar movement all while avoiding collisions. Each SIM group and subsimulation, however, can have additional limitations, and/or other options available when determining a path forward for optimal realignment.

Simulations can be grouped by MBC or mechanics of the simulation or both. If grouped by MBC, there are at least nine mechanics scenarios in the SIM1 group, nineteen mechanics scenarios are the SIM2 group, and nine mechanics scenarios in the SIM3 group. Although thirty-seven mechanics scenarios are defined at present this number can be more or less based on different mechanics protocols and/or dividing a particular class into subdivisions.

Figure 14:
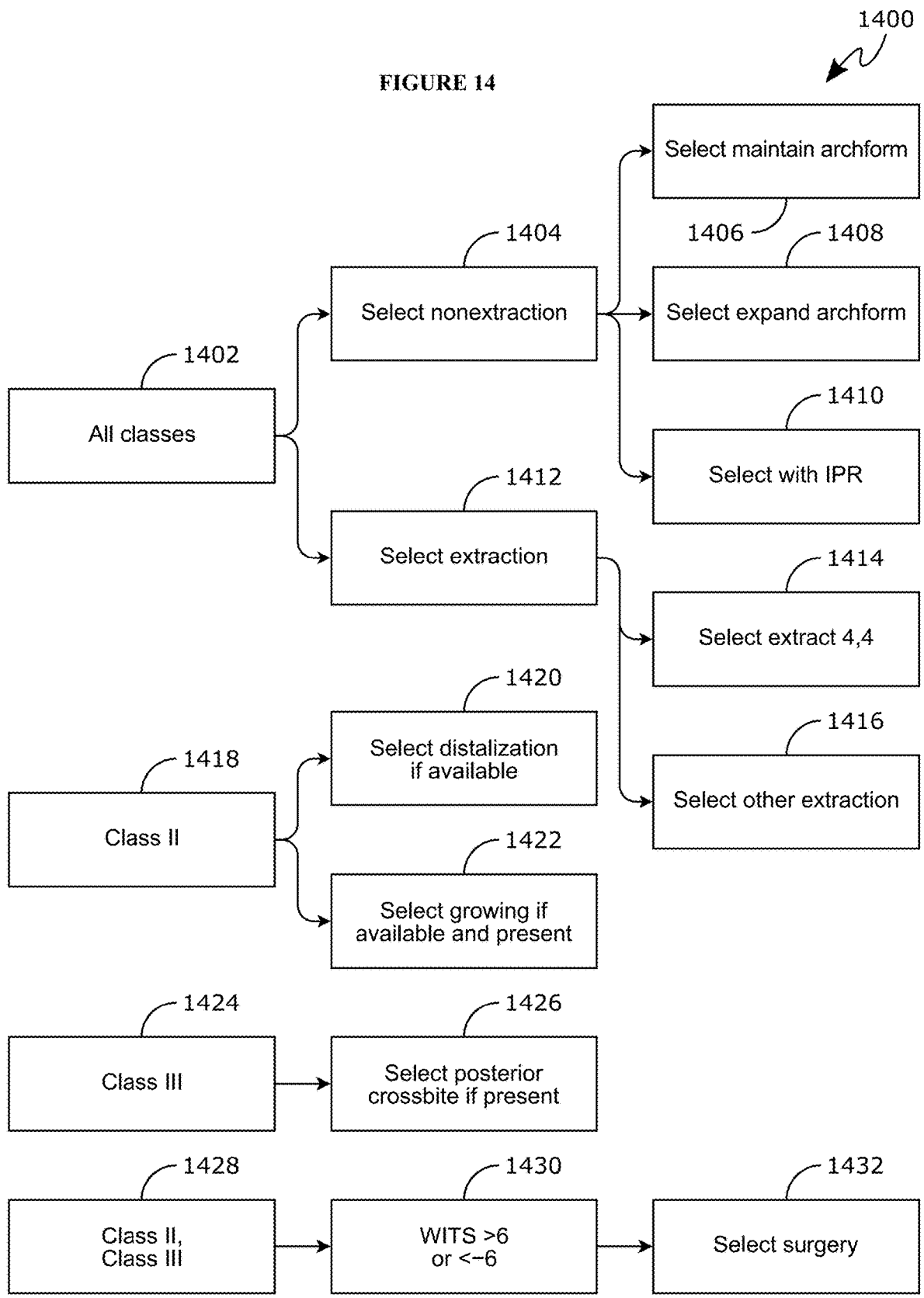
FIG. 14 is a flowchart regarding molar bit class ("MBC") selection and available mechanics.

Different mechanics scenarios can be the same across MBCs. For example, FIG. 14 shows how simulations may be logically selected according to their mechanics (1400). Certain simulation mechanics are available for all MBCs (1402). There are a certain number of nonextraction (1404) and extraction mechanics (1412) simulations defined for each class. Of nonextraction mechanics, at least one option for each MBC will include maintaining the archform that was selected at the beginning of setup (1406) and another will replace the selected archform with an expanded archform (1408). In an embodiment, the archform may be maintained (1406) and paired with IPR (1406, 1410). In an embodiment, the archform may be expanded (1408) and paired with IPR (1410).

Within an MBC the same mechanics scheme can be specialized for different subgroups. For example, MBC II can be divided into subgroups based on the extent of the malocclusion. Thus, the same mechanics scheme (e.g., nonextraction, extractions, etc.) can be further defined to apply to different subgroups within an MBC. Examples of MBC II subgroup divisions include grouping by defined amounts (e.g., +1.00 to +3.00 and from +3.01 to +5.00), or by amounts that are less, greater, or equal to an amount (e.g., 2.00, 3.00, 5.00, etc.). Thus, a general predefined mechanics scheme can be subdivided based on the degree to which the malocclusion occurs in any one or more systems of subdividing. The same is true for simulations that include extractions (1412). There are several simulations/subsimulations that call for extracting upper and lower first premolars (1414), and others that utilize variations on which other teeth are extracted (1416).

Some simulation mechanics are particular to a class/subset of a class. Within class II (1418) there are specialized simulation mechanics using a distalization protocol (1420) and others for growing patients (1422). And within class III (1424) there is a specialized protocol for correcting posterior crossbite (1426). A surgical simulation option even exists for class II and class III (1428) patients that have a WITS value of >6 class II or <–6 class III (1430) where the surgical option is followed by correction (1432). Thus, when determining which simulations are available to a particular patient logic uses the patient's MBC as a first level of screening and a subgroup within the particular MBC as a second level of screening. Third levels of screening can include particulars such as if the patient is growing, has a posterior crossbite, fits within distalization protocol parameters or surgical parameters. The simulations that are available to a particular patient are those that are remaining after screening/filtering per the above scheme. At the very least a nonextraction simulation will exist for most if not all patients. Typically, more than one simulation scenario (e.g., mechanics) will be available to a given patient. It should be noted that many simulations may be adjusted to accommodate patient growth even though they are not specifically designated for growing patients only. Some simulations may be expressly prohibited if a patient is still growing.

Each simulation refers to an endpoint table (EPT) to determine how each tooth should be positioned at the end of the simulation. Ranges of endpoints for most/all simulations are in Table 1, below. In an embodiment, each simulation has a unique EPT for distinct skeletal classes with distinctions made to accommodate the three types of skeletal class determined by the WITS value. Thus, when determining final tooth positioning, the logic can look up the relevant EPT for the subject simulation, by skeletal class I, skeletal class II and skeletal class III. The ranges shown in Table 1 encompass endpoint possibilities for all skeletal classes. Before this disclosure, orthodontic simulations were designed to align all teeth in the same way without consideration of the individual patient much less their skeletal class. In those simulations there is only one end possible and that is the only goal. Per this disclosure actual end results vary from simulation to simulation and patient to patient. End results vary from simulation to simulation due to the different mechanics used to reach the endpoint. Further, each simulation has different predefined endpoint parameters, which will also cause variance in tooth position, hence results. And within a simulation there are at least three distinct EPTs adjusted to provide a result that is achievable under the mechanics of the simulation and the particular patient's skeletal class. No other orthodontic simulation shows the patient clinically significant, achievable results based on specific mechanics employed to get to the result using predefined endpoints for the given mechanics scenario and the patient's skeletal class.

TABLE 1

RANGES FOR ENDPOINT POSITIONING FOR EACH TOOTH

|  | Tooth No | Inclination Degrees | Angulation Degrees | Rotation Degrees |
|---|---|---|---|---|
| Molar | 18, 28 | 87-97 | 88-92 | 1-7 |
| Molar | 17, 27 | 87-97 | 88-92 | 4-10 |
| Molar | 16, 26 | 87-95 | 85-92 | 3-10 |
| Premolar | 15, 25 | 87-93 | 85-90 | 0-5 |
| Premolar | 14, 24 | 87-93 | 90-95 | 0-5 |
| Canine | 13, 23 | 92-93 | 97-99 | 0-5 |

TABLE 1-continued

RANGES FOR ENDPOINT POSITIONING FOR EACH TOOTH

|  | Tooth No | Inclination Degrees | Angulation Degrees | Rotation Degrees |
|---|---|---|---|---|
| Incisor | 12, 22 | 53-72 | 97-99 | 0-5 |
| Incisor | 11, 21 | 46-64 | 91-98 | 0-5 |
| Molar | 38, 48 | 92-98 | 88-92 | 0-5 |
| Molar | 37, 47 | 92-98 | 88-92 | 2-9 |
| Molar | 36, 46 | 92-98 | 85-92 | 5-12 |
| Premolar | 35, 45 | 92-98 | 85-90 | 0-5 |
| Premolar | 34, 44 | 93-95 | 90-95 | 0-5 |
| Canine | 33, 43 | 89-95 | 85-97 | 0-5 |
| Incisor | 32, 42 | 54-80 | 90-95 | 0-5 |
| Incisor | 31, 41 | 54-80 | 87-93 | 0-5 |

Ranges provided in Table 1 were determined by analysis of data gathered over the course of years to determine desired/achievable inclination, angulation, and rotation positions for each tooth. Thus, for each simulation, desirous endpoint values were determined based on what is achievable for each skeletal class (i.e., determined by WITS value) according to the simulation mechanics. Such values, however, can be modified or altered outside of these desired parameters by the attending doctor when setting a final endpoint goal for a particular case. By setting a final endpoint goal, whether within the above defined parameters, or having one or more parameters outside of such range, the system can then perform the calculations and movements as detailed through this disclosure to reach the final orthodontic simulation that allows for stepwise treatment from a first tooth position, through the intermediate tooth positions and finally to the endpoint positions. In all cases, the endpoint positions are goals, which may or may not be realized in a final treatment plan and simulation.

Referring to Table 2 below, specifics are provided for simulations that utilize nonextraction mechanics and that maintain the archform that was selected at the beginning of simulation set up. All patients will be able to see a simulated result with these mechanics. Some simulations are aligner specific, bracket specific, or both. Thus, the patient can see up front what the end result will be with aligners, brackets, and/or other mechanics. Another element that helps distinguish this disclosure from the prior art includes predefined molar movement specifications by class. Thus, even though the same mechanics may be employed, what the logic is able to virtually include as movement options depends on the molar movement permissible for the simulation mechanics and the MBC. The first nonextraction mechanics in row one of Table 2 indicates that, for MBC I, none of the molars can move forward (i.e., anterior) or back (i.e., posterior). As such, the logic is very limited in what it can do with molars for realignment, such as side-to-side (e.g., buccal-lingual) and perhaps rotation but not posterior or anterior. Nevertheless, the simulation logic can move the archforms forward to create space, but in doing so cannot permit the upper and lower incisors to collide. This limits the feasible results for teeth in the lower dental arch, which may still be crowded when teeth in the upper dental arch are satisfactorily positioned by the logic. With MBC II, however, logic options for molar movement also include being able to move the lower molars anterior. The amount of anterior movement is limited, however to an amount that is within the distance (e.g., mm) used to determine bite class, which may, in embodiments, be about the distance actually measured, or based thereon (e.g., I, II, or III) for each side of the jaw. Adjustment to incisor endpoint positions is available to the logic to help compensate for skeletal differences as impacting collision between upper and lower incisors is never permitted. Since MBC III has a different upper to lower molar relationship than MBC I or II, logic is limited for MBC III simulations to upper anterior molar movement in the amount of bite class III. The logic can also create space by moving the upper dental arch, but again this movement cannot exceed the amount of or within the bite class. If not specifically defined, then logic is not permitted to move the molars anterior or posterior. In fact, there are only a few simulations that allow posterior movement of upper molars and logic cannot ever move lower molars in a posterior direction. Thus, unless specifically defined as posterior movement, the logic is limited to only anterior movement and only in the defined amount for the simulations/subsimulation.

TABLE 2

NONEXTRACTION-MAINTAIN ARCHFORM SIMULATIONS

| MB Class Availability | Extraction/ Nonextraction | Archform | Appliances/ Special Procedure | Simulation/Class Specific Molar Movement: |
|---|---|---|---|---|
| All | Nonextraction | Maintained | Aligners/ Brackets | I: None II: Lower anterior* III: Upper anterior* |
| Class I | Nonextraction | Maintain | Brackets: Minimum Anchorage | Upper/lower anterior (space available) |
| Class II | Nonextraction | Maintained | Brackets: Minimum Anchorage | Lower anterior* |
| Class III | Nonextraction | Maintained | Brackets | Upper Anterior* |
| Class I | Nonextraction | Maintained | Aligners/ Brackets IPR | None |

*Amount of/within bite class

The second nonextraction simulation in row two of Table 2 is specified for MBC I simulations. It differs from the first simulation in that it is available with brackets and not aligners. Different outcomes can be achieved with bracket mechanics, and as such permissible molar movements are also defined differently. For this specific simulation, the logic can move both upper and lower molars in the anterior direction, but only to the extent that space is available. A similar change in mechanics has been programmed for MBC II logic (row three of Table 2). In this case, lower molars may move anterior in the amount of MBC II. Variable positions for incisors are allowed in this scenario, and for different skeletal classes. The class III option (row four or Table 2) with nonextraction and bracket mechanics allows upper molars to be moved in the anterior direction, which is also limited by the severity of the malocclusion.

The last nonextraction simulation shown in Table 2 is specific to class I. It is similar to the first class I mechanics in that the logic cannot move molars in either direction. It differs in that mechanics include interproximal reduction (IPR). IPR reduces the width of teeth lessening the extent of change (e.g., archform advancement) compared to the simulation without. Generally width reduction occurs at contact points between incisors and/or incisors and canines on both the upper and lower dental arch. Tooth width may also be reduced on the upper arch at contact points between canines and premolars. Logic applies IPR in simulations when they are a few degrees (e.g., 3 or less) of being straight relative to the archform. Generally, spaces created by IPR are closed by keeping molars stationary and moving the archform back toward the molars.

Referring to Table 3, below, logic for nonextraction simulations that include expansions instructions will replace the archform selected at the beginning with a corresponding "expansion" archform. The mechanical differences in the first set of simulations of Table 3 and the second set of simulations in Table 3 is the addition of IPR to the expansion. With respect to expansion, simulation logic replaces the selected archform with a corresponding replacement that allows expansion. Expansion can take place laterally to the replacement archform, giving the teeth additional space within which to straighten. Because the arch is expanded and not maintained, the end result will differ from the above simulations that do not allow for expansion. In other words, logic in nonexpansion simulations is limited in the movements it can make to open up space in which teeth can realign without collision. Expansion adds another space-creating variable to the logic and hence it will probably have different paths to the desired end result. This is especially true as the archform has changed, hence the reference for ending arch alignment. If space is created in expansion that needs to be closed (since simulations are prevented from leaving open spaces) space can be closed in the same way as described above with IPR. In fact, IPR, as described above, creates even more space for tooth progression to the endpoint and as such space can be closed by moving the archform back to stationary molars.

TABLE 3

NONEXTRACTION-EXPANSION SIMULATIONS

| MB Class Availability | Extraction/ Nonextraction | Archform | Appliances/ Special Procedure | Simulation/ Class Specific Molar Movement |
|---|---|---|---|---|
| All | Nonextraction | Expanded | Aligners/ Brackets | I: None II: Lower anterior* III: Upper anterior* |
| All | Nonextraction | Expanded | Aligners/ Brackets IPR | I: None III: Lower anterior* III: Upper anterior* |

*Amount of/within the class.

For expansion simulations, simulation logic is directed to replace a selected archform to maintain with a specific expansion archform, which is detailed in Table 4 below. For example, if the selected archform to maintain is "medium ovoid" then the simulation will replace the medium ovoid with the "nonextraction ovoid #1" predefined archform for expansion. When replacing one archform for another, the replacement archform is virtually positioned the same as the selected archform. Notably, simulated expansion does not change the molar movement rules in any of MBC I, II, or III as compared to the nonexpansion simulations of Table 2.

TABLE 4

ARCHFORM REPLACEMENT FOR EXPANSION

| Selected | Replace for Expansion |
|---|---|
| Medium Ovoid | Nonextraction Ovoid #1 |
| Small Ovoid | Medium Ovoid |
| Medium Tapered | Medium Ovoid |
| Small Tapered | Nonextraction Tapered |
| Nonextraction Ovoid #2 | Nonextraction Ovoid #1 |
| Nonextraction Ovoid #1 | Nonextraction Ovoid #1 |
| Medium Square | Nonextraction Ovoid #1 |
| Large Square | Large Square |
| Nonextraction Tapered | Nonextraction Ovoid #1 |

Figure 15:
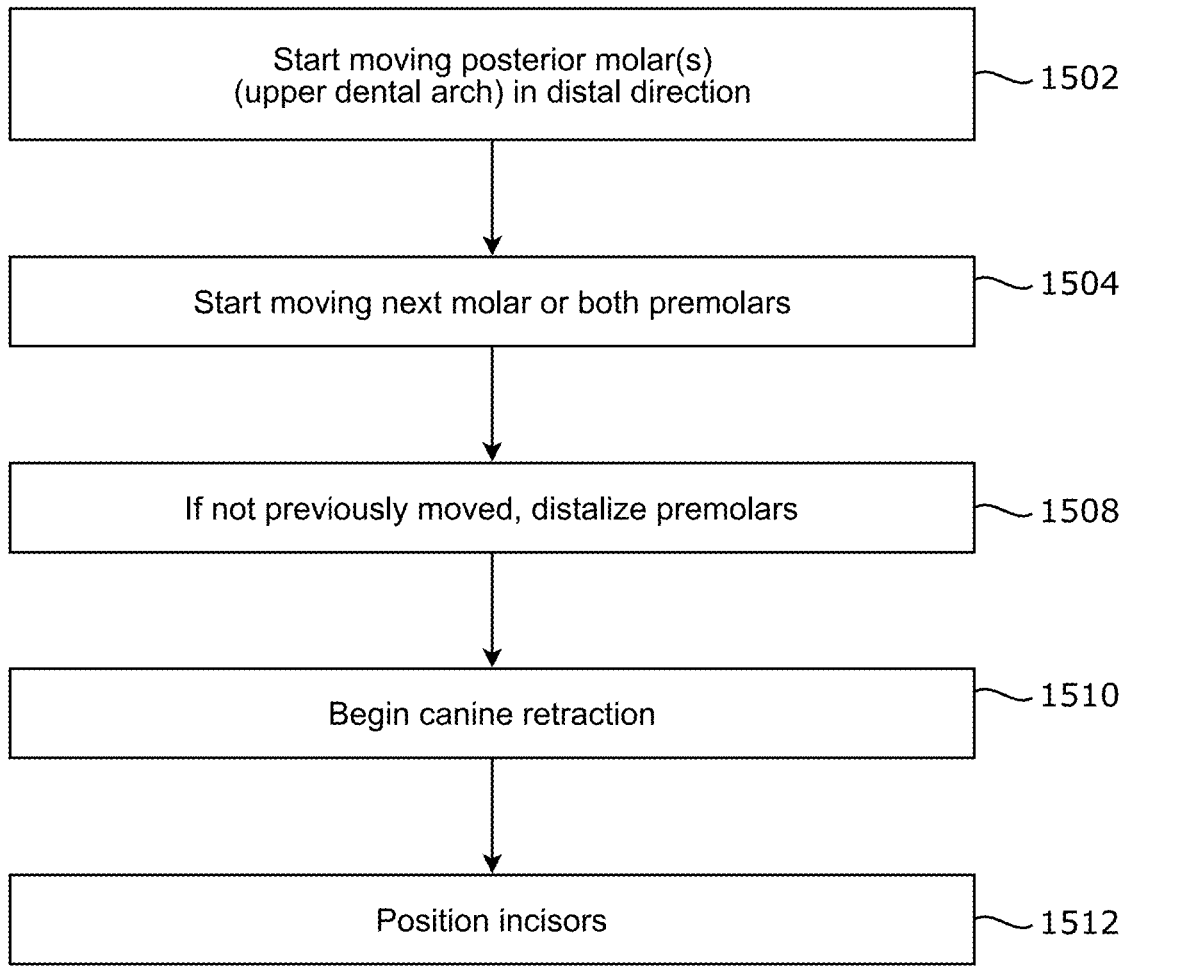
FIG. 15 is a flowchart of simulation movement logic.

There are two different sets of simulations that call for distalization as a logic option. The additional parameters for implementation by logic are cited in Table 5, below. One distalization simulation is a nonextraction simulation and the other tells the logic to virtually extract the upper second molars. The nonextraction version assumes that the third molars have been removed. Nevertheless, if the upper wisdom teeth are indeed present, they can be virtually removed from the simulation. Distalization as described here is specific to MBC II and is not available for other bite classes mainly because the simulation is instructed to move teeth in the upper dental arch, including molars, in a posterior direction. The simulation logic is also allowed to move lower molars forward to the limited amount. With the distalization protocol, it may be possible to shift from an MBC of II to an MBC of I, but embodiments allow an "MCB II finish." Distalization typically adds steps or stages of incremental movement due to the specifics of this protocol. The additional stages may be offset by the end results obtained by distalization mechanics. Distalization mechanics (1500) are detailed in FIG. 15. As with other tooth movement schemes, variance is allowed because patients differ in their start point positioning and as such do not always take the same path to the end result. With distalization, a place to start is with moving the most posterior molar (e.g., 7s, or if 7s are extracted, 6s) back/posteriorly, i.e., in a distal direction (1502). Posterior movement may or may not result in a "bite class 1 finish." At the same time, the distalizing tooth may be expanded, and anterior teeth, including molars, may also be moved anteriorly and/or toward endpoint positions. Additionally, "standard" space-creating efforts may be allowed in embodiments, such as expansion. While the posterior molar moving in a posterior direction, the next molar (if present) or both premolars may start posterior movement (1504). If not already engaged in posterior movement, one or both premolars may be moved in the posterior direction, i.e., in a distal direction (1508). Thereafter, canines may be retracted (1510) and incisors (1512). Again, although described as a sequence, the precise movement start, stop, duration of movement, etc. may depend on the particular person. But, in general, anterior teeth will not move posteriorly until space is created by posterior molar movement. As a side note, due to missing/extracted teeth and distalization, endpoint parameters may be adjusted for certain teeth such as incisors.

TABLE 5

DISTALIZATION SIMULATIONS

| MB Class Availability | Extraction/ Nonextraction | Archform | Appliances/ Special Procedure | Simulation/ Class Specific Molar Movement |
|---|---|---|---|---|
| Class II | Nonextraction | Maintained | Aligners | Upper: posterior* Lower: anterior less than the upper* movement |
| Class II | Extraction (Upper 7s) | Maintain | Aligners | Upper: posterior* Lower: anterior less than the upper* amount |

*The amount/within the amount of the class

The last of the nonextraction simulations are specifically designed for growing patients with an MBC of II. See Table 6. One simulation maintains the archform selected at the beginning of the session and the other replaces the selected archform with an expanded archform as was described in the above expansion simulations. Simulation results may be achieved in reality by the use of either aligners, brackets, or both. Very generally, growth simulations differ from other simulations because a calculated amount is added to molar movement limitations that would otherwise apply per the mechanics specifications. The additional amount of lower molar movement for a growing patient is determined based on age and gender to determine bone maturity, and the WITS value and other skeletal considerations derived from the cephalogram, and bite class amount. Thus, where anterior movement of the lower molars would usually be limited by the amount of MBC II, an additional amount is added to enable the logic for these two simulations to add an additional amount of molar movement, which compensates for the age, gender, etc. of the patient. To clarify, growth considerations are taken into account by simulation logic for these and other simulations. Identification of primary teeth and virtually substituting predefined secondary teeth enable simulation logic to provide a realistic simulation of ending bite/tooth positioning in view of predicted growth. The simulations of Table 6 provide a few examples of simulation mechanics used by simulation logic for patients that will continue to grow. Per the parameters specified in Table 6, molars movements in these two simulations are defined as lower anterior molar movement in the amount of the class/within the range of the class plus the calculated expectation of growth for that patient. Additional strategies for creating/removing space (virtually) are still available to the logic including future perceived future bite issues and how to correct.

TABLE 6

SIMULATIONS FOR GROWING PATIENTS

| MB Class Availability | Extraction/ Nonextraction | Archform | Appliances/ Special Procedure | Simulation/ Class Specific Molar Movement |
|---|---|---|---|---|
| Class II | Nonextraction | Maintained | Aligners/ Brackets | Lower anterior > the class defining amount due to growth |
| Class II | Nonextraction | Expanded | Aligners/ Brackets | Lower anterior > the class defining amount due to growth |

As disclosed above in Tables 2, 3, 5 and 6, there are many nonextraction simulations options available to a patient fitting the criteria for simulation selection. For each simulation option the logic uses the defined mechanics together with the archform reference for alignment to determine not only the end result based on the mechanics, but how to get to that result (collision free) starting with where the patient is at (i.e., teeth position) on that day, wherein this is a first position, an intermediate position (which may function as a new first position, such as with a new scan after an initial treatment and movement from the first position, or a subsequent intermediate position, of which there may be many). Final tooth positioning via simulation is based on the particular simulation's reference table, which specifies goal inclination, angulation, and rotations values for each of the three skeletal classes categorized by the WITS value. Goal endpoint values for nonextraction simulations are taken from the ranges in Table 1. Thus, even though the start point for a particular patient is the same (unless changed and recalculated), the ending results shown via available simulations will differ due to the predetermined mechanics scenarios, including molar movement allowed. The practitioner (and patient) can view simulated tooth movement from start to finish (e.g., as a "straight line" path) or just the end result.

Via the same simulation selection process (e.g., FIG. 14), one or more simulations including tooth extraction may be suitable for a particular patient, if the patient fits criteria set for selection (i.e., MBC, MBC subgroup, age, etc.). Again, there is usually an extraction type simulation scenario that is available to most patients regardless of their MBC; however, due to MBC differences not all extractions are the same for each class. To effectively simulate extractions, the simulation logic removes the indicated teeth from the upper and/or lower dental arches and includes the space made available in its determination of the one or more movement paths toward the desired endpoints of the simulation such as leveling, archform that is selected to be maintained, goal inclination, angulation, and rotation for each tooth not extracted, all without improper collision and correction of malocclusion.

TABLE 7

SIMULATIONS WITH FIRST PREMOLAR EXTRACTION

| MB Class Availability | Extraction/ Nonextraction | Archform | Appliances/ Special Procedure | Simulation/ Class Specific Molar Movement |
|---|---|---|---|---|
| Class I Class II | Extraction (4/4) | Maintain | Brackets Moderate Anchorage | I: Upper/lower anterior; >class amount; about 50% of the available space II: Lower anterior: about 50% of the available space Upper anterior: from about 10% of available space to about 30% of available space |
| Class I Class II | Extraction (4/4) | Maintain | Brackets Moderate to minimum anchorage | I: Upper/Lower anterior > the class amount; about 70% of the available space II: Upper anterior; about 30% to 50% of the available space Lower anterior: about 70% of the available space |
| Class I Class II | Extraction (4/4) | Maintain | Brackets Moderate to maximum anchorage | I: Upper/Lower anterior > the class amount; about 20% of the available space II: Upper anterior: about 10% of the available space; Lower anterior: ≥30% of the available space |
| Class I | Extraction (4/4) | Maintain | Brackets Maximum | None |

There are several upper and lower premolar extraction simulations for patients having an MBC of I or II. Even though the same teeth are "extracted" in the different simulations, mechanics dictates a different result. Namely, one difference in mechanics across the simulation of Table 7 is the amount of anchorage provided per simulation mechanics. Anchorage variations include moderate to minimum, moderate, moderate to maximum, and maximum. Since these simulations extract teeth in both the upper and lower dental arches, space is provided via the extraction for teeth to move into the space. The degree to which upper and lower molars can move into the created space is programmed so that additional problems will not occur as a result of disproportionate upper and lower molar movement. For example, with respect to MBC II, simulation specifics indicate how much upper molars can move forward and lower molars can move forward so that the end result is a bite that aligns upper to lower so that the molars fit without malocclusion or an acceptable limit of malocclusion. As such, for MBC II 4/4 extraction simulations, permissions for lower molar anterior movement typically exceed permissions for upper anterior molar movement. As one example, if lower molars are permitted via simulation specific logic, to move anteriorly to occupy about 70% of the space created by the extraction, then upper molar advancement into the open space is permitted to a lesser extent (e.g., ≤30%). By programming the limits of advancement on upper and lower molars in proportion to/relative to the space made available due to extraction, the degree to which the bite is "off," and the mechanics specified by simulation (e.g., amount of anchorage), the logic will know how far each of the upper and lower molars can advance anteriorly without resulting in a detrimental malocclusion. Anchorages affect the different 4/4 extraction simulations by the amount of molar movement. For example, mechanics that indicate less anchorage will allow more anterior molar movement and mechanics that indicate the most anchorage enables the least amount of anterior molar movement. Moderate amounts of anchorage is between the two extremes. This is also true for anchorage specifications in MBC I (4/4) extraction simulations. Unlike class II, with MBC I simulations the anterior distance traversed by upper and lower molars is the same. For example, with the maximum amount of MBC I anchorage with a 4/4 extraction, neither upper nor lower molars are permitted by logic to move in the anterior direction; hence the logic occupies space made available via extraction with anterior teeth. By extension, the more the molars are permitted by logic to occupy the simulated space, the less space is available to the logic (and reality) to move teeth anterior to the extraction into the space and close the gap. As a result, different specified mechanics in a simulation will reveal a different end result to the patient.

With regard to the below Tables 8 to 16, to the extent that any space is blank, the appropriate reference is found in the master endpoint table, Table 1, except as otherwise provided in the below Tables as they relate to the particular simulations. For example, in the tables below, Table 8, details a mechanical simulation that provides for the extraction of upper 4s, while Table 9 then provides the endpoint table for a mechanic simulation for extraction of only the lower 4s.

TABLE 8

EXAMPLE RANGES FOR POSITION CHANGES WITH UPPER 4S EXTRACTED

| Upper 4s Extracted | Tooth No | Inclination | Angulation | Rotation |
|---|---|---|---|---|
| Molar | 18, 28 | | 89-91 | |
| Molar | 17, 27 | | 88-90 | |
| Molar | 16, 26 | | 84-89 | |
| Premolar | 15, 25 | | 83-89 | |
| Premolar | 14, 24 | | Extracted | |
| Canine | 13, 23 | | 97-99 | |
| Incisor | 12, 22 | | | |
| Incisor | 11, 21 | | | |

TABLE 9

EXAMPLES OF CHANGES MADE TO SIMULATION POSITIONS WITH LOWER 4S EXTRACTED

| Lower 4s Extracted | Tooth No | Inclination | Angulation | Rotation |
|---|---|---|---|---|
| Molar | 38, 48 | | 87-92 | |
| Molar | 37, 47 | | | |
| Molar | 36, 46 | | 80-87 | 7-12 |
| Premolar | 35, 45 | | 80-87 | |

TABLE 9-continued

EXAMPLES OF CHANGES MADE TO SIMULATION POSITIONS WITH LOWER 4S EXTRACTED

| Lower 4s Extracted | Tooth No | Inclination | Angulation | Rotation |
|---|---|---|---|---|
| Premolar | 34, 44 | | Extracted | |
| Canine | 33, 43 | | 94-98 | |
| Incisor | 32, 42 | | | |
| Incisor | 31, 41 | | | |

Simulation options can also include extractions other than first premolars. Predefined mechanics, for example can include extraction of upper first premolars and lower second premolars, upper first premolars only for MBC II candidates and extraction of lower first premolars, or upper second premolars and lower first premolars for MBC III candidates. Mechanics relating to these extraction variations are detailed in Tables 10, 11 and 12 below. Since the mechanics have changed from the 4/4 extractions, end results for candidates that meet the requirements for the simulation will also differ. For example, since lower second molars tend to occupy a different amount space the finish of the simulation may look different that with the 4/4 extractions. This extraction scheme also allows anterior movement of both upper and lower molars, which the amount of lower molar movement limited to the amount of MBC II and the upper molar movement limited to be less than the amount the lower anterior molar movement. With these mechanics, it may be possible for upper and lower molars to relate to each other with a distance that is in the MBC I range. Simulation logic will move anterior teeth of the upper and lower dental arches back toward the molars to close gaps, if any. The final endpoints defined in simulation specific endpoint tables will determine the goal tooth angulation, inclination, and rotation relative to the archform to maintain (e.g., the shape of the selected archform) and the patient occlusal table. The logic determined path from start to finish will avoid collision while also trying to create/maintain symmetry if the two sides of the jaw are asymmetrical. Variations in EPT values may be different from other mechanics schemes to accommodate the different form of extraction and for skeletal class.

Another predefined mechanics scheme MBC II patients includes extraction of the upper first premolars (4s) and no extraction in the lower arch, as is indicated in Table 12, below. Molar movement with this simulation will maintain the class II characterization of upper and lower molars. Namely, logic is told that lower molars may not move forward, but side to side (buccal-lingual) movement is still available as potential lower molar movement. Upper molars, however, may be moved in the anterior direction to a limited extent that keeps the upper/lower molar relationship in the MBC II range.

TABLE 10

SIMULATIONS WITH VARIATIONS ON PREMOLAR EXTRACTION

| MB Class Availability | Extraction/ Nonextraction | Archform | Appliances/ Special Procedure | Simulation/ Class Specific Molar Movement |
|---|---|---|---|---|
| Class II | Extraction (4s/5s) | Maintain | Brackets | Upper anterior: >or equal to the amount of class/from about 10% to 20% of space available Lower anterior: ≥amount of class/from about 70% to about 90% |

TABLE 10-continued

SIMULATIONS WITH VARIATIONS ON PREMOLAR EXTRACTION

| MB Class Availability | Extraction/ Nonextraction | Archform | Appliances/ Special Procedure | Simulation/ Class Specific Molar Movement |
|---|---|---|---|---|
| Class II | Extraction (Upper 4s) | Maintain | Brackets | Upper anterior: from about 10% to about 40% of space available; none for lower |
| Class III | Extraction (Lower 4s) | Maintain | Brackets | Upper anterior: negligible; Lower anterior: ≤10% |
| Class III | Extraction (5s/4s) | Maintain | Brackets | Upper anterior: about 70% of available space; Lower anterior: about 20% of available space |

Simulation mechanics for the last two simulation extraction types in Table 10 above are designed for candidates having an MBC of III. In both of these simulation scenarios the lower first premolars are extracted. Molar movement into the space created by extraction (e.g., lower anterior movement) is about 10% and 20% respectively. In this way, teeth anterior to the extraction can be virtually repositioned into the remaining space with the effect of retracting these teeth to create a positive anterior overjet. With the addition of virtually extracting the upper second premolars, and with minimum anchorage specified, the upper molars can be moved forward to close most of the space. Again, the overall ending effect is a positive anterior overjet. Thus, under these simulation mechanics, patients have additional options to choose from that give the patient a realistic idea of what his/her teeth will look like at the end of a particular treatment plan.

TABLE 11

WITH LOWER 5S EXTRACTED

| Lower 5s Extracted | Tooth No | Inclination | Angulation | Rotation |
|---|---|---|---|---|
| Molar | 38, 48 | | 85-92 | |
| Molar | 37, 47 | | | |
| Molar | 36, 46 | | 83-87 | 5-12 |
| Premolar | | | Extracted | |
| Premolar | 34, 44 | | 93-97 | |
| Canine | 33, 43 | | 93-97 | |
| Incisor | 32, 42 | 53-59 | | |
| Incisor | 31, 41 | 53-59 | | |

TABLE 12

WITH UPPER 4S EXTRACTED

| Upper 4s extracted | Tooth No | Inclination | Angulation | Rotation |
|---|---|---|---|---|
| Molar | 38, 48 | | | |
| Molar | 37, 47 | | | |
| Molar | 36, 46 | | 83-87 | |
| Premolar | 35, 45 | | | |
| Premolar | 34, 44 | 90-95 | | |
| Canine | 33, 43 | | | |
| Incisor | 32, 42 | 54-59 | | |
| Incisor | 31, 41 | 54-59 | | |

Although a simulation is specifically designed to correct posterior crossbite, posterior crossbite may be a subcategory to any of the simulations defined herein. With posterior crossbite, the upper teeth are "inside" the lower teeth. To simulate a correction, the archform to maintain may be replaced by the software logic with an expanded archform on the upper dental arch and a constricted archform on the lower dental arch. Rules for archform replacement are provided in Tables 13 and 14, below. For example, if the upper archform to maintain is a small tapered (FIG. 6 at [618]) then logic will replace the small tapered with a medium ovoid (602). And if the lower archform to maintain is a medium tapered (612), logic with replace this archform with a nonextraction tapered (616). Replacing the archforms in the prescribed manner with cause logic to realign the teeth to change the relationship of the upper and lower teeth thereby showing a corrected crossbite.

TABLE 13

SIMULATION FOR CORRECTING POSTERIOR CROSSBITE

| MB Class Availability | Extraction/ Nonextraction | Archform | Appliances/ Special Procedure | Simulation/ Class Specific Molar Movement |
|---|---|---|---|---|
| Class III | Nonextraction | Posterior Crossbite | Aligners/ Brackets | Upper anterior* to less than the amount of class |

*Amount of Class III

TABLE 14

CROSSBITE ARCHFORM REPLACEMENTS

| Upper Archform to Maintain | Lower Archform to Maintain | Substitute Upper to | Substitute Lower to |
|---|---|---|---|
| Small ovoid or nonextraction taper or small taper | Medium ovoid or small ovoid | Medium ovoid | Small ovoid |
| Small taper | Medium taper | Medium ovoid | Nonextraction taper |
| Medium taper or medium ovoid | Nonextraction #2 | Nonextraction #2 | Medium ovoid |
| Nonextraction taper | Medium ovoid | Nonextraction #2 | Medium ovoid |
| Small square | Large square | Large square | Medium square |
| Small tapered or medium tapered | Nonextraction tapered | Medium ovoid | Nonextraction tapered |

TABLE 15

POST SURGERY SIMULATIONS

| MB Class Availability | Extraction/ Nonextraction | Archform | Appliances/ Special Procedure | Simulation/ Class Specific Molar Movement |
|---|---|---|---|---|
| Class II | Surgery | Maintain | Aligners | II: None via aligners |
| Class III | | | | III: None via aligners |

The last two predefined simulation scenarios shown in Tables 15 and 16 are designed for patients having a larger malocclusion and a WITS that is ≥6 mm (MBC II) or ≥−6 (MBC III). As such, the endpoint simulation results are both post surgery and post alignment. As a result of these mechanics, the entire lower arch is moved forward or posteriorly depending on the class. That is, for class II the lower arch moves forward and for class III the lower arch moves to the back, each movement in the amount of the bite class. Post surgery mechanics options maintain the archform and do not indicate anterior or posterior movement.

TABLE 16

| With Surgery | Tooth No | Inclination | Angulation | Rotation |
|---|---|---|---|---|
| Molar | 18, 28 | 85-89 | 85-91 | |
| Molar | 17, 27 | 85-89 | 85-91 | |
| Molar | 16, 26 | 85-89 | 85-91 | |
| Premolar | 15, 25 | 85-89 | | |
| Premolar | 14, 24 | 85-89 | | |
| Canine | 13, 23 | 89-95 | | |
| Incisor | 12, 22 | | | |
| Incisor | 11, 21 | | | |
| Molar | 38, 48 | | | |
| Molar | 37, 47 | | | |
| Molar | 36, 46 | | 82-88 | |
| Premolar | 35, 45 | | | |
| Premolar | 34, 44 | | | |
| Canine | 33, 43 | | | |
| Incisor | 32, 42 | 50-58 | | |
| Incisor | 31, 41 | 50-58 | | |

A unique feature of the software logic is the ability to "lock" the model obtained via the scan to the cephalogram. Being able to do so allows the practitioner to identify the effects of teeth movement on the alveolar bone for each simulation that is run. Being able to see these effect helps the practitioner guide the patient to a logical option that does not violate the cortical bone layer, which can lead to unwanted complications. Thus, this tool held the practitioner make decisions on a case-by-case basis to decide of the proposed treatment (e.g., simulation mechanics) will adversely affect the starting archform or cause problems with enlargement (e.g., incisor advancement or expansion to the archform) or constriction (e.g., via extraction or otherwise closing spaces between the teeth). Without this tool none of the forgoing are determined by the three-dimensional model alone. The method (1600) shown in FIG. 16 is representative of logic. At the beginning of the office visit while gathering, two points may be put on the cephalogram corresponding to the points on the model used to set the occlusal table (e.g., lower 4s and 6s) if not already automatically done so (1602). When aligned (1604) and adjusted (1606) the cephalogram is recalibrated to the dimension of the model. A screenshot of the model is taken and transparency is adjusted so that when positioned on top of the cephalogram the cephalogram is still visible (1608). With the model image over the cephalogram (1610), the practitioner is able to view the end results of the simulation as they would be in relation to the patient's bone structure. Since the two images are calibrated to realistically sit one on top of the other, any adverse effect of the simulated results on the underlying bone such as being outside of the bone, or being too protrusive, may be identified before treatment is started and that treatment plan may be eliminated as a viable option.

Viewing simulation results in cephalogram lock mode is but one way a patient can view simulation results. Other options include being viewed from the front with the ability to move around as desired, viewing from above and/or below, or a superimposed view showing teeth at the start positions and at the end positions, or combinations thereof. Being able to view multiple simulations based on different mechanics that emulate real life possibilities is a powerful tool for the practitioner to use and the patient to observe actual achievable orthodontic possibilities.

Because the system and embodiments herein utilize scanned data, as well as the specific rules of movements, the precision of the movements are greatly improved as compared to analog systems still currently in use. The significant technical advantages of the system allow for significant advantages over what is currently being done especially due to the clinical relevance, reproducibility, and results that are true to life. Furthermore, the systems allow for customization and modification by the doctor where so desired, and such changes can be performed on the spot, instead of days and/or weeks apart due to simulations being staged by hand. Accordingly, the technical advantages of the system, including but not limited to the origin of the data, the movement rules, the endpoint tables, leveling to the occlusal table, and the limited predefined archforms yield significant clinical advantages and reproducible outcomes not present in the prior systems.

This system relies on predefined parameters that relate to clinically possible tooth movements under specific predefined clinical scenarios to give simulations of end results, rapidly interchanging from the outcome of one scenario to another scenario to provide clinically possible outcomes. One predefined parameter is having a given number of predefined archforms for upper and lower teeth that provide a reference to which teeth are positioned. Changing the archform changes the outcome. For instance, one scenario is to select an archform to maintain and move teeth to that archform whereas another scenario replaces one archform for another. Changing the archform changes the reference to which the simulation can move the teeth e.g., wider, narrower, more oval, square, etc. each option providing a different result and what is actually clinically possible with that result given the starting point of the unique person's anatomy. Another predefined parameter are preset clinical scenarios where each scenario is different from the other. Different scenarios provide different outcomes, with each scenario screened per patient to ensure that the patient only sees outcomes that are actually applicable to him/her. Further, is the use of predetermined endpoints for teeth with the end result being alignment at the archform based on the predetermined endpoints, the patient's anatomy, the mechanics of the scenario, etc. with the endpoints defined ahead of time the software logic can determine the actual end outcome because it has the starting data and the ending data to which it is driving toward in a known ending shape. Thus, when calculating how to go from the start point to the endpoint positions in the defined shape, the logic can incrementally "move" each tooth in space at the same time to determine if the movement will be allowed to go forward or not due to an unacceptable collision. An unacceptable collision will stop teeth from moving in the desired direction, impact upper and lower teeth in a contrary way (e.g., so the bite is off) and/or the teeth will reach the limit of the archform shape and cannot move anymore, but still need to move to become aligned along the arch shape. In this case, the logic will reconfigure tooth movement per rules to find the next acceptable step in the path toward the end. From the acceptable next position, the logic reprocesses current tooth position to the next step toward the endpoint moving each tooth to determine if there are collisions until each tooth is at the last position it can be in based on the arch shape, endpoint parameters, and start position data. That will be the end result that the patient sees via a particular mechanics scenario. Since different mechanics are used for different scenarios, the patient can pick an end result that is desirable to the patient and that the patient knows is achievable via the proposed plan (e.g., extraction, nonextraction, etc.) No other system does this. Current practices are not interested in the start position that the teeth are in; they are only concerned with the end result and project that the end result is achievable by all. Which in all cases is not. These results are fictional for many patients and are not clinically relevant as they cannot be done or are based on an expectation of outcome and not what is actually achievable. The end result is not necessarily obtainable and for current practices not reproducible. In contrast our end results are based on long term stabilization of the teeth with an achievable, predictable end result setting realistic expectations for the practitioner and the patient.

As someone ordinarily skilled in the art will recognize, the method of reaching an orthodontic treatment plan and producing aligners for each individual patient as described above is a significant technical advantage over the way orthodontic treatment is currently performed. Traditionally, in order to start developing a treatment plan, the provider takes an impression of the patient's teeth by placing molding material into a tray into which the patient bites. The tray must be held in place while the molding material sets and hardens. This is uncomfortable for the patient and if the trays are moved during the process, the impression will not be accurate. Additionally, if the margins are not clear, if timing is not correct in mixing the material, if timing is not correct when making the impression or the molding material has expired, the impression will not be accurate. Thus, fidelity is lost in creating the impressions which lead to inaccurate calculations when creating an orthodontic treatment plan.

Accurate tooth models are critical for producing the precision appliances described here within where tooth movements are calculated in fractions of a millimeter. Using the traditional impression method, fidelity is lost at each step of the process. Fidelity is first lost in taking the impression but then, when the dental model is poured, additional fidelity is also lost especially if there are air bubbles in the casting material. If the impressions are distorted, the cast models will lose additional fidelity and accuracy, and thus when using such systems, assumptions must be made to fill in any such missing spaces, or estimations of the lost precision, which is likely to have significant variance between users among one of many possible variables. Thus, the tolerances to which the present system and embodiments utilize to enact the orthodontic simulations cannot be performed by prior art systems.

Once models are made, the maxillary casting must be oriented manually. While the current standard of care uses a dental maxillary plane plate to attempt to recreate accurate orientation, in reality orientation is commonly being manipulated into position by the lab technician in the plaster room often with no accurate record or registration to go by. It is the lab that is deciding the maxillary cast orientation and mounting position. The present invention provides a technical advantage by using precision calculations applied to an accurate scan of the patient's mouth which eliminates mechanical capture of data and inherent imprecision with regard to that type of mechanical capture especially when identifying the occlusal table which is integral to the treatment plans. The imprecision created by the loss of fidelity in the current way of creating dental models makes it impossible to prescribe a treatment plan based upon moving teeth a fraction of a millimeter.

In preferred embodiments, after an orthodontic simulation is determined, in order to enact the simulation, appropriate orthodontic appliances must be used to perform the movements. Classically, this was enacted by the use of brackets, to impart forces on one or more teeth. However, as detailed herein, the orthodontic simulation can be split into a number of individual stages, that are sufficient to follow the logic of movement of about 0.1 mm-0.2 mm or about 1°-3° per stage of movement. This allows for the creation of orthodontic aligners that are positioned to advance the teeth in the defined limits. As defined herein, a doctor and patient may elect to "skip" a given stage, and thus utilize an aligner that is designed to fit two or more stages above, forcing movement of more than about 0.2 mm or about 1°-3°. Here, the skipped stage is not omitted in the plan, just that the teeth bypass this stage to the next stage, with each of the subsequent stages beginning the teeth at an intermediate position in the orthodontic simulation to a final goal position of the teeth.

In some embodiments, an aligner may be utilized for one to about four weeks to effectuate the desired movement to a first intermediate tooth position. A subsequent aligner can then be utilized at that point in time to continue the movement from the first intermediate tooth position to a subsequent tooth position, which may be repeated N number of times. A doctor may choose to rescan the patient at or during any intermediate position. Thus, for example, an aligner is intended to go from a first position to a first intermediate position over the course of 2 weeks. At the end of the two weeks, a new aligner could be ready to be used by the patient. Such new aligner could be preprinted for use, or the patient could visit the doctor, obtain a scan of the patient's teeth and can either compare the previously performed simulation to the now position of the teeth from the scan, or the doctor can simply use the then current position of the teeth as a new starting point of the teeth and perform a new simulation, and obtain a new orthodontic simulation and create a new aligner to proceed to the next intermediate tooth position along the treatment plan. Such intermediate scanning can occur at every stage, or only as desired by the doctor and/or patient to evaluate progress or modify the treatment for any reason.

Thus, as understood in the art, the orthodontic aligner, when printed, fits snugly on a portion of the teeth, and fits very tightly on other teeth. Such tight fit imparts pressure on the teeth to force their movements. As an aligner is worn over the course of days and/or weeks, and as tooth position is modified by use of the aligner, the tight fit should become more relaxed, meaning that the tooth has moved into the desired position of the given aligner. Thus, an orthodontic aligner is formed to fit to an intermediate tooth position as compared to the then present tooth position, and by a patient wearing the aligner, the treatment plan will move the teeth to the intermediate position. This can be repeated N number of times in order to complete the movement to the final desired tooth position.

Thus, as a non-liming example, a patient has a single tooth, the 11 tooth (front incisor) that is off of the archform to be maintained as defined by the orthodontic simulation. After obtaining an intraoral scan and calculation, by the simulation logic, the occlusal table, molar bite class, and fitting the archform, a total movement of ten degrees of the one 11 tooth is desired, with no other movements necessary. The simulation designs ten stages, and the doctor and patient agree to skip or bypass the odd numbered stages to effectuate the treatment in a total of five aligners, providing for a rotation of two degrees between the first stage and each intermediate stage. The patient places the first aligner, and wears it for about one to four weeks, before the second aligner is then used, with the pattern repeating until the last aligner is utilized by the patient and the 11 tooth is adjusted by the desired ten degrees and completing the orthodontic simulation.

In the above example, the orthodontic simulation is simple and the stages can be defined by the doctor and patient to effectuate the treatment. With the plan to omit the odd stages, a printable file, corresponding to the shapes of the aligners corresponding to the even stage numbers, can be printed in office by three-dimensional printing, can be sent offsite to do the same, or given to the patient to allow them to choose a printer. Alternatively, a first aligner only is printed and at a subsequent appointment a subsequent scan performed to ensure proper movement along the treatment plan has been completed and then printing one or more subsequent aligners to complete the treatment plan.

A subsequent patient presents with the 14 and 13 teeth impacting one another, and having only these two teeth visibly off alignment when presenting. A doctor performs an intraoral scan and cephalometric X-ray and incorporates both into the system. The doctor reviews the overlay of the scan and X-ray and fits an archform around the teeth. It is confirmed that only the 13 and 14 teeth are in error with regard to their position on the archform, and that the bite class, and occlusal table are otherwise acceptable for the patient. Notably, each tooth must be rotated, however, in opposing directions, in order to fit to the archform. The simulation identifies that rotation of the 13 cannot occur without first moving the 14, as the mesial portion of the 14 is contacting the distal portion of the 13 tooth. Accordingly, an orthodontic simulation, using the simulation logic moves the 14 tooth first, by moving it 0.1 mm in a distal direction and rotating 2 degrees. The simulation shows that this movement is sufficient to unlock the teeth and prevent their impaction. Subsequent movement can then allow both teeth to rotate without contact. A first stage in the treatment thus performs the movement of the 14 tooth, leaving the 13 tooth in place, reaching a first intermediate stage which no longer has the teeth in contact or preventing their rotation. Movement from the first intermediate stage then to the final stage can be performed with N number of aligners to complete the rotation of the two teeth to meet the final tooth position goal for all teeth, and particularly from the 13 and 14. The different aligners and movement is enacted as detailed herein by manufacturing the different aligners to provide forces on the, here the 13 and 14 teeth, in order to perform the rotation that is desired.

In some instances, the doctor or the patient desires to manufacture the desired trays to effectuate the orthodontic simulation with a third-party. Accordingly, the system can generate the simulation file, which may also include printable/manufacturing files related to the desired aligners to effectuate the orthodontic simulation. Such information can be shared on a cloud based file, sent via electronic transmission or through other storage mediums, and then can be utilized to manufacture the desired appliances.

When the system performs the orthodontic simulation, the various data files, such as the cephalometric X-ray, the intraoral scan, and others, are stored or saved into the system allowing them to then be visually displayed on the system display. The processor of the system then uses the data and or the display of one or a combination of the data to perform the calculations of the system logic according to the rules defined herein. Thus, various points on one or more teeth are identified and used to generate the occlusal table, determine a molar bite class, identify a WITS value, and then after placement of an archform, the rotation of each tooth can be determined. This allows for a present position of each tooth with regard to its position, rotation and angulation to be known, and then using the system logic, one or more proposed end tooth position is identified based on simulation rules. The system can then display the outcome of the one or more of simulations, and determine a mechanics for treatment, such as including or not including extraction and/or brackets instead of aligners as the appliance. The doctor can then adjust positions, endpoint tables of the final tooth position, or select a singular mechanics and simulation, to display a final goal tooth position and result. By making adjustments, the process can then rerun the simulation and display any adjustments based on the fine tuning or movement of the end position and mechanics desired by the doctor and patient. Finally, the processor can communicate run the software logic to generate data files corresponding to the desired aligners to effectuate the desired orthodontic simulation. Accordingly, as disclosed and claimed herein, the present embodiments yield an technical advantage that improves the orthodontic simulation, yielding reproducible results on an individualized patient basis that improve clinical outcomes. The system and simulation logic herein further affords the creation of printable files, which can then be manufactured by 3D printing, molding, CNC, or other formats to rapidly generate orthodontic aligners, when such mechanism is selected for treatment, allowing for a patient to obtain an aligner to effectuate treatment in a fraction of the time as compared to existing solutions.

It will be appreciated that the embodiments and illustrations described herein are provided by way of example and that the present invention is not limited to what has been particularly disclosed. Rather, the scope of the present invention includes both combinations and sub combinations of the various features described above, as well as variations and modifications thereof that would occur to persons skilled in the art upon reading the forgoing description and that are not disclosed in the prior art. Therefore, the various systems and methods may include one or all of the limitations of an embodiment, be performed in any order, or may combine limitations from different embodiments, as would be understood by those implementing the various methods and systems detailed herein.

What is claimed is:
1. A method for providing a result of an orthodontic realignment simulation comprising:
   a. receiving digital images of a patient's mouth taken with an intraoral scanner by a processor and stitching the received digital images together to generate a three-dimensional digital replica of an upper dental arch and/or a lower dental arch of the patient wherein the upper dental arch, the lower dental arch, or both each include at least one tooth;
b. identifying a shape of the upper dental arch, the lower dental arch, or both by the processor, and based on an identified shape of the upper dental arch, the lower dental arch, or both, selecting a complementary archform from a library of predefined digital archforms by the processor wherein the complementary archform is complementary to respective upper and/or lower dental arches in size and shape;
c. virtually positioning the complementary archform on a buccal side of at least one molar and/or premolar of the upper dental arch, the lower dental arch, or both by the processor such that a center of the complementary archform is positioned to be mesial to at least one incisor wherein the upper dental arch, the lower dental arch, and complementary archforms are displayed on a display screen via a graphical user interface (GUI);
d. calculating an initial rotation of each tooth present in the upper dental arch, the lower dental arch, or both by the processor wherein the initial rotation is calculated with respect to the position of the complementary archform;
e. processing a first set of rules by the processor that defines anterior and posterior molar movements that are allowed during a realignment simulation;
f. processing a second set of rules by the processor that defines additional constraints on tooth movement while the processor determines a path of tooth movement for a given tooth to align with the complementary archform during the realignment simulation;
g. processing a third set of rules by the processor, the third set of rules defining one or more particular treatment options to be utilized in a given realignment simulation, the third set of rules utilizing endpoint data that defines a desired final degree of rotation for each tooth in a mouth wherein the desired final degree of rotation is calculated with respect to the position of the complementary archform;
h. based on a result of processing each of the first set of rules, the second set of rules, and the third set of rules, displaying a final position of the at least one tooth in the upper dental arch, the lower dental arch, or both on the GUI wherein when at the final position, the at least one tooth is aligned with the complementary archform and rotated to the desired final degree;
i. using a result from calculating the initial rotation of each tooth present in the upper dental arch, the lower dental arch, or both together with a result from processing the first set of rules, the second set of rules, and the third set of rules, determining a first incremental movement on the determined path of tooth movement for at least one tooth in the upper dental arch, the lower dental arch, or both; and
j. providing data regarding the first incremental movement for the at least one tooth to a fabrication machine wherein the fabrication machine fabricates an aligner based on the data regarding the first incremental movement of the at least one tooth.

2. The method of claim 1 wherein processing each of the first set of rules, the second set of rules, and the third set of rules causes the processor to digitally move the at least one tooth in the upper dental arch, the lower dental arch, or both by stages of incremental movement to determine an acceptable path of movement to the final position and wherein the first set of rules specifies that molars in the lower dental arch cannot be moved in a posterior direction, molars in the upper dental arch can be moved in the posterior direction when called for by the third set of rules, and an increment of molar movement is to be attempted first before incremental movement of teeth anterior thereto if allowed by the second set of rules and third set of rules.

3. The method of claim 2 wherein the second set of rules does not allow incremental movements resulting in teeth collisions that prevent subsequent movement.

4. The method of claim 1 wherein the one or more particular treatment options to be utilized in a given realignment simulation are selected from the group consisting of: nonextraction treatment options, extraction treatment options, distalization treatment options, treatment options that maintain the complementary archform, treatment options that replace the complementary archform, treatment options that correct for posterior crossbite, treatment options that include interproximal reduction (IPR), treatment options that accommodate growth, postsurgery treatment options, and combinations thereof.

5. The method of claim 4 wherein processing the third set of rules comprises identifying an endpoint table from a plurality of endpoint tables that is specific to a selected third set of rules and to a skeletal class in which the patient belongs, the identified endpoint table defining desired endpoint rotations for each tooth in the upper dental arch, the lower dental arch, or both.

6. The method of claim 1 wherein the upper dental arch, the lower dental arch, and the complementary archform are displayed and further comprising receiving input by the processor via the GUI to reposition the archform, select a new archform, or both, and in response thereto processing the first set of rules, the second set of rules, and the third set of rules before displaying a different simulation result on the GUI.

7. The method of claim 1 further comprising the processor:
i. automatically identifying a central axis of each tooth in the lower dental arch;
ii. automatically identifying both first premolars in the lower dental arch and a buccal cusp tip of each first molars in the lower dental arch;
iii. determining a plane created by and resting on both first premolars in the lower dental arch and the buccal cusp tip of each first molar in the lower dental arch and setting the plane as an occlusal table; and
iv. based on the central axis of a tooth and the occlusal table, calculating a starting inclination and angulation of each tooth in the lower dental arch.

8. The method of claim 1 further comprising the processor:
i. receiving a lateral cephalogram of the patient;
ii. identifying a first premolar and a buccal cusp tip of a first molar on the lateral cephalogram;
iii. aligning the first premolar and the buccal cusp tip of the first molar on the lateral cephalogram with the corresponding first premolar and corresponding buccal cusp tip of the first premolar on the lower dental arch wherein the at least one tooth of the lower dental arch is in a post-simulation position;
iv. recalibrating the lateral cephalogram to dimensions of the lower dental arch;
v. overlaying a screenshot of a post-simulation lower dental arch so that it is superimposed over a lower dental arch of the lateral cephalogram; and
vi. adjusting screenshot transparency such that the lateral cephalogram is visible through the overlaid screenshot.

9. The method of claim 1 further comprising the processor:
  i. determining a molar bite class on each side of the patient's mouth, the molar bite class determined by auto identifying a distance between a mesial buccal cusp of a first molar in the upper dental arch and a central groove of a first molar in the lower dental arch;
  ii. based on a determined molar bite class, identifying a grouping of mechanics-based rules designed for the determined molar bite class or, if each side has a different determined molar bite class, identifying the grouping of mechanics-based rules designed for a greater absolute value of the determined molar bite class; and
  iii. identifying a subgrouping of the identified group of mechanics-based rules wherein subgroupings are based on an extent of malocclusion within the determined molar bite class.

10. The method of claim 9 further comprising the processor:
  iv. receiving a lateral cephalogram of the patient;
  v. using the lateral cephalogram, automatically determining an anterior-posterior relationship between a maxilla and a mandible by performing a WITS appraisal wherein a numeric value generated as a result of the WITS appraisal is indicative of a skeletal class; and
  vi. utilizing endpoint data that defines a desired final degree of rotation for each tooth based on the numeric value generated as a result of the WITS appraisal.

11. The method of claim 10 wherein the numeric value is indicative of skeletal class I when the numeric value is between three (3) to negative three (−3) including end points, wherein the numeric value is indicative of a skeletal class II when the numeric value is greater than three, and wherein the numeric value is indicative of skeletal class III when the numeric value is less than negative three (−3).

* * * * *